United States Patent
Mahasheer et al.

(10) Patent No.: US 12,410,421 B2
(45) Date of Patent: Sep. 9, 2025

(54) KERATINASE COMPOSITION

(71) Applicant: Imam Abdulrahman Bin Faisal University, Dammam (SA)

(72) Inventors: Arwa Ali B. Mahasheer, Dammam (SA); Amal Mahmoud, Dammam (SA); Hesham El-Komy, Dammam (SA); Amany Alqosaibi, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 18/473,416

(22) Filed: Sep. 25, 2023

(65) Prior Publication Data

US 2024/0101992 A1 Mar. 28, 2024

Related U.S. Application Data

(62) Division of application No. 17/822,823, filed on Aug. 29, 2022, now Pat. No. 12,146,172.

(60) Provisional application No. 63/332,472, filed on Apr. 19, 2022.

(51) Int. Cl.
*C12N 9/54* (2006.01)
*A23K 10/14* (2016.01)
*A23K 10/26* (2016.01)

(52) U.S. Cl.
CPC ............ *C12N 9/54* (2013.01); *A23K 10/14* (2016.05); *A23K 10/26* (2016.05)

(58) Field of Classification Search
CPC ........... C12N 9/54; A23K 10/14; A23K 10/26
See application file for complete search history.

(56) References Cited

U.S. PATENT DOCUMENTS

2020/0383352 A1 12/2020 Hansted et al.

FOREIGN PATENT DOCUMENTS

| CN | 104507329 A | 4/2015 |
| CN | 107868762 A | 4/2018 |
| CN | 113528493 A | 10/2021 |

OTHER PUBLICATIONS

Wang et al. (Degradation of intact chicken feathers by *Thermoactinomyces* sp. CDF and characterization of its keratinolytic protease. Appl Microbiol Biotechnol (2015), 99:3949-3959). (Year: 2015).*
Shanker et al. (UniProtKB Accession No. A0A2NOYGW1, peptidase; Apr. 18, 2018), (Year: 2018).*
Ghosh et al. (Degradation of raw feather by a novel high molecular weight extracellular protease, from newly isolated Bacillus cereus Dcuw. J Ind Microbiol Biotechnol (2008): 35: 825-834) (Year: 2008).*
Ouled- and Haddar et al. (Expression of alkaline proteinase gene in two recombinant Bacillus cereus feather degrading strains. Folia Microbiol. (2010), 55(1): 23-27). (Year: 2010).*
Su, et al. ; A combination of bioinformatics analysis and rational design strategies to enhance keratinase thermostability for efficient biodegradation of feathers ; Science of the Total Environment ; Nov. 20, 2021 ; Abstract Only ; 3 Pages.
Tian, et al. ; Enhanced extracellular recombinant keratinase activity in Bacillus subtilis SCK6 through signal peptide optimization and site-directed mutagenesis ; RSC Advances, 9 ; Oct. 2, 2019 : 8 Pages.
Yi, et al. ; Enhancement of keratin-degradation ability of the keratinase KerBL from Bacillus licheniformis WHU by proximity-triggered chemical crosslinking ; International Journal of Biological Macromolecules, vol. 163 ; pp. 1458-1470 ; Nov. 15, 2020 ; Abstract Only : 2 Pages.
S8 family peptidase [Bacillus cereus] ; NCBI Reference Sequence: WP_061129616.1 ; https://www.ncbi.nlm.nih.gov/protein/WP_061129616.1 ; 2 Pages.
Multispecies: S8 family peptidase [Bacillus] ; NCBI Reference Sequence: WP_000790934.1 ; https://www.ncbi.nlm.nih.gov/protein/WP_000790934.1!report=genbank&togS=prottop&bl ; 2 Pages.
Almahasheer, et al. ; Novel Feather Degrading Keratinases from Bacillus cereus Group: Biochemical, Genetic and Bioinformatics Analysis ; Microorganisms 2022, 10, 83 ; Jan. 1, 2022 ; 27 Pages.

* cited by examiner

*Primary Examiner* — Iqbal H Chowdhury
(74) *Attorney, Agent, or Firm* — Oblon, McClelland, Maier & Neustadt, L.L.P.

(57) ABSTRACT

Engineered, modified, or mutated *Bacillus* strains that produce keratinases or serine proteases (KerS) that biologically degrade keratin-containing materials, such as feathers; compositions containing these *Bacillus* strains or the keratinases they produce, and methods for biologically degrading keratin-containing materials using these strains or keratinases.

13 Claims, 83 Drawing Sheets

Specification includes a Sequence Listing.

FIG. 8-2

```
                    90              100             110
          ....|....|....|....|....|....|....|....|....|....|....|....|.....
          CTVKEKIKSYKNNPDVEYAEPNYYVHAFWTPNDPYFN
kerS26    ....................................
kerS26uv  ..................................K.
KerS13    ..................................K.
KerS13uv  ..................................K.
KerS13uv+ems ...............................K.
KerS15    ..................................K.
KerS15ems ..................................K.
KerS39    ..................................K.
KerS39ems ..................................K.
KerS1     ..................................K.
KerS1ems  ..................................K.
WP_000790934.1 ...............................K.
WP_061129616.1 ...............................K.
WP_000790931.1 ...............................K.
WP_048539223.1 ...............................K.
WP_171484091.1 ...............................K.
WP_076873679.1 ...............................K.
WP_076886061.1 ...............................K.
WP_000790930.1 ...............................K.
KerS1ems  ..................................K.
MBL3821420.1 .................................
WP_074610243.1 ...............................
WP_078420647.1 ...............................
WP_000790938.1 ...............................
WP_000790937.1 ...............................
WP_088859495.1 ...............................
WP_065211756.1 ...............................
WP_086395645.1 ...............................
WP_006918592.1 ...............................
WP_153581315.1 ...............................
WP_098771659.1 ...............................
```

FIG. 8-2 (Cont'd)

NQYGLQKIQAPQANDSQRSDPGVKVAIIDTGVQGSHPDLASKV

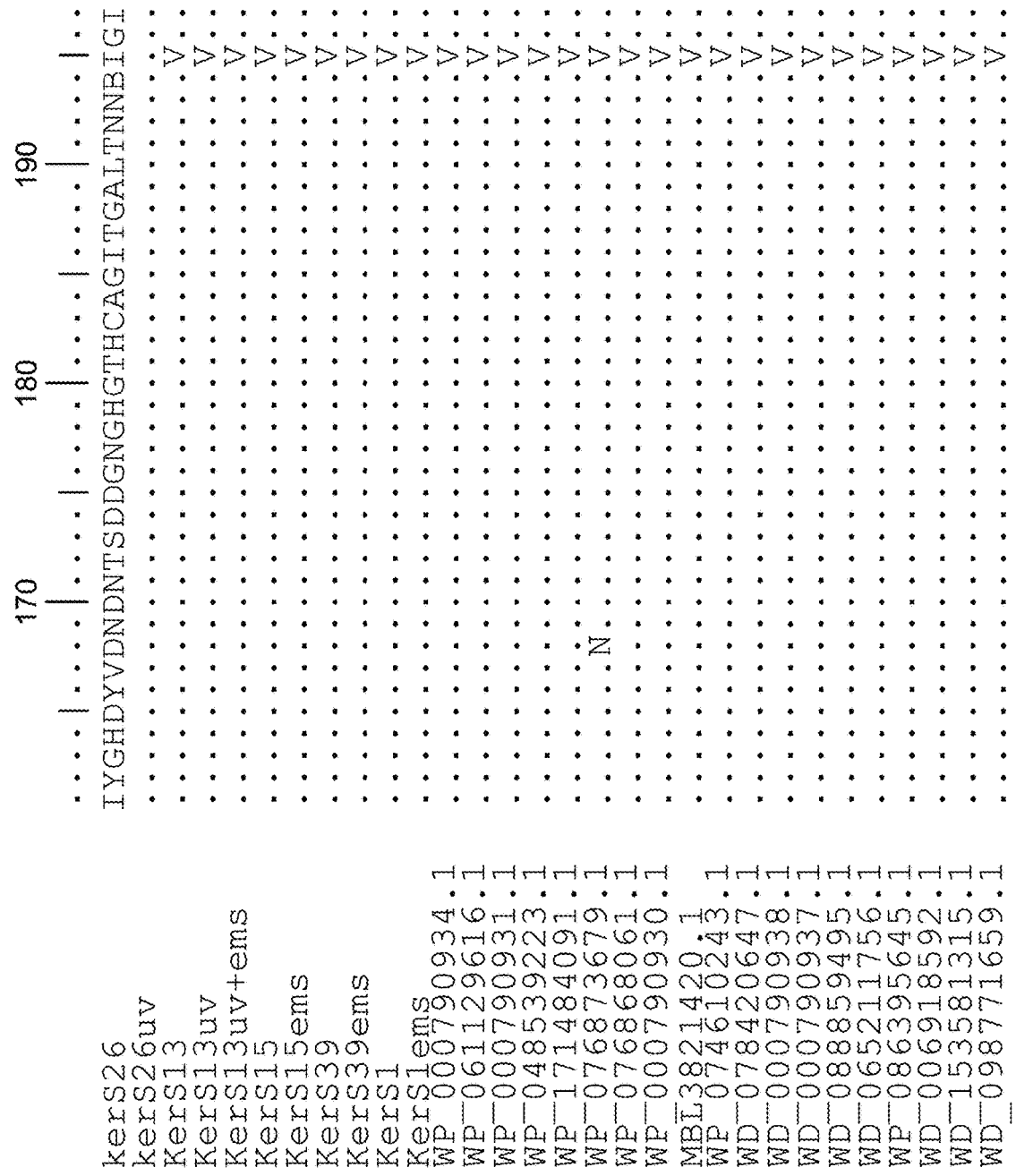

FIG. 8-4 (Cont'd)

```
         280         290         300         310         320
          |           |           |           |           |
NYPAYYBEVIAVGSTDQSDRKSFSTYGBWVDVAAPGSNIYST
..........A..L.K.........................
..........A..L.K..K......................
..........A..LLK..KK.....................
..........A..LLK..LKK....................
..........A..LLK..LLKK...................
..........A..LL...LLLKK..................
.............L....LLLLKK.................
..........A.......LLLLLKK................
..........A......KLLLLLLKK...............
..........A......KKLLLLLLKK..............
..........A......KKKLLLLLLKK.............
..........A......KKKKLLLLLLKK............
..........A......KKKKKLLLLLLKK...........
..........A......KKKKKKLLLLLLKK..........
..........A......KKKKKKKLLLLLLKK.........
..........A......KKKKKKKKLLLLLLKK........
..........A......KKKKKKKKKLLLLLLKK.......
..........A......KKKKKKKKKKLLLLLLKK......
..........A......KKKKKKKKKKKLLLLLLKK.....
..........A......KKKKKKKKKKKKLLLLLLKK....
.................KKKKKKKKKKKKKLLLLLLKK...
..........A.............K................
.........................................
..........A..............................
..........A..............................
..........A..............................
```

MKNKIIVFLSVLSFIIGGFFFNTNTSSAETSSTDYVPNQLIVKFKQNASLSNVQSFHKSVGANVLS
KDDKLGFEVVQFSKGTVKEKIKSYKNNPDVEYAEPNYYVHAFWTPNDPYFKNQYGLQKIQAPQAWD
SQRSDPGVKVAIIDTGVQGSHPDLASKVIYGHDYVDNDNTSDDGNHGTHCAGITGALTNNSVGIA
GVAPQTSIYAVRVLDNQGSGTLDAVAQGIREAADSGAKVISLSLGAPNGGTALQQAVQYAWNKGSV
IVAAAGNAGNTKANYPAYYSEVIAVASTDQLDKKSSFSTYGSWVDVAAPGSNIYSTYKGSTYQSLS
GTSMATPHVAGVAALLANQGYSNTQIRQIIESTSDKITGTGTYWKNGRVNAYKAVQYAKQLQENKA
S

FIG. 10B

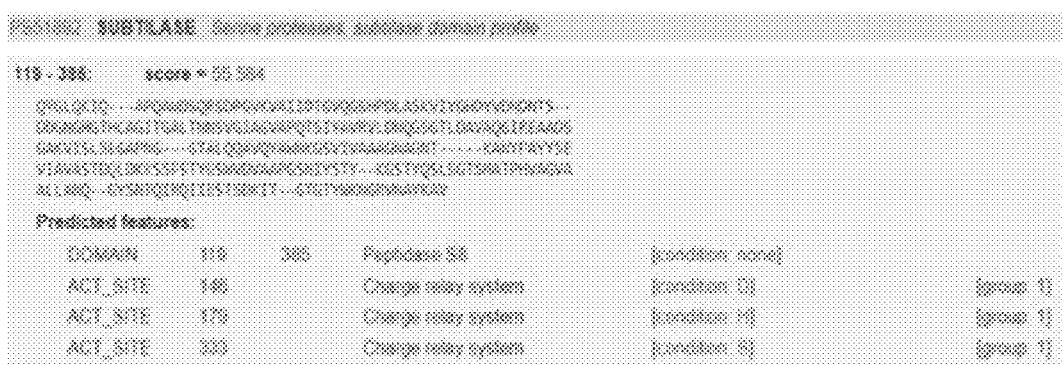

FIG. 16-1 (Cont'd)

```
         40        50        60        70        80        90       100
          |         |         |         |         |         |         |
AGACTGGGATAACTCCGGGAAACCGGGGCTAATACCGGATAACATTTGAACCGCATGGTTC
..............................................................
..............................................................
..............................................................
..............................................................
..............................................................
..............................................................
..............................................................
..............................................................
..............................................T.............
..............................................T.............
..............................................................
..............................................................
........................................GGTTG................
........................................GGTTG................
........................................GGTTG................
........................................GGTTG................
........................................GGTTG................
........................................GCTTGA...............
........................................GCTTGA...............
........................................GCTTGA...............
........................................GCTTGA...............
........................................GCTTGA...............
........................................GCTTG................
........................................GCTTG................
........................................GCTTG................
```

FIG. 16-1 (Cont'd)

```
        140       150       160       170       180       190       200
         |         |         |         |         |         |         |
GGACCCGGCGTCGCATTAGCTAGTTGGTGAGGTAACGGCTCACCAAGGCAACGATGCCGTAGCC
```

FIG. 16-1 (Cont'd)

```
                                              210         220         230
                                    ....|....|....|....|....|....|....|....|
                       GACCTGAGAGGGTGATCGGCCACACTGGGACTGAGACA
S.26
CP063158.1:Bacillus_cereus          ......................................
CP072774.1:Bacillus_cereus          ......................................
CP053972.1:Bacillus_thuringien      ......................................
CP051858.1:Bacillus_thuringien      ......................................
MT372153.1:Bacillus_manliponen      ......................................
MW250250.1:Bacillus_pacificus       ......................................
MW115619.1:Bacillus_paramycoid      ......................................
LC178546.1:Bacillus_subtilis        ......................................
CP050532.1:Bacillus_subtilis        ......................................
CP026662.1:Bacillus_subtilis        ......................................
CP049741.1:Bacillus_velezensis      ......................................
AB592329.1:Bacillus_lichenifor      ...............C......................
MK855401.1:Bacillus_lichenifor      .................-....................
CP045814.1:Bacillus_lichenifor      ......................................
CP042252.1:Bacillus_lichenifor      ......................................
LR698983.1:Bacillus_lichenifor      ......................................
AB680855.1:Bacillus_atrophaeus      ......................................
CP002207.1:Bacillus_atrophaeus      ......................................
CP007640.1:Bacillus_atrophaeus      ......................................
```

FIG. 16-1 (Cont'd)

CGGCCCAGACTCCTACGGGAGGCAGCAGTAGGGAATCTTCCGCAATGGACGAAAGTCTGACG

FIG. 16-1 (Cont'd)

```
                                          310       320       330
                                    ....|....|....|....|....|.*..|...*...
S.26                                GAGCAACGCCGCGTGAGTGATGAAGGCTTTCGGGTCGT
CP063158.1:Bacillus_cereus          ......................................
CP072774.1:Bacillus_cereus          ......................................
CP053972.1:Bacillus_thuringien      ......................................
CP051858.1:Bacillus_thuringien      ......................................
MT372153.1:Bacillus_manliponen      ......................................
MW250250.1:Bacillus_pacificus       ......................................
MW115619.1:Bacillus_paramycoid      ......................................
LC178546.1:Bacillus_subtilis        ..........................T......A....
CP050532.1:Bacillus_subtilis        ..........................T......A....
CP026662.1:Bacillus_subtilis        ..........................T......A....
CP049741.1:Bacillus_velezensis      ..........................T......A....
AB592329.1:Bacillus_lichenifor      ..........................T......A....
MK855401.1:Bacillus_lichenifor      ..........................T......A....
CP045814.1:Bacillus_lichenifor      ..........................T......A....
CP042252.1:Bacillus_lichenifor      ..........................T......A....
LR698983.1:Bacillus_lichenifor      ..........................T......A....
AB680855.1:Bacillus_atrophaeus      ..........................T......A....
CP002207.1:Bacillus_atrophaeus      ..........................T......A....
CP007640.1:Bacillus_atrophaeus      ..........................T......A....
```

FIG. 16-1 (Cont'd)

```
         340        350        360        370        380        390        400
          |          |          |          |          |          |          |
AAAACTCTGTGTTAGGGAAGAACAAGTGCTAGTTGAATAAGCTGGCACCTTGACGGTACCT
..................................................................
..................................................................
..................................................................
..................................................................
.....G...........................A.CGT.C.....G.GC..T.............
.....G.............................CGT.C.....G.GC..T.............
.....G.............................CGT.C.....G.GC..T.............
.....G...........................A.CGT.CA....G.GC..T.............
..................................A.CGT.C....G.GC..T.............
..................................A.CGT.C....G.GC..T.............
..................................A.CGT.C....G.GC..T.............
..................................A.CGT.C....G.GC..T.............
.....G............................CGT.CA....G.GC..T.............
.....G............................CGT.CA....G.GC..T.............
.....G............................CGT.CA....G.GC..T.............
```

FIG. 16-1 (Cont'd)

```
                              410        420        430
                              |    |     |    |     |    |
s.26                          AACCAGAAAGCCACGGCTAACTACGTGCCAGCAGCCGC
CP063158.1:Bacillus_cereus    ....................................
CP072774.1:Bacillus_cereus    ....................................
CP053972.1:Bacillus_thuringien ....................................
CP051858.1:Bacillus_thuringien ....................

```
                                    510       520       530
                                    |    |    |    |    |    |    ★    ★
S.26                                TCTTAAGTCTGATGTGAAAGCCCACGGCTCAACCGTGG
CP063158.1:Bacillus_cereus          ......................................
CP072774.1:Bacillus_cereus          ......................................
CP053972.1:Bacillus_thuringien      ......................................
CP051858.1:Bacillus_thuringien      ......................................
MT372153.1:Bacillus_manliponen      ......................................
MW250250.1:Bacillus_pacificus       ......................................
MW115619.1:Bacillus

```
                                        610       620       630
                                    ....|....|....|..★.|....|....|....|...
S.26                                GTGAAATGCGTAGAGATATGGAGGAACACCAGTGGCGA
CP063158.1:Bacillus_cereus          ......................................
CP072774.1:Bacillus_cereus          ......................................
CP053972.1:Bacillus_thuringien      ......................................
CP051858.1:Bacillus_thuringien      ......................................
MT372153.1:Bacillus_manliponen      ......................................
MW250250.1:Bacillus_pacificus       ......................................
MW115619.1:Bacillus_paramycoid      ......................................
LC178546.1:Bacillus_subtilis        .................G....................
CP050532.1:Bacillus_subtilis        .................G....................
CP026662.1:Bacillus_subtilis        .................G....................
CP049741.1:Bacillus_velezensis      .................G....................
AB592329.1:Bacillus_lichenifor      ............A....G....................
MK855401.1:Bacillus_lichenifor      .................G....................
CP045814.1:Bacillus_lichenifor      .................G....................
CP042252.1:Bacillus_lichenifor      .................G....................
LR698983.1:Bacillus_lichenifor      .................G....................
AB680855.1:Bacillus_atrophaeus      .................G....................
CP002207.1:Bacillus_atrophaeus      .................G....................
CP007640.1:Bacillus_atrophaeus      .................G....................
```

FIG. 16-2 (Cont'd)

```
     640        650        660        670        680        690        700
      |    .    |    .    |★   .    |    .    |★   .    |    .    |★   .    |
AGGCGACTTTCTGGTCTGTAACTGACACTGAGGCGCGAAAGCGTGGGAGCAAACAGGATTA
..............................................................
..............................................................
..............................................................
..............................................................
..............................................................
................................C.......G..........A..........G....
................................C.......G..........A..........G....
................................C.......G..........A..........G....
................................C.......G..........A..........G....
................................C.......G.....................G....
................................C.......G.....................G....
................................C.......G.....................G....
................................C.......G.....................G....
................................C.......G..........A..........G....
................................C.......G..........A..........G....
................................C.......G..........A..........G....
```

(Note: alignment of variant positions approximated; figure shows multiple sequences with substitutions C, G, A, G at indicated positions relative to the reference.)

FIG. 16-2 (Cont'd)

```
                                         710       720       730
                                     ....|....|....|....|....|....|....|...
S.26                                 GATACCCTGGTAGTCCACGCCGTAAACGATGAGTGCTA
CP063158.1:Bacillus_cereus           ......................................
CP072774.1:Bacillus_cereus           ......................................
CP053972.1:Bacillus_thuringien       ......................................
CP051858.1:Bacillus_thuringien       ......................................
MT372153.1:Bacillus_manliponen       ......................................
MW250250.1:Bacillus_pacificus        ......................................
MW115619.1:Bacillus_paramycoid       ......................................
LC178546.1:Bacillus_subtilis         ......................................
CP050532.1:Bacillus_subtilis         ......................................
CP026662.1:Bacillus_subtilis         ......................................
CP049741.1:Bacillus_velezensis       ......................................
AB592329.1:Bacillus_lichenifor       ......................................
MK855401.1:Bacillus_lichenifor       ......................................
CP045814.1:Bacillus_lichenifor       ......................................
CP042252.1:Bacillus_lichenifor       ......................................
LR698983.1:Bacillus_lichenifor       ......................................
AB680855.1:Bacillus_atrophaeus       ......................................
CP002207.1:Bacillus_atrophaeus       ......................................
CP007640.1:Bacillus_atrophaeus       ......................................
```

```
       840       850       860       870       880       890       900
         |         |         |         |         |         |         |
GGCCCGCACAAGCGGTGGAGCATGTGGTTTAATTCGAAGCAACGCGAAGAACCTTACCAGGT
```

FIG. 16-2 (Cont'd)

```
                                        910       920       930
                                    ....|....|....|★...|....|....|....|★..
S.26                                CTTGACATCCTCTGAAAACCCTAGAGATAGGGCTTCTC
CP063158.1:Bacillus_cereus          ......................................
CP072774.1:Bacillus_cereus          ......................................
CP053972.1:Bacillus_thuringien      ......................................
CP051858.1:Bacillus_thuringien      ......................................
MT372153.1:Bacillus_manliponen      ......................................
MW250250.1:Bacillus_pacificus       ......................................
MW115619.1:Bacillus_paramycoid      ......................................
LC178546.1:Bacillus_subtilis        ...............C..T............A.G..C.
CP050532.1:Bacillus_subtilis        ...............C..T............A.G..C.
CP026662.1:Bacillus_subtilis        ...............C..T............A.G..C.
CP049741.1:Bacillus_velezensis      ...............C..T............A.G..C.
AB592329.1:Bacillus_lichenifor      ...............C....................C.
MK855401.1:Bacillus_lichenifor      ...............C....................C.
CP045814.1:Bacillus_lichenifor      ...............C....................C.
CP042252.1:Bacillus_lichenifor      ...............C....................C.
LR698983.1:Bacillus_lichenifor      ...............C....................C.
AB680855.1:Bacillus_atrophaeus      ...............C.C..................C.
CP002207.1:Bacillus_atrophaeus      ...............C.C..................C.
CP007640.1:Bacillus_atrophaeus      ...............C.C..................C.
```

FIG. 16-2 (Cont'd)

```
          940         950         960         970         980         990         1000
           |  .  .  .  |  .  .  .  |  .  .  .  |  .  .  .  |  .  .  .  |  .  .  .  |
           CTTCGGGAGCAGAGTGACAGGTGCATGGTTGTCGTCAGCTCGTGTCGTGAGATGTTGGG
```

FIG. 16-3

```
                                            1010      1020      1030
                                        ....|....|....|....|....|....|....|...
S.26                                    TTAAGTCCCGCAACGAGCGCAACCCTTGATCTTAGTTG
CP063158.1:Bacillus_cereus              ......................................
CP072774.1:Bacillus_cereus              ......................................
CP053972.1:Bacillus_thuringien          ......................................
CP051858.1:Bacillus_thuringien          ......................................
MT372153.1:Bacillus_manliponen          ......................................
MW250250.1:Bacillus_pacificus           ......................................
MW115619.1:Bacillus_paramycoid          ......................................
LC178546.1:Bacillus_subtilis            ......................................
CP050532.1:Bacillus_subtilis            ......................................
CP026662.1:Bacillus_subtilis            ......................................
CP049741.1:Bacillus_velezensis          ......................................
AB592329.1:Bacillus_lichenifor          ......................................
MK855401.1:Bacillus_lichenifor          ......................................
CP045814.1:Bacillus_lichenifor          ......................................
CP042252.1:Bacillus_lichenifor          ......................................
LR698983.1:Bacillus_lichenifor          ......................................
AB680855.1:Bacillus_atrophaeus          ......................................
CP002207.1:Bacillus_atrophaeus          ......................................
CP007640.1:Bacillus_atrophaeus          ......................................
```

FIG. 16-3 (Cont'd)

```
1040        1050       1060       1070       1080       1090       1100
  |    ★   . |  ★  . |    .    |    .    |    .    |    .    |    .    |
CCATCATTAAGTTGGGCACTCTAAGGTGACTGCCGGTGACAAACCGGAGGAAGGTGGGGATG
```

FIG. 16-3 (Cont'd)

```
                                            1110      1120      1130
                                        ....|....|....|....|....|....|....|...
S.26                                    ACGTCAAATCATCATGCCCCTTATGACCTGGGCTACAC
CP063158.1:Bacillus_cereus              ......................................
CP072774.1:Bacillus_cereus              ......................................
CP053972.1:Bacillus_thuringien          ......................................
CP051858.1:Bacillus_thuringien          ......................................
MT372153.1:Bacillus_manliponen          ......................................
MW250250.1:Bacillus_pacificus           ......................................
MW115619.1:Bacillus_paramycoid          ......................................
LC178546.1:Bacillus_subtilis            ......................................
CP050532.1:Bacillus_subtilis            ......................................
CP026662.1:Bacillus_subtilis            ......................................
CP049741.1:Bacillus_velezensis          ......................................
AB592329.1:Bacillus_lichenifor          ......................................
MK855401.1:Bacillus_lichenifor          ......................................
CP045814.1:Bacillus_lichenifor          ......................................
CP042252.1:Bacillus_lichenifor          ......................................
LR698983.1:Bacillus_lichenifor          ......................................
AB680855.1:Bacillus_atrophaeus          ......................................
CP002207.1:Bacillus_atrophaeus          ......................................
CP007640.1:Bacillus_atrophaeus          ......................................
```

FIG. 16-3 (Cont'd)

```
        1140       1150       1160       1170       1180       1190       1200
         |          |    **    |    *   * *   *  **  |    *    *   * * *   *|**
ACGTGCTACAATGGAGGACGGTACAAAGAGCTGCAAGACCGGGAGGTGGAGCTAATCTCATAAAA
.................................................................
.................................................................
.................................................................
.................................................................
.................................................................
.................................................................
.................................................................
.................................................................
.............A.A...G.A............T........C........C....T
.............A.A...G.A............TA.......C........C....T
.............A.A...G.A............TA.......C........C....T
.............A.A...G.A............TA.......C........C....T
............GA.A...G.A............TA.......C........C....T
............GA.A...G..AG...........CTA.......C........C....T
............GA.A...G..AG...........CTA.......C........C....T
............GA.A...G..AG...........CTA.......C........C....T
............GA.A...G..AG...........CTA.......C....C..C....T
.............A.A...G..............TA.......C........C....T
.............A.A...G..............TA.......C........C....T
.............A.A...G..............TA.......C........C....T
```

FIG. 16-3 (Cont'd)

```
                                              *    |
                                              CCGTTCTCA
S.26
CP063158.1:Bacillus_cereus                    .........
CP072774.1:Bacillus_cereus                    .........
CP053972.1:Bacillus_thuringien                .........
CP051858.1:Bacillus_thuringien                .........
MT372153.1:Bacillus_maniponen                 .........
MW250

KERATINASE COMPOSITION

CROSS-REFERENCE TO RELATED APPLICATION(S)

The present application is a Division of U.S. application Ser. No. 17/822,823, having a filing date of Aug. 29, 2022 which claims benefit of priority of U.S. Provisional Application No. 63/332,472 having a filing date of Apr. 19, 2022 which is incorporated herein by reference in its entirety.

REFERENCE TO A SEQUENCE LISTING

In accordance with 37 CFR § 1.52(e)(5), the present specification makes reference to a Sequence Listing submitted electronically as a .xml file named "549858US". The .xml file was generated on Dec. 1, 2023 and is 61,332 bytes in size. The entire contents of the Sequence Listing are hereby incorporated by reference.

STATEMENT REGARDING PRIOR DISCLOSURE BY INVENTORS

Aspects of this technology are described by A. A. Almahasheer, et al., *Novel Feather Degrading Keratinases from Bacillus cereus Group: Biochemical, Genetic and Bioinformatics Analysis*, MICROORGANISMS, 2022, 10, 93 which is incorporated by reference for all purposes.

BACKGROUND OF THE INVENTION

Field of the Invention

The invention relates to the fields of microbiology, molecular biology, and industrial biotechnology especially to the design and expression of keratinases having superior keratinolytic activity, enzymatic specificity for particular keratin-containing materials, such as feathers, or superior thermostability.

Description of the Related Art

Keratin is one of a family of structural fibrous proteins also known as scleroproteins. Alpha-keratin (α-keratin) which contains alpha helices, beta-keratin (β-keratin) which contains beta sheets, and gamma-keratin (γ-keratin) are types of keratin found in vertebrates. Keratins are key structural materials making up scales, hair, wool, nails, feathers, horns, claws, hooves, and the outer layer of skin among vertebrates.

Keratin protects epithelial cells from damage and stress. Keratin filaments, which have undergone keratinization, are abundant in the keratinocytes of the hornified layer of the epidermis. Keratin is extremely insoluble in water and organic solvents. This insolubility contributes to the costs of processing and disposing of keratin-containing waste products.

Various types and sources of keratin including that in feathers are described by, and incorporated by reference to, Wang, Bin, Keratin: *Structure, mechanical properties, occurrence in biological organisms, and efforts at bioinspiration*, PROGRESS IN MATERIALS SCIENCE. 2016, 76: 229-318. doi:10.1016/j.pmatsci.2015.06.001.

Feathers are an inevitable byproduct of poultry production. Untreated feather waste is a source of many pathogenic microorganisms and pollutants; Tamreihao, K.; et al., *Feather degradation by keratinolytic bacteria and biofertilizing potential for sustainable agricultural production*. J. BASIC MICROBIOL. 2019, 5, 4-13. Chicken feathers contain 90% keratin which is highly disulfide-bonded and resistant to degradation when treated with proteases such as papain, pepsin, and trypsin; Kalaikumari, S. et al., *J. Bioutilization of poultry feather for keratinase production and its application in leather industry*. J. CLEAN. PROD. 2019, 208, 44-53: Navone, L. et al., *Understanding the dynamics of keratin weakening and hydrolysis by proteases*. PLoS ONE 2018, 13, e0202608; and Tseng, F. C., *Biofibre Production from Chicken Feather*. MASTER'S THESIS, UNIVERSITY OF WAIKATO, Hamilton, New Zealand. 2011. In contrast to many conventional proteases, keratinase breaks down keratin at near-alkaline pHs and at thermophilic temperatures.

Keratinase production has been reported in microorganisms including fungi and bacteria. These include *Bacillus* species such as *Bacillus licheniformis, B. megaterium, B. subtilis, B. cereus,* and *B. pumilus*; Mamangkey, J., et al., *Molecular Identification and Verification of Gene Encoding Bacterial Keratinase from Crocodile (Crocodylus porosus) Feces*. In PROCEEDINGS OF THE 4TH INTERNATIONAL CONFERENCE ON BIOLOGICAL SCIENCES AND BIOTECHNOLOGY, Medan, Indonesia, 8-9 Dec. 2018; IOP Science: Bristol, U K, 2019.

These keratinases belong to the subtilisin group, serine protease (S8 family): Lange, L. et al., *Microbial decomposition of keratin in nature—A new hypothesis of industrial relevance*. APPL, MICROBIOL. Biotechnol. 2016, 100, 2083-2096; Qiu, J. et al., *Microbial enzymes catalyzing keratin degradation: Classification, structure, function*. BIOTECHNOL. ADV. 2020, 44, 107607.

Naturally-occurring keratinases are expressed and produced in the presence of keratin-containing substrate. They usually attack the disulfide (—S—S—) bond of the keratin substrate; Böckle B, et al., (October 1995). *Characterization of a keratinolytic serine proteinase from Streptomyces pactum DSM 40530*. APPL. ENVIRON. MICROBIOL. 1995, 61 (10): 3705-10. PMC 167669. PMID 7487006. However, many naturally-occurring keratinases lack a sufficient desired level of activity, specificity, or stability required for efficient processing of keratin-containing materials, such as those from poultry, cattle, swine or other livestock. Thus, there is on-going demand for new keratinases that more efficiently degrade feather wastes and other keratin-containing materials. Advantageously, new, more efficient keratinases may be used to more efficiently convert keratin-containing wastes into value-added products, including peptides and amino acids.

Keratinases have a wide-variety of different applications including as enzymes for treating or processing other keratin-containing materials like hair, wool, and skin and for removing proteinaceous strains; as enzymes for treatment of leather or textiles, and as enzymes for use in skin care or cosmetic products. Other useful applications for keratinases, are described by, and incorporated by reference to. Li, Q., *Structure, application and biochemistry of microbial keratinases,* FRONT. MICROBIOL. 23 Jun. 2021, hypertext transfer protocol secure://doi.org/10.3389/fmicb.2021.674345; see for example FIG. 6 of Li, et al.

In view of the demand for keratinases with new or superior abilities to degrade keratin as well demand for keratinases having superior stability, the inventors designed and engineered and evaluated the properties of variants of natural KerS keratinases for in multiple applications including those described supra.

BRIEF DESCRIPTION OF THE INVENTION

This disclosure describes isolated, engineered, modified, or mutated serine proteases (KerS) and microorganisms, such as *Bacillus cereus*, expressing them. Specific modifications to the KerS sequence have been found to provide a keratinase with superior activity, specificity, and/or stability. Examples of such keratinases include those produced by strains S1, S13, S15, S26, or S39, analogs or subcultures thereof, or by a strain having all the identifying characteristics of these strains. The disclosed technology provides a variety of engineered, modified, or mutated KerS proteases with different properties, such as a higher or lower activity for degrading keratin, enhanced specificity for particular types of keratin, or a higher or lower pH or thermostability.

The disclosure also describes nucleic acids which encode the keratinases disclosed herein as well as vectors containing these nucleic acids and host cells capable of expressing recombinant keratinases when transformed with these vectors. These nucleic acid sequences include those deduced from the amino acid sequences described herein.

Another aspect of this technology pertains to a method for degrading or hydrolyzing keratin-containing materials by contacting a them with an engineered, modified, or mutated KerS keratinase which advantageously can have differing specificity for particular kinds of keratin, exhibit a higher or lower keratinase activity, exhibit a lesser or greater thermostability, and/or lesser or greater pH stability, or a broader or narrower range of temperature or pH in which the keratinase remains active, than a corresponding not engineered, not mutated, unmodified, or wild-type serine protease.

Other aspects of this technology include methods for producing engineered, modified or mutated KerS proteases. These methods include use of bioinformatics to design and engineer new keratinases, as well as methods of mutagenesis of keratinase genes, identification and isolation of new mutant or modified keratinases, taxonomic characterization of *Bacillus* expressing such keratinases, and methods for cultivating microorganisms expressing the keratinases disclosed herein.

Embodiments of this technology include, but are not limited to, the following.

A method for treating, processing, degrading, unfolding, or hydrolyzing keratin comprising contacting a material comprising keratin with a keratinase or serine protease that has at least 75, 80, 90, 95, 96, 97, 98, 99, <100 or 100% sequence identity to at least one amino acid sequence of SEQ ID NO: 11, 13, 15, 17, 19, 21, 23, 25, 27, 29 or 31 or to an analog or fragment thereof having keratinase activity. These sequences pair with the following *B. cereus* strains SEQ ID NO: 11 pairs with KerS1, SEQ ID NO: 13 pairs with KerS1ems, SEQ ID NO: 15 pairs with KerS13. SEQ ID NO: 17 pairs with KerS13uv, SEQ ID NO: 19 pairs with KerS13uv+ems, SEQ ID NO: 21 pairs with KerS15, SEQ ID NO: 23 pairs with KerS15ems, SEQ ID NO: 25 pairs with KerS26, SEQ ID NO: 27 pairs with KerS26uv, SEQ ID NO: 29 pairs with KerS39, and SEQ ID NO: 31 pairs with KerS39ems.

In some embodiments, the keratinase-producing bacterial strains disclosed herein share 100% sequence identity for their 16s rRNA genes.

This method advantageously uses keratinases derived from *Bacillus* and preferably involves contacting a keratin-containing material with a keratinase, mutant keratinase, keratinase fragment or keratinase analog encoded by at least one nucleic acid sequence of SEQ ID NO: 10, 12, 14, 16, 18, 20, 22, 24, 26, 28 or 30 or by a polynucleotide having at least 75, 80, 90, 95, 96, 97, 98, 99, <100 or 100% sequence identity thereto.

In other embodiments, an analog or engineered or modified keratinase used in the methods disclosed herein will contain 1, 2, 3, 4, 5, 6, 7, 8, 9, 10 or more amino acid deletions, substitutions, or insertions to its amino acid sequence compared to a naturally-occurring or unmodified parent keratinase, such as those described herein by reference herein to sequence identifiers.

Advantageously, a microorganism, such as *Bacillus* or *Bacillus cereus*, contains one or more alterations of its genomic sequences encoding a keratinase or a serine protease; however, in some embodiments other non-keratinase sequences may be altered or epigenetically modified to enhance cell growth or a level of expression of a keratinase.

The keratinase genes and coding sequences disclosed herein may also be expressed in other types of microorganisms or host cells, for example by transforming another microorganism or host cell with a nucleic acid encoding the keratinase. Host cells include the cells of bacteria and fungi, or vertebrate, mammalian or insect cells.

In some embodiments, the keratinase or serine protease is analog of a naturally-occurring keratinase or serine protease which has been engineered, modified, or mutated. These modifications or differences can produce KerS keratinase proteins having less or more keratinase activity than a corresponding not engineered, mutated, unmodified or serine protease or less or more than a naturally-occurring serine protease or keratinase. For example, a keratinase mutant or analog may have 0, <1.01, 1.01, 1.02, 1.05, 1.1, 1.2, 1.3, 1.4, 1.5, 1.6, 1.7, 1.8, 1.9, 2.0, or >2.0 more keratinase activity than a corresponding naturally-occurring or unmodified parent keratinase under equivalent assay conditions.

Alternatively, a corresponding naturally-occurring or unmodified parent keratinase may have 0, <1.01, 1.01, 1.02, 1.05, 1.1, 1.2, 1.3, 1.4, 1.5, 1.6, 1.7, 1.8, 1.9, 2.0, or >2.0 more keratinase activity than a keratinase mutant or analog under equivalent assay conditions.

A *Bacillus* expressing a keratinase as disclosed herein may express the keratinase at a higher or lower level than a corresponding wild-type or parent strain, for example, it may produce 1, 2, 5, 10, 20, 30, 40, 50, 60, 70, 80, 90, 100, or >100 wt % more or less keratinase than the wild-type or parent strain when grown under the same conditions or grown as disclosed herein. This range includes all intermediate values and subranges.

A keratinase may also exhibit an activity (U/mi) ranging from <1, 1, 1.5, 2.0, 2.5, 3.0, 3.5, 4.0, 4.5, 5.0, 5.5, 6.0 or >6.0 as determined by methods disclosed herein.

Feather hydrolysis by a keratinase as disclosed herein may range from <20, 20, 25, 30, 35, 40, 45, 50, 55, 60, 65, 70, 75 or >75 wt % as determined by methods disclosed herein.

Depending on the technological application, a keratinase having a higher or lower keratinase activity or stability may be selected for use in the methods disclosed herein, for example, to adjust the rate of keratinase degradation of a particular keratin-containing substrate such as feathers.

In other embodiments, the keratinase is an analog of a naturally-occurring keratinase which has been engineered, modified, or mutated to provide a KerS protein having less or more thermostability or pH stability than a corresponding not engineered, not mutated, unmodified keratinase such as a naturally-occurring keratinase. For example, it may have 0, <1.01, 1.01, 1.02, 1.05, 1.1, 1.2, 1.3, 1.4, 1.5, 1.6, 1.7, 1.8, 1.9, 2.0, or >2.0 more keratinase thermostability or keratinase pH stability than the corresponding not engineered, not mutated, unmodified or wild-type keratinase under equivalent assay conditions: such as an assay wherein thermostability is measured at 35, 40, 45, 50 or 55° C. and wherein pH stability is measured at pH 6, 6.5, 7, 7.5, 8, 8.5 or 9. A keratinase may also be selected to narrow or broaden the pH or temperature range in which the keratinase is active. Alternatively, a not engineered, not mutated, unmodified or wild-type keratinase may have 0, <1.01, 1.01, 1.02, 1.05, 1.1, 1.2, 1.3, 1.4, 1.5, 1.6, 1.7, 1.8, 1.9, 2.0, or >2.0 more keratinase thermostability or keratinase pH stability than the corresponding engineered, mutated or modified keratinase under equivalent assay conditions; such as an assay wherein thermostability is measured at 35.40, 45, 50 or 55° C. and wherein pH stability is measured at pH 6, 6.5, 7, 7.5, 8, 8.5 or 9. Depending on the technological application, a keratinase having a higher or lower keratinase thermal or pH stability may be selected for use in the methods disclosed herein.

Advantageously, the keratinases disclosed herein are contacted with keratin-containing materials at a pH of 5.5, 6, 6.5, 7, 7.5, 8, 8.5 or 9 or at any intermediate pH value or subrange.

Beneficially, the keratinases disclosed herein are contacted with keratin-containing materials at a temperature ranging from <15, 15, 20, 25, 30, 35, 40, 45, 50, 55, 60, 65, 70, 75 or >75° C. or at any intermediate temperature value or subrange.

Preferably, the keratinases disclosed herein are contacted with keratin-containing materials in an aqueous solution or buffer at a feather (or other keratin-containing material) concentration ranging from <0.1, 0.1, 0.2, 0.5, 1.0, 1.5, 2.0, 5.0, 10.0 or >10.0 wt % or at any intermediate value or subrange of keratin concentration.

Keratinase activity of culture filtrates may be assayed by methods known in the art, such as by use of a modified protocol according to Preczeski, K. P. et al., *Fusarium oxysporum* and *Aspergillus* Sp. as *keratinase producers using swine hair from agroindustrial residues*. FRONT. BIOENG. BIOTECHNOL. 2020, 8, 71, with keratin azure as a substrate. For example, a reaction mixture may contain 0.4 mL of crude enzymes and 1.6 mL of 0.4% keratin azure (Sigma K8500, Saint Louis, MI, USA) in 10 mM tris HCl (pH 8.5) buffer and be incubated at 50° C. for 1 h. Subsequently, the reaction is stopped with 0.8 mL of 10% trichloroacetic acid (TCA) then centrifuged at 5000 rpm for 20 min. A control sample is prepared in a similar manner except that the bacteria were replaced by the same volume of $dH_2O$. A unit of keratinase activity is defined as a 0.01 unit increase in absorbance at 595 nm.

The effect of initial pH or culture pH of the medium on keratinase activity may be determined by methods known in the art, such as the method according to Aly, M. M. et al., *Isolation, identification, and characterization of a keratolytic bacterium from poultry wastes*. IOSR J. PHARM. BIOL. SCI. 2019, 14, 46-50. For example, isolates S1, S15, and S26 may be grown for 72 hours under shaking at 270 rpm on the previously described basal salt medium containing 10 g/A defatted white chicken feathers as a sole C and energy source at an incubation temperature of 45° C. and different initial pH values ranging from 6 to 9. At the end of the incubation period the keratinase activity is determined.

The physical and chemical attributes, such as molecular weight, theoretical isoelectric point (pI), amino acid composition, instability index, aliphatic index, and grand average of hydropathy (GRAVY) may be computed using the ProtParam assessment tool of the ExPASyserver (hypertext transfer protocol://web.expasy.org/protparam/, accessed on 20 Dec. 2021). It was observed that most keratinophilic microbes thrive well under neutral and alkaline pH, the range being 6.0, 6.5, 7.0, 7.5, 8.0, 8.5 to 9.0. Most of the *Bacillus* sp. showed optimal keratinase production at temperatures ranging from 30, 35, 40, 45 to 50° C.; Srivastava, B. et al., *Microbial keratinases: An overview of biochemical characterization and its eco-friendly approach for industrial applications*. J. CLEAN. PROD. 2020, 252, hypertext transfer protocol secure://doi.org10.1016/j.jclepro.2019.119847. Keratinase production was the highest at 0.5% and 1% substrate concentration for *B. licheniformis* ALW1 and *Bacillus* sp. FPF-L, respectively; Abdel-Fattah. M. et al., *Biodegradaotin of feather waste by keratinase produced from newly isolated Bacillus licheniformis* ALW1. J. Genet. Eng. Biotechnol, 2018, 16, 311-318; Nnolim, N. E. et al., *Bacillus* Sp. FPF-1 *Produced keratinase with high potential for chicken feather degradation*. MOLECULES 2020, 25, 1505. However, the highest keratinase activity showed by the disclosed strains was observed at 40° C.-45° C., pH 8-9, a feather concentration 0.5%-1%, and used white chicken feathers as keratin substrate for 72 h. In some embodiments of the invention, the methods disclosed herein are performed using one or more of the parameters disclosed above.

In some embodiments, a mutated keratinase is produced by exposing a parent or wild-type *Bacillus* strain expressing a natural or previously isolated or engineered keratinase, preferably from *Bacillus cereus*, to UV mutagenesis, chemical mutagenesis (e.g. using ethyl methanesulfonate (EMS), 5-bromouracil, base analog 2-amino purine, or other base modifying agents), oligonucleotide- or antisense-based mutagenesis, genetic site-specific mutagenesis, or epigenetic modification. The resulting mutants may be screened for keratinase activity or for the other characteristics disclosed herein by methods known in the art. Advantageously, a keratinase gene or coding sequence of a mutant strain is sequenced and compared to the keratinase polynucleotide, or deduced amino acid, sequence of the wild-type or parent strain used to make the mutant.

In some embodiments, the keratinase is produced by *Bacillus cereus* strains S1, S13, S15, S26, or S39, or is a mutant, an analog or subculture thereof such strains after exposure to a particular mutagen such as UV or EMS. This disclosure encompasses other strains having all the identifying characteristics of a disclosed strain or subcultures of a disclosed strain.

In other embodiments, the keratinase or serine protease is produced by *Bacillus cereus* strains S1, S13, S15, S26, or S39 which have been genetically or epigenetically modified. For example, in some embodiments, the *Bacillus cereus* strain comprises Ker S13-uv, KerS13uv+ems (D137N), S26uv, or KerS39ems.

The inventors found enhancement of keratinase activity in five mutants with 1.51-3.73-fold increased keratinase activity over the wild type. Comparison of KerS gene sequence of the wild and mutant strains by multiple sequence alignment showed D137N substitution in the mutant KerS13uv+ems but not in the wild KerS13. Interestingly, keratinase activity of the mutant S13uv+ems was detected to be 3.73-fold greater activity than the wild type S13. Moreover, seven substitutions (N117K, V195I, A290G, S295L, R297K, T364S. and S368T) distinguished KerS26 and its mutant KerS26uv from other keratinase sequences. In some embodiments, a keratinase as disclosed herein will comprise 1, 2, 3, 4, 5, 6, or 7 of the above seven substitutions to the amino acid sequence of the keratinase it expresses.

Although keratinase activity of the mutant S26uv showed 1.73-fold more activity than the wild S26 strain, no substitutions were detected in keratinase KerS26uv keratinase compared to KerS26. This may be attributed to modifications made to other proteins in this strain or to epigenetic modifications.

Functional prediction of keratinase gene resulted in the detection of serine protease subtilase domain (peptidase S8) at amino acid positions 119-385 of KerS gene, including the catalytic triad subtilase ASP146, subtilase HIS179 and subtilase SER333 (FIG. 10). Most of the keratinases are found in the subfamily S8A including 14 keratinases, their active site contains the catalytic triad of Asp, His and Ser; Martinez, J. P. et al., *Challenges and opportunities in identifying and characterising keratinases for value-added peptide production*. Catalysts, 10, 184. Based on the above, one may select modified keratinases that retain this catalytic triad of Asp, His and Ser, 1 or 2 residues of this triad, or select keratinases retaining the residues at or corresponding to those at positions 119-385.

The catalytic triad plays an important role in the catalytic mechanism. The triad is positioned in the active site of the enzyme, where catalysis take place, and is conserved in all superfamilies of serine protease enzymes; van, G. et al., *Four spatial points that define enzyme families*. Biochem. Biophys. Res. Commun. 2009, 383, 417-420. Interestingly, the detected substitutions in KerS gene (FIG. 10) did not affect the prediction of the subtilase domain and the catalytic triad and accordingly, the inventors consider that these substitutions did not affect KerS function.

In some embodiments, the serine protease or keratinase is part of a viable or dead microorganism, such as *Bacillus cereus* or another host cell expressing it. For example, it may be in the form of a bacterial isolate, membrane fraction, supernatant or insoluble or pellet fraction. In some embodiments, whole cell or partial cell lysates are used in the methods disclosed herein which comprise, or are modified to contain, a keratinase as disclosed herein and other enzymes, such as disulfide reductases or reducing agents such as sulfites, present in a cell that accelerate or assist in digestion of keratin.

In some embodiments, the keratinase is purified or isolated from a crude microbial extract or one or more cellular components thereof, for example, it may be present in a clarified lysate or supernatant of lysed *Bacilli* encoding the keratinase. Alternatively, it may be chromatographically purified using standard methods, for example, it may be isolated from one or more, or all, bacterial proteins or other components or from at least 90, 95, 96, 97, 98, 99 or >99% of other bacterial proteins or components.

Examples of keratinases according to this technology include those described by Tables 1-3, S1, and S2 and those described in FIGS. 1-17.

Another aspect of this technology is a composition comprising a keratinase as disclosed herein or containing a microorganism such as *Bacillus cereus* expressing such a keratinase. One embodiment of such a composition is an enzymatic composition suitable for digesting feathers, wool, human hair, or other keratin-containing materials comprising an effective amount of a keratinase or a microorganism such as *Bacillus cereus* expressing it.

A keratinase as disclosed herein may be used to treat keratin-containing wastes which once treated may be used as components in fertilizers, feed additives or for biogas production. A keratinase as disclosed herein may be used in the textile and leather industries for processing and cleaning materials containing keratin.

A keratinase as disclosed herein may be used in a medicine or cosmetic, for example, as a component in a callus remover, transfer accelerator for use with topical drug therapy (e.g., to increase drug penetration into, or permeability of skin or nails), for acne treatment, in a personal hygiene product or for ear wax removal. Other properties and uses for keratinases are disclosed by, and incorporated by reference to, Vidmar, B. & Vodovnik, M, *Microbial Keratinases: Enzymes with Promising Biotechnological Applications*, FOOD TECHNOL. BIOTECHNOL., 2018, 56(3), 312-328.

The keratinases as disclosed herein may be employed as enzymes for treating or processing keratin-containing materials like hair, wool, and skin, as enzymes for use in, or preparation of, skin care or cosmetic products including depilatories, exfoliatives, callous removers, wound treatments, nail bed treatments, hydrogels, comprising treated or partially digested keratin, or healing aids, or as ingredients in surfactant-containing or other cleaning compositions including products for removing proteinaceous strains or for clearing drains, traps, or drain pipes. The enzymatic properties of keratinase are also useful for scientific work, such as for tissue culture, or as additives in pharmaceutical compositions. In on embodiment, keratinases may be employed to degrade prions, for example, by inclusion in animal feeds or other materials suspected of harboring prions.

In some embodiments the composition will further include one, two or more other proteases, chelating agents, dispersing agents, bases, or acids, such as the other proteases mentioned herein. Removal of disulfide bonds by a keratinase can increase the proteolytic activity of other protease.

In some embodiments, the composition may contain nutrients suitable for growth or viability of a microorganism, such as *Bacillus cereus*, including *Bacillus* culture medium, carbon-, nitrogen-, or sulfur-sources, peptides, yeast extracts, trace metals or minerals, magnesium, calcium or phosphorous, glucose or other sugars. Provision of nutrients can promote the ability of a live bacterium expressing a keratinase to degrade keratin. In one embodiment one or more nutrients are admixed with keratin-containing wastes (such as feathers) to promote or accelerate the growth of bacterial expressing the keratinases disclosed herein.

In one embodiment, the enzymatic composition comprises, in addition to the serine keratinase, a keratin-containing material such as feathers in a form suitable for administration as a feed to an animal. For example, it may contain a keratin-containing material such as hair, wool, feathers, ground feathers, feather meal, and one or more digestive aids, organic acids (e.g., acetic or butyric acid) feeds, vitamins, minerals or other nutritional components.

Feathers or other keratin-containing material may be pre-digested or partially digested using the strains disclosed herein, and the resulting feather meal may be included in an animal feed. Keratinases produced by the strains disclosed herein may be added to animal feed in combination with feathers. In this case the enzymatic degradation of the feathers or other keratin-containing material occurs within the digestive tract of the animal. The feathers may be the sole protein source in the animal feed or there may be an additional protein, carbohydrate or lipid source. To ensure adequate degradation by the keratinase feathers may be ground, steam-treated, or otherwise prepared before adding them to a feed. Animal feeds comprising the digested keratin may be used to feed poultry or other domestic animals. These feeds may also contain other ingredients such as protein meal, cereal grains, cereal byproducts, fats and oils, minerals, vitamins or roots and tubers.

Another aspect of this technology is an enzymatic composition suitable for removing protein-based stains from a fabric without significant damage to the fabric. It comprises an effective amount of the keratinase as described herein and optionally, one or more solvents, surfactants, chelating agents, or other non-keratinase enzymes. Such a composition is applied to a keratin-containing stain for a time and under condition suitable for removal of the keratin in the stain.

Another aspect of this technology is an isolated or purified nucleic acid, such as DNA or RNA, encoding the isolated or purified serine protease or keratinase as disclosed herein. In some embodiments, the isolated or purified nucleic acid will be incorporated into a vector or nucleic acid construct, for example, into a plasmid that can be transformed into a *Bacillus* host cell in order to express the serine protease or keratinase. In another related embodiment, the isolated or purified nucleic acid will be part of a prokaryotic or eukaryotic cell line comprising the vector or nucleic acid construct.

Another aspect of this technology is directed to a method for producing the isolated or purified keratinase or serine protease as disclosed herein comprising culturing a host cell for a time and under conditions suitable for expression of said keratinase and recovering said keratinase or cells expressing the keratinase In some embodiments, the keratinase is purified using at least one of the following steps or methods: cellular disruption (sonication, French press), ion exchange chromatography, cation exchange and gel filtration, size-exclusion chromatography, and/or SDS-PAGE, affinity chromatography (using antibodies or ligands that bind to the keratinase), of an extract containing the serine protease (keratinase).

The foregoing paragraphs have been provided by way of general introduction, and are not intended to limit the scope of the following claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1A describes bacterial isolates after gram staining under the light microscope.

FIG. 1B describes preliminary screening of isolate S26 for proteolytic activity on skim milk agar. It shows the formation of clear zones around the S26 colonies.

FIG. 1C describes a clear growth medium containing feathers prior to inoculation with bacteria.

FIG. 1D shows feather degradation after inoculation with bacterial isolate S1 after 72 h of shaking incubation at 37° C.

FIG. 5A. Wild-type and EMS-mutated isolate S39 showing clear zones of hydrolysis on skim milk agar.

FIG. 5B. Keratinolytic activity of wild-type compared to EMS and UV+EMS-mutated isolates. Bars are the standard error of the mean. Keratinase activity was increased with the mutants S1ems (3.2 U/mL) S13uv+ems (3.5 U/mL), and S39ems (3.7 U/mL) compared with the wild isolates. Mean with the different letters are significantly different according to Duncan's at p<0.05.

FIGS. 6A-1-6A-5 and 6B-1-6B-5 illustrate biodegradation efficiency of the wild-type and mutant isolates.

FIGS. 6A-1-6A-5. Feathers degradation after 72 h of incubation with isolates S13 and S39 and their mutants S13uv+ems and S39ems examined by digital camera. 6A-1 control (no *Bacillus*).

FIGS. 6B-1-6B-5. Feathers degradation after 72 h of incubation with isolates S13 and S39 and their mutants S13uv+ems and S39ems examined by scanning electron microscopy. 6B-1 control (no *Bacillus*).

| keratinase gene | Corresponding SEQ ID Number. |
| --- | --- |
| KerS1 | SEQ ID NO: 11 |
| KerS1ems | SEQ ID NO: 13 |
| KerS13 | SEQ ID NO: 15 |
| KerS13uv | SEQ ID NO: 17 |
| KerS13uv + ems | SEQ ID NO: 19 |
| KerS15 | SEQ ID NO: 21 |
| KerS15ems | SEQ ID NO: 23 |
| KerS26 | SEQ ID NO: 25 |
| KerS26uv | SEQ ID NO: 27 |
| KerS39 | SEQ ID NO: 29 |
| KerS39ems | SEQ ID NO: 31 |

Figure 9:
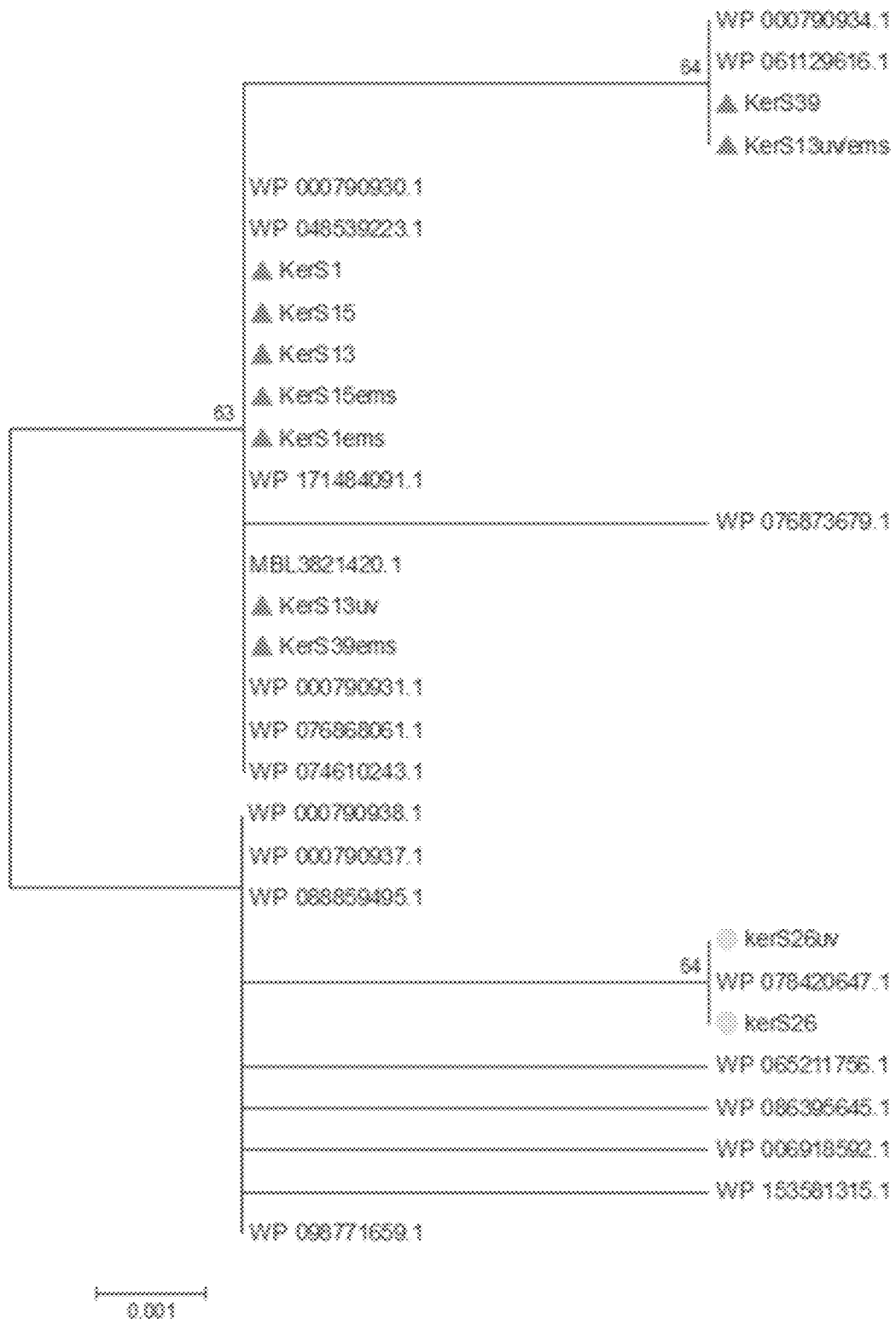

FIG. 9 depicts the neighbor joining phylogenetic analysis of KerS gene against S8 family peptidase *Bacillus cereus* group sequences retrieved from the GenBank database. Keratinase KerS gene sequences were separated into two groups.

FIGS. 10A and 10B illustrate the prediction of the catalytic domain and active sites of keratinase gene KerS13. KerS13 was used to predict its catalytic domain and active sites and corresponds to SEQ ID NO: 15. Functional prediction of keratinase gene resulted in the detection of serine protease subtilase domain (peptidase S8) at amino acid position 119-385 of KerS gene, including the catalytic triad subtilase ASP146, subtilase HIS179, and subtilase SER333.

FIG. 10A. Amino acid sequence given by SEQ ID NO: 15.

FIG. 10B. The catalytic triad subtilase ASP146, subtilase HIS179 and subtilase SER333 with a score of 55.5. The sequence in this figure corresponds to SEQ ID NO: 15. Comparison between SEQ ID NO 15 against prosite database showed that SEQ ID PS51892 is a highly similar sequence to SEQ ID NO 15.

Figure 11:
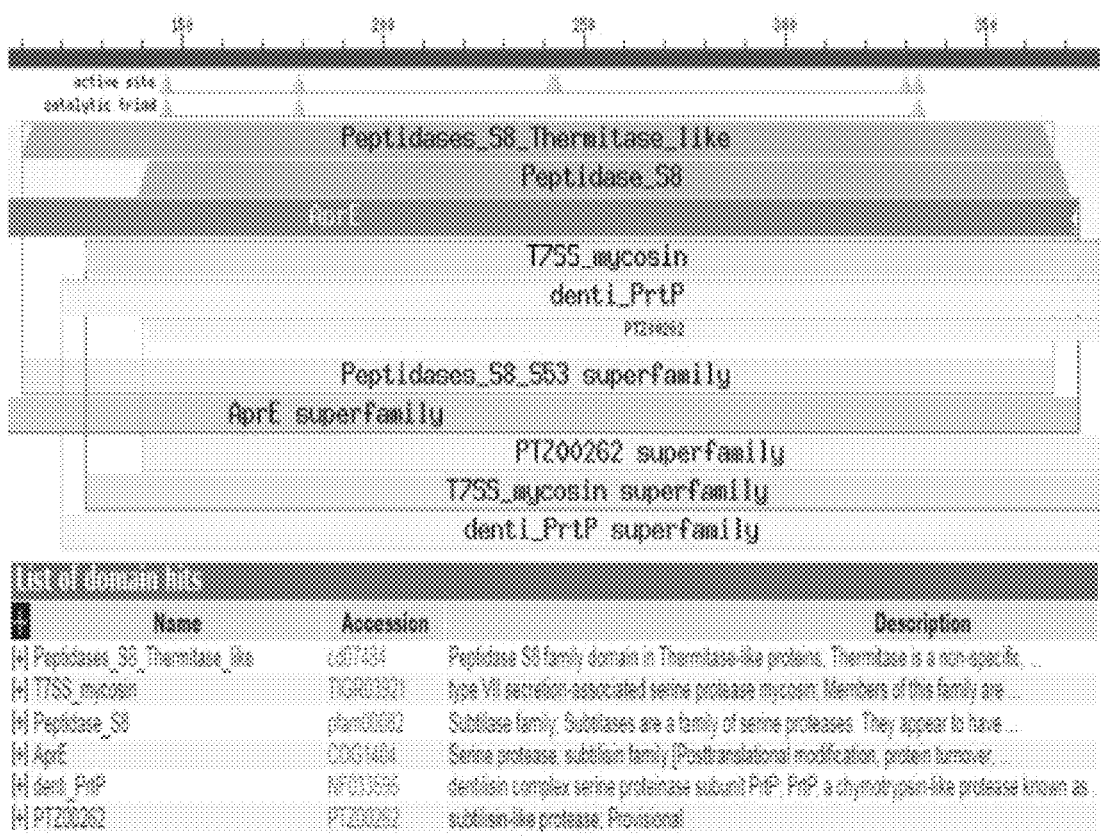

FIG. 11. NCBI conserved domains search analysis showed the similarity between KerS gene disclosed herein and thermitase-like peptidases Sg.

Figure 12A:
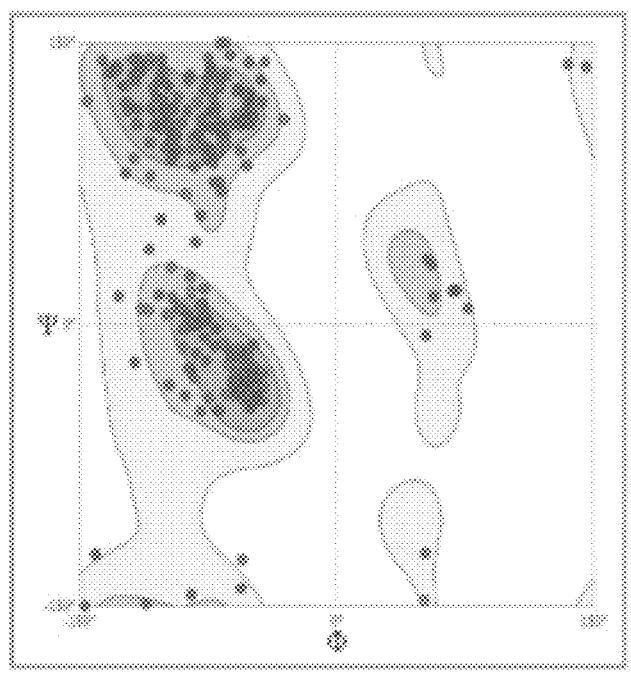

FIG. 12A. Model validation of keratinase 3D structure by Ramachandran plot showing 91.98% favored region and 1.43% of the disallowed region. Amino acids not in the favored region are A324 SER, A46 GLN, A160 VAL, A137 ASP, and A114 PRO. The inventors conducted a Ramachandran plot to validate the stereochemical stability of keratinase structure and to explain the structure of the keratinase of the wild and mutant strains. FIG. 12A shows 91.98% of the amino acid residues in the most favored region, and 1.43% of the remaining residues in the outlier region which indicates the model is of good quality and stability for in silico studies. Most of the keratinases are found in the subfamily S8A including 14 keratinases. Their active sites contain the catalytic triad of Asp, His and Ser; Martinez, J. P. et al., *Challenges and opportunities in identifying and characterising keratinases for value-added peptide production*. Catalysts 2020, 10, 184. Advantageously a keratinase as disclosed herein comprises this catalytic triad of amino acids.

Figure 12B:
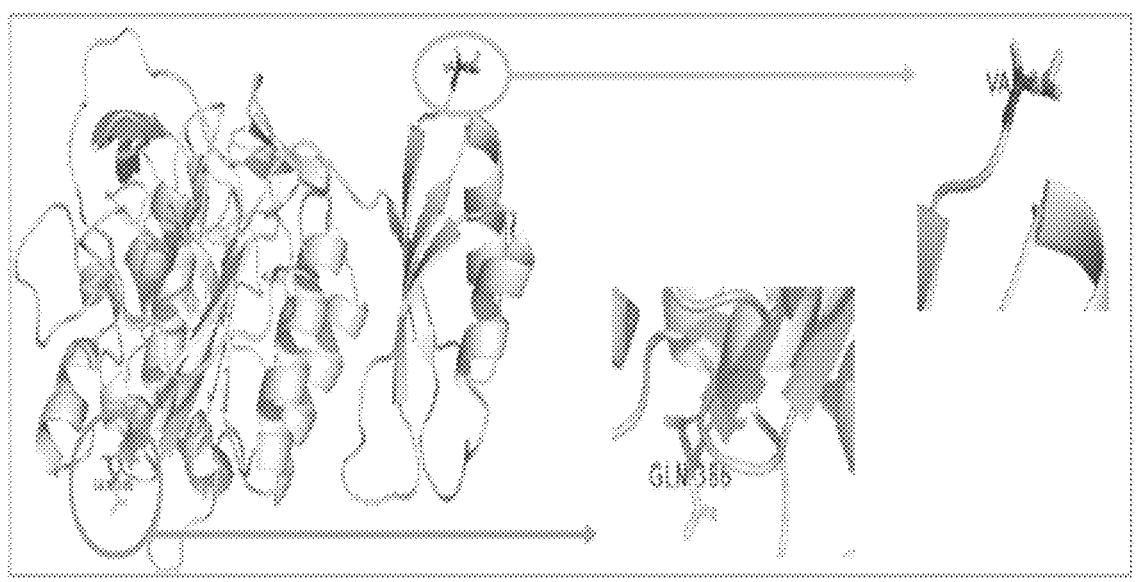

FIG. 12B. Ribbon diagrams of the modeled keratinase showing α-Helices, β-strands, and loop.

Figure 12C:
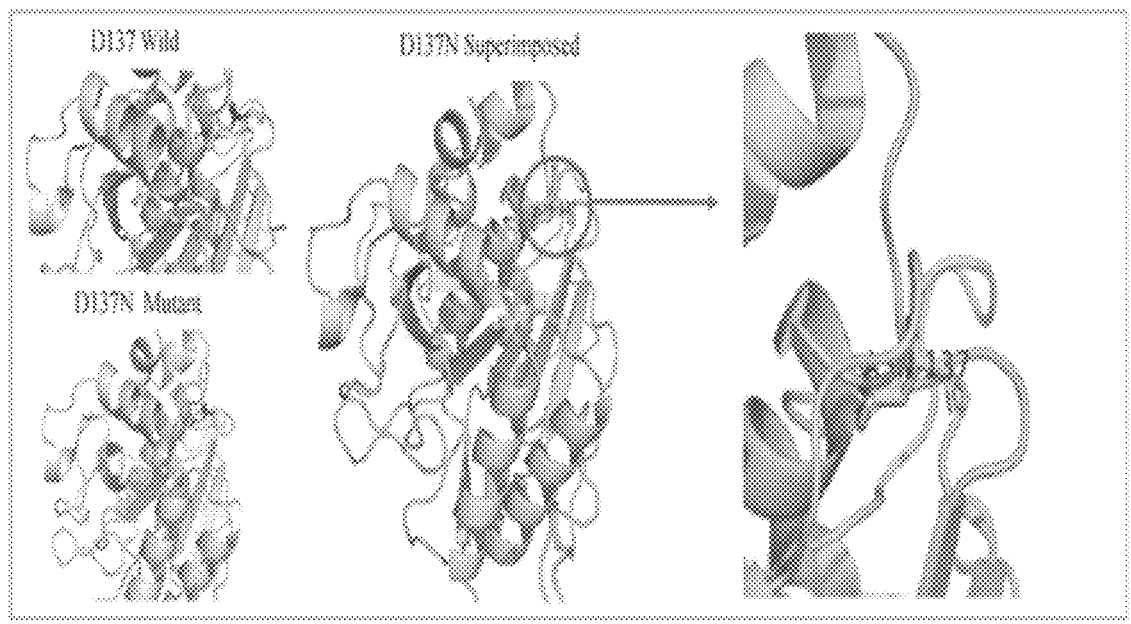

FIG. 12C. Describes structures of D137 wild-type and D137N mutant. The structure of KerS13uv+ems (D137N) is superimposed on the right side of this figure.

Figure 12D:
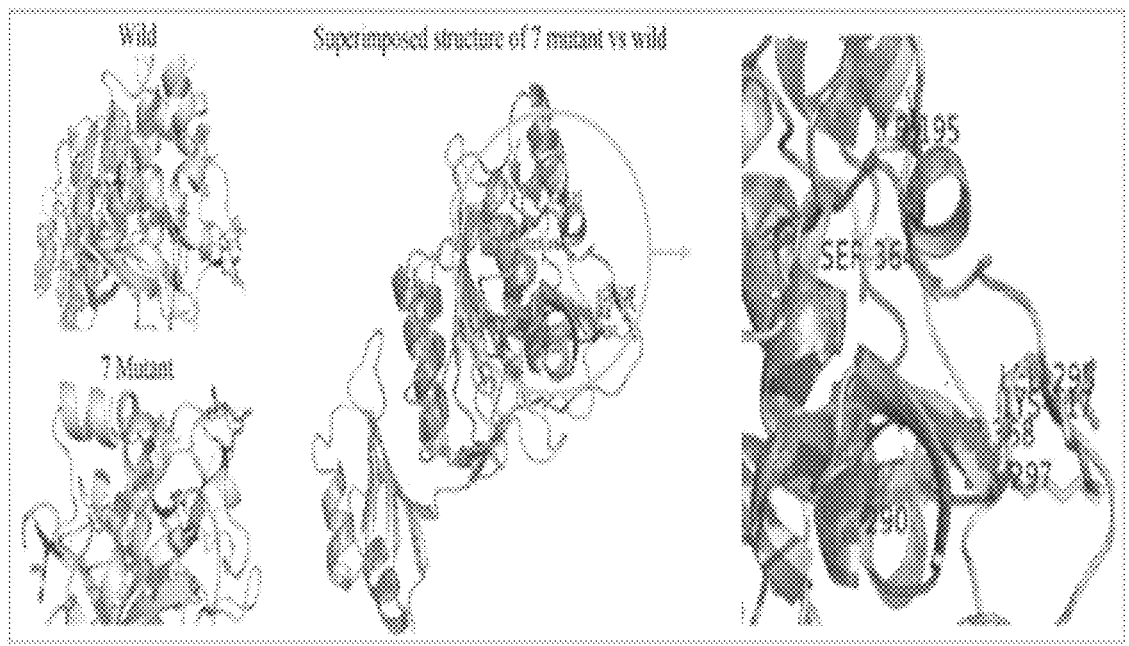

FIG. 12D. Superimposed structure of 7 Mutant that differentiates between wild type and KerS26uv strains.

Figure 13A:
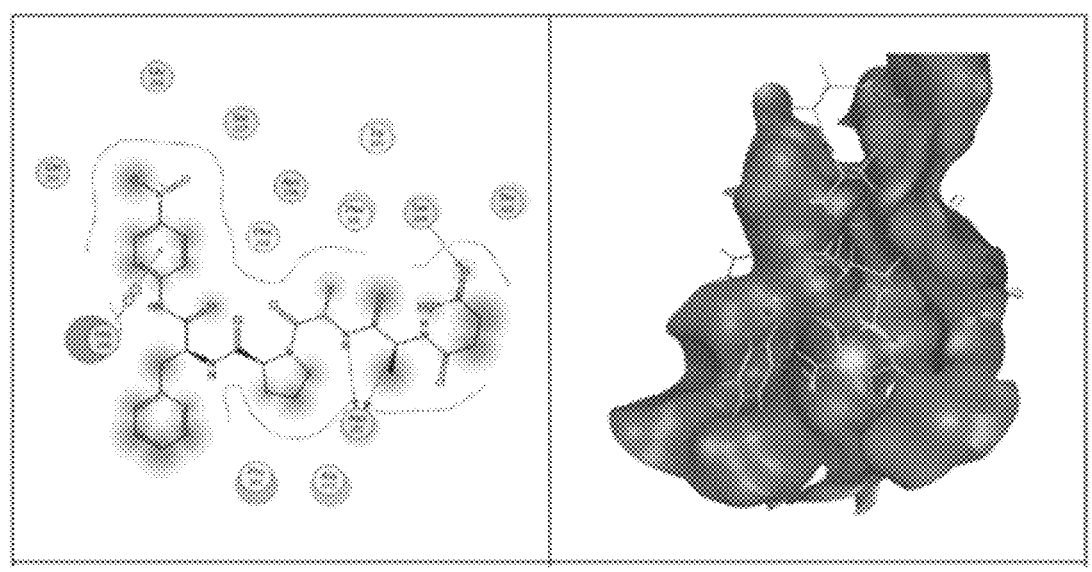

FIG. 13A. Wild keratinase ligand interaction: at left is the 2D structure and on right is the 3D structure. Ligand has three hydrogen bonds: one with Ser 300 and two with Asn 271.

Figure 13B:
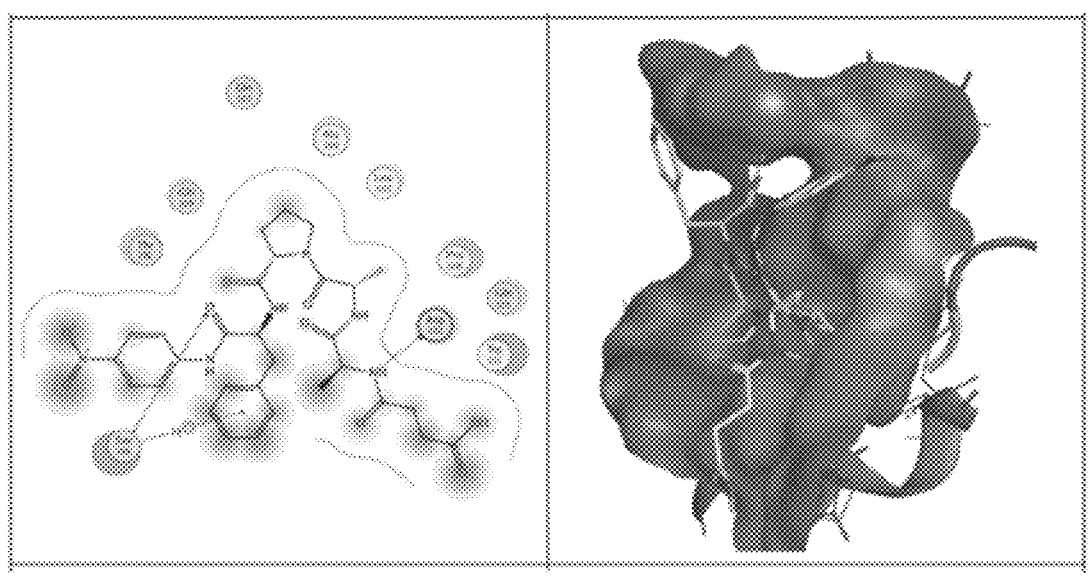

FIG. 13B. The D137N keratinase ligand interaction: at left is the 2D structure and on right is the 3D structure. Ligand has two hydrogen bonds: Asp 132 and Ser 194.

Figure 13C:
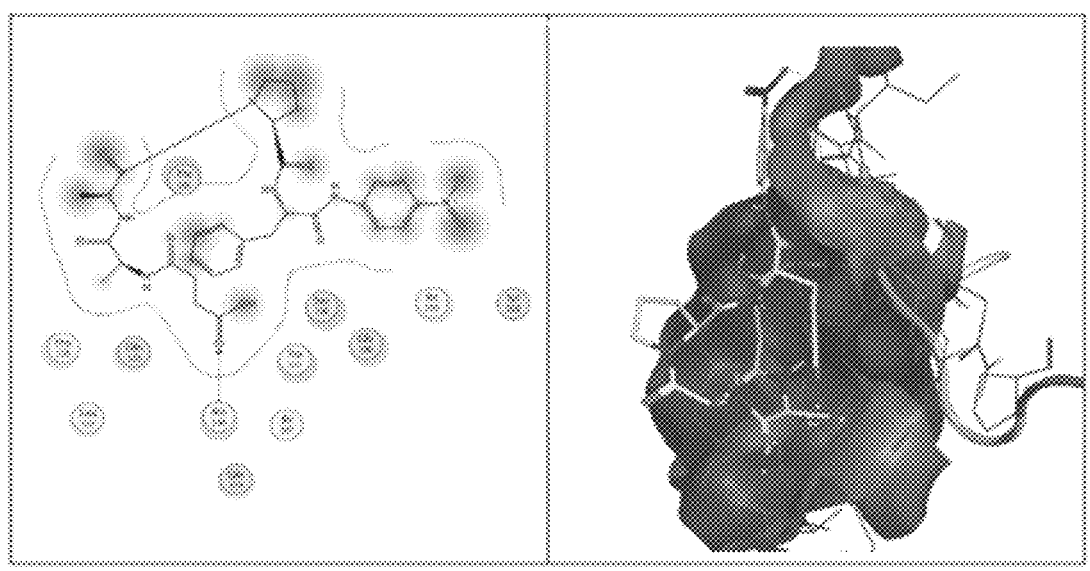

FIG. 13C. The 7 mutants keratinase ligand interaction: at left is the 2D structure and on right is the 3D structure. Ligand has one hydrogen bond with Ala 190.

Figure 14:
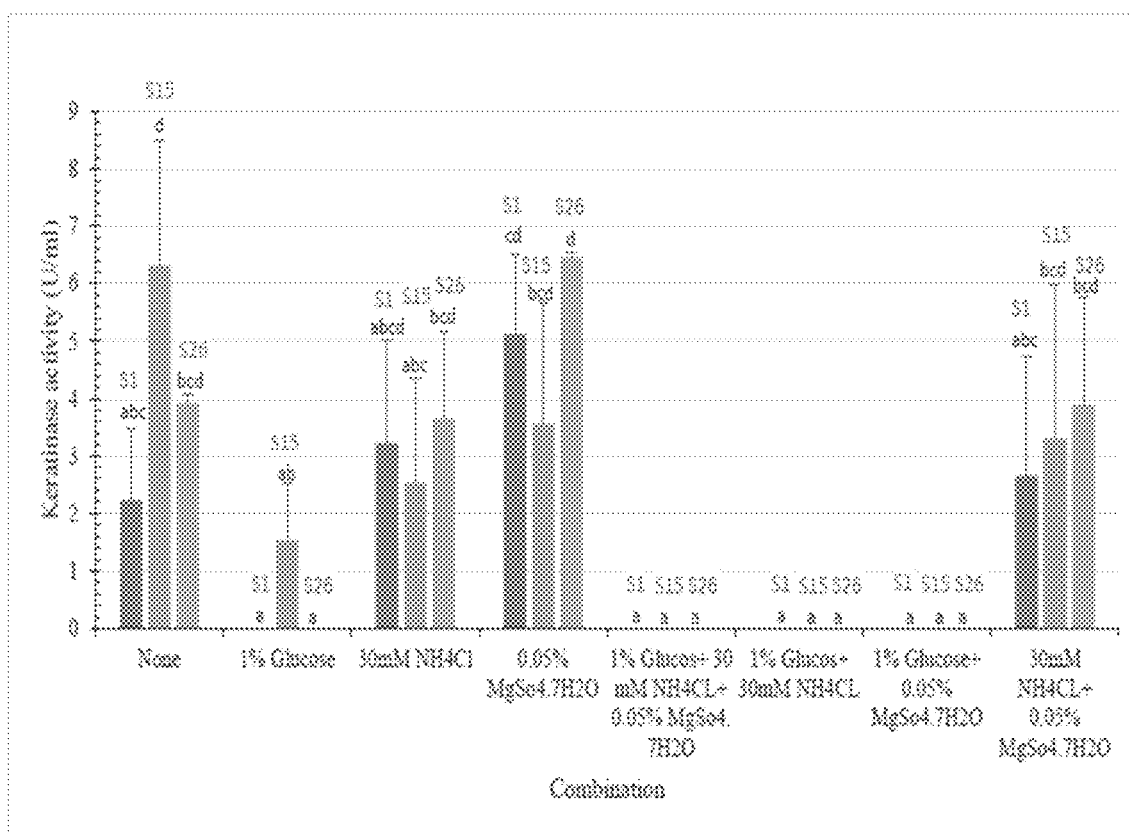
Figure 15A:
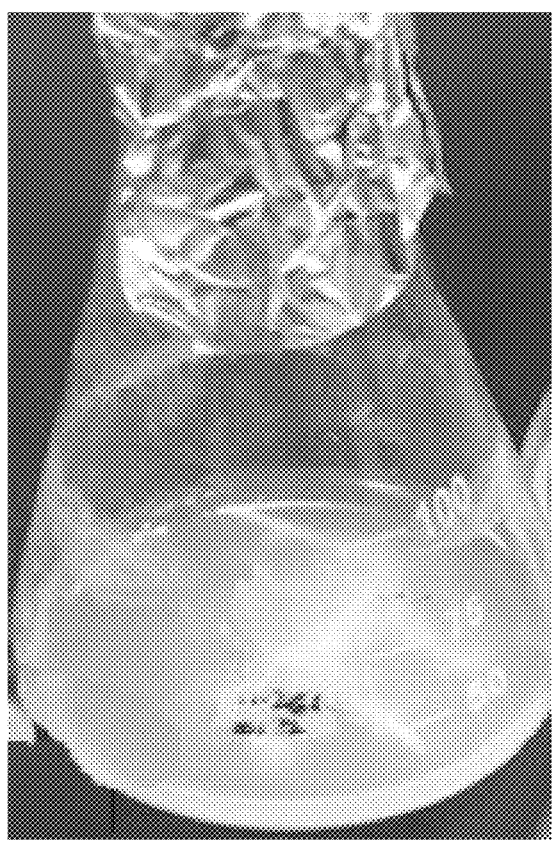
Figure 15B:
Figure 15C:
Figure 15D:
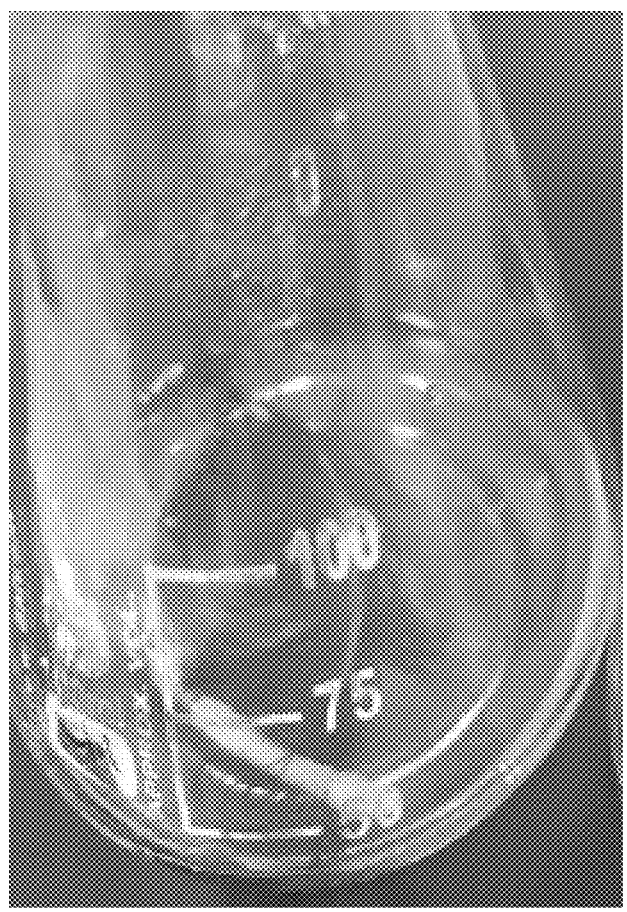
Figure 15E:
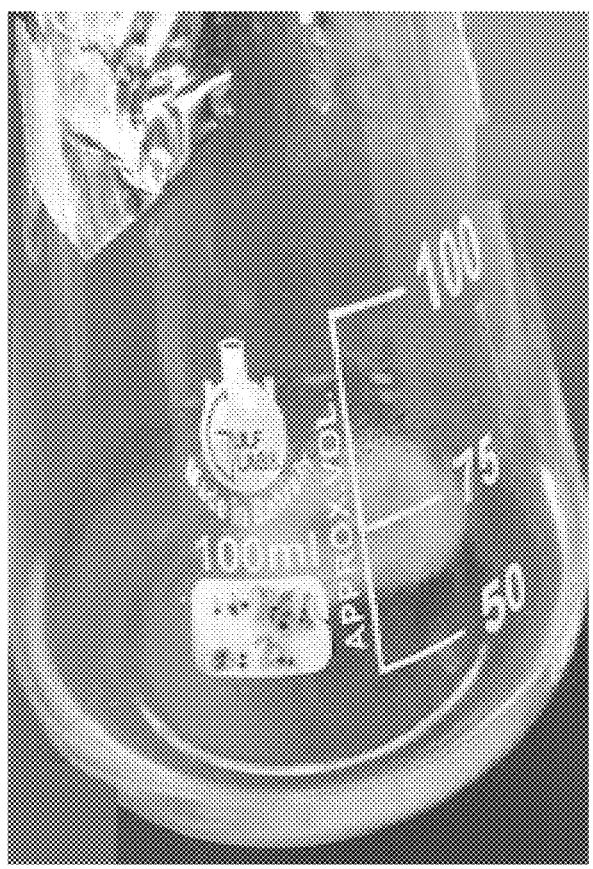
Figure 15F:
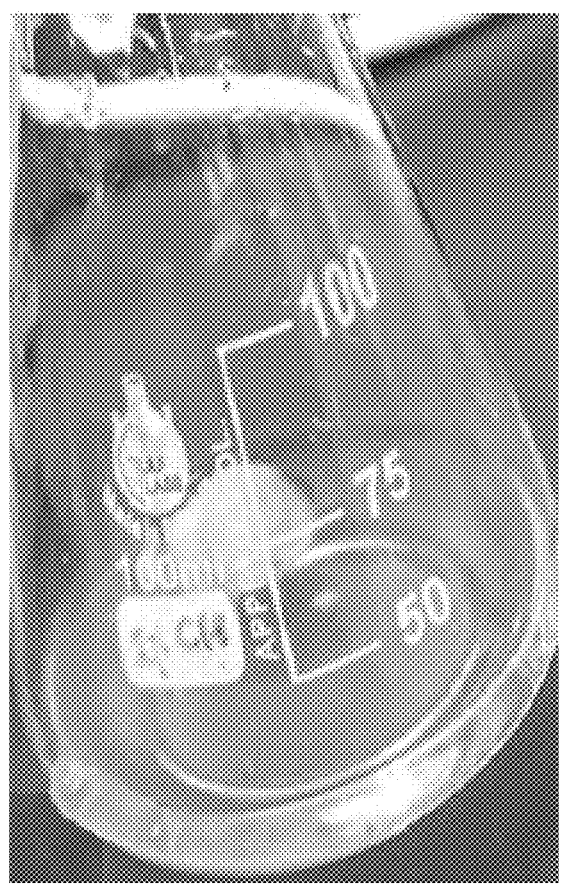
Figure 15G:
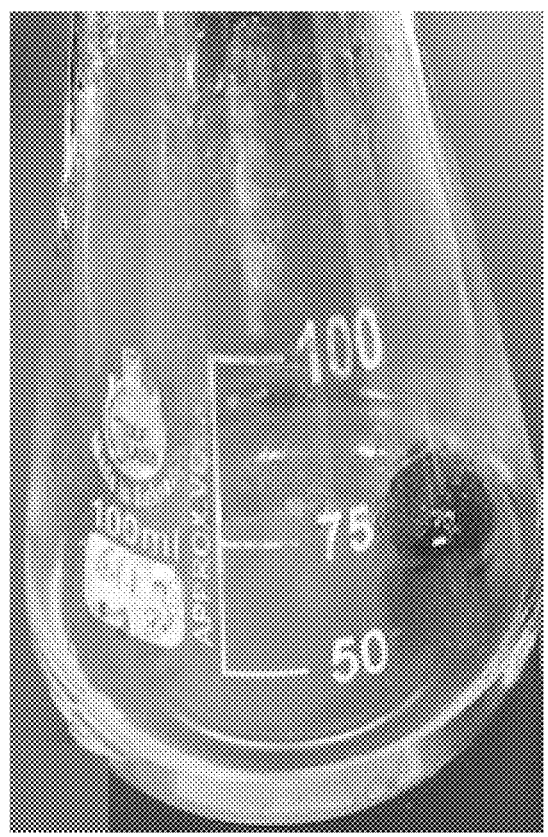
Figure 15H:
Figure 15I:
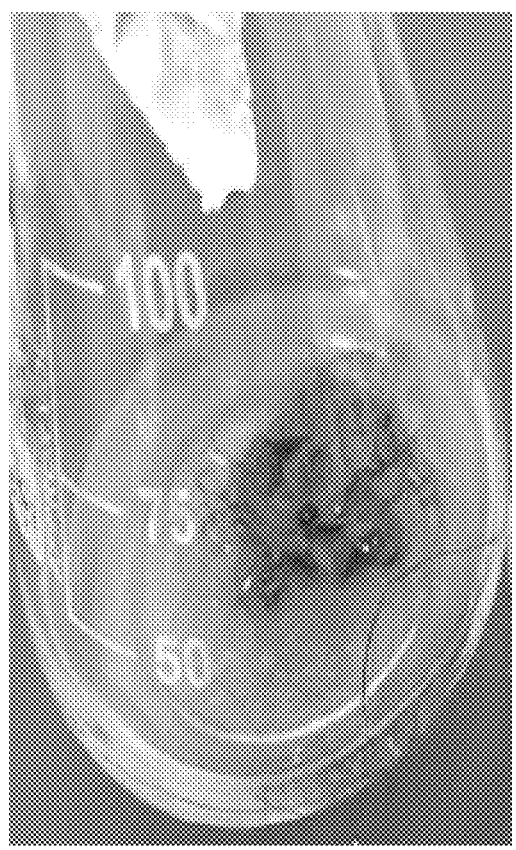
Figure 15J:
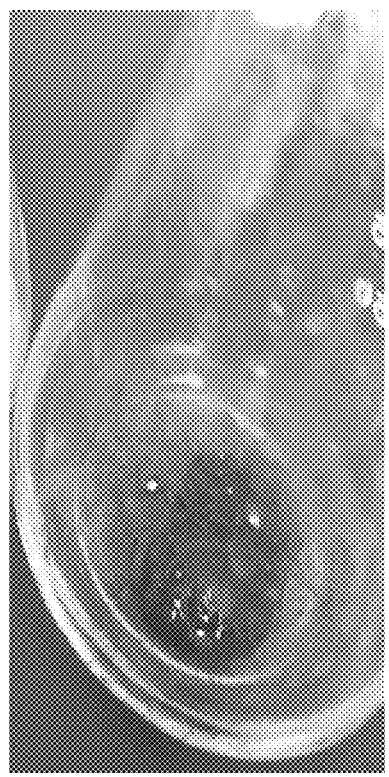

FIG. 14. Effect of Glucose, $NH_4Cl$, and $MgSO_4.7H_2O$ individually and in combination on keratinase activity of isolates S1, S15, and S26. This figure provides guidance as to which additives promote keratinase activity of S1, S15 and S26 strains. Means with different combinations of letters a, b, c, d are significantly different according to Duncan's multiple comparison test at $p<0.05$.

FIGS. 15A-15J. Influence of different keratin substrates-white chicken feather, black chicken feather, white sheep wool, black sheep wool and human hair—on keratinase production and chicken feather degradation after 72 h incubation at 45° C. (A) degradation of white chicken feather, (B) control, (C) degradation of black chicken feather, (D) control, (E) degradation of white sheep, (F) control, (G) degradation of black sheep wool. (H) control, (I) degradation of human hair and (J) control.

Figures 1, 16:
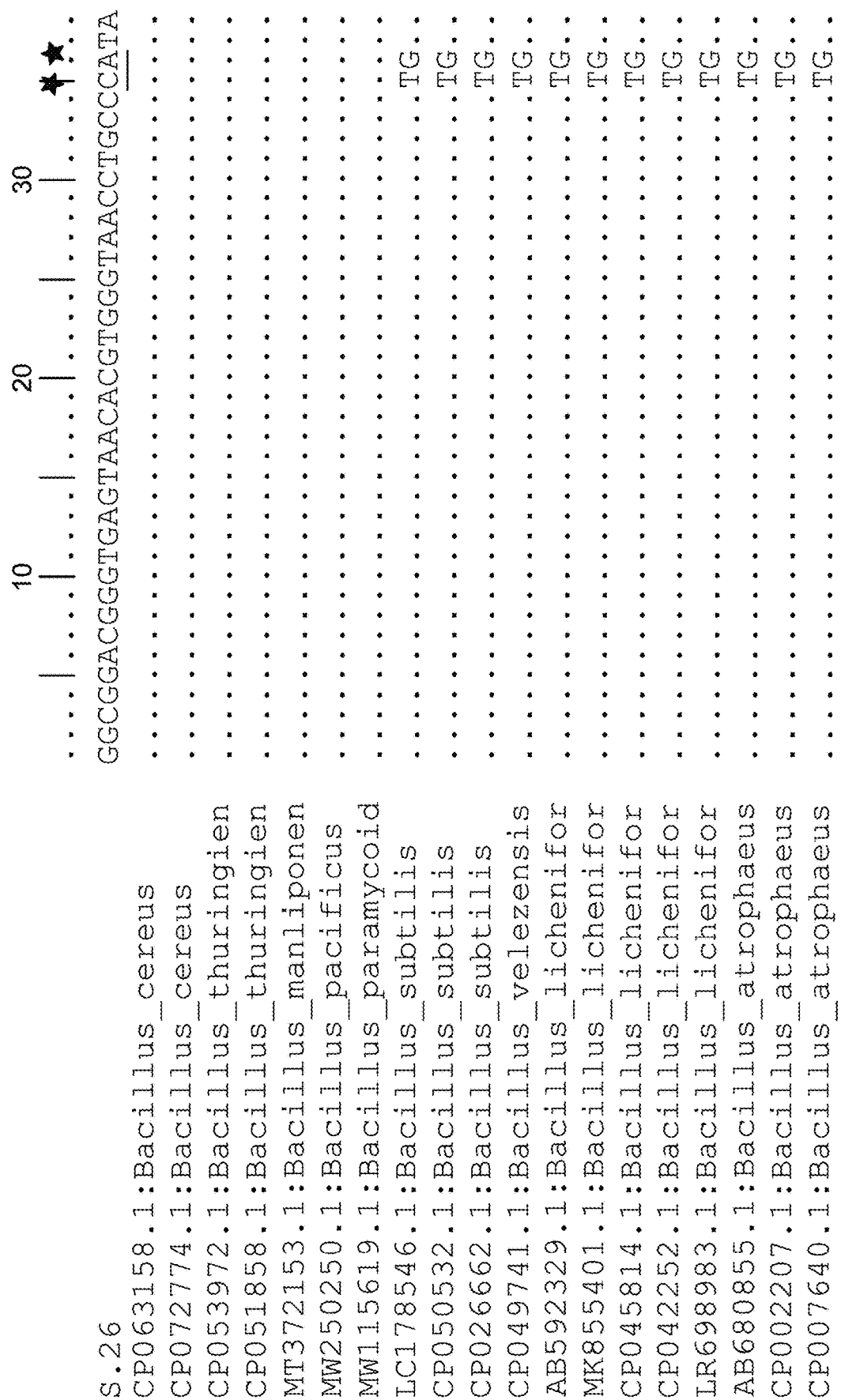
Figures 1, 16:
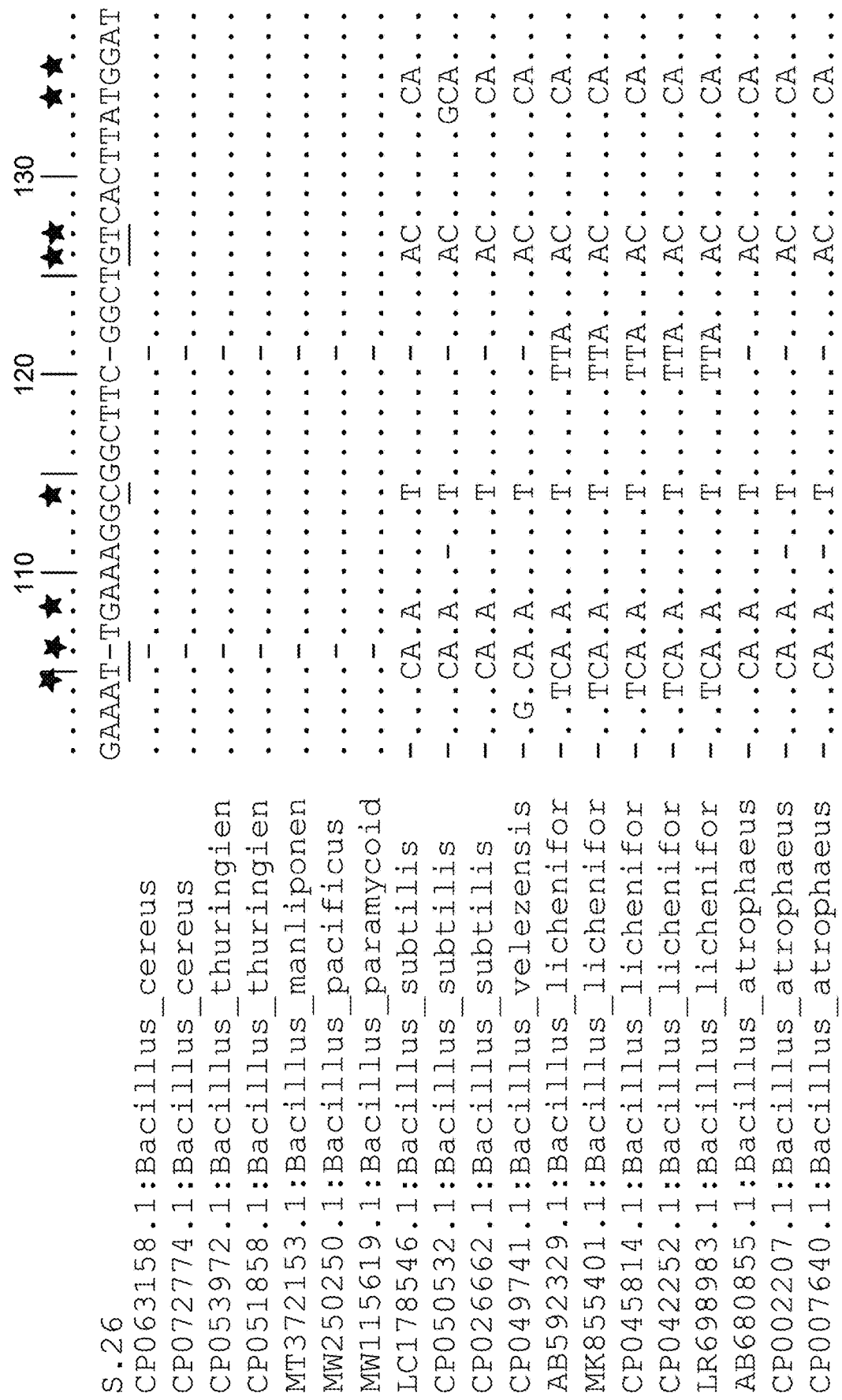
Figures 2, 16:
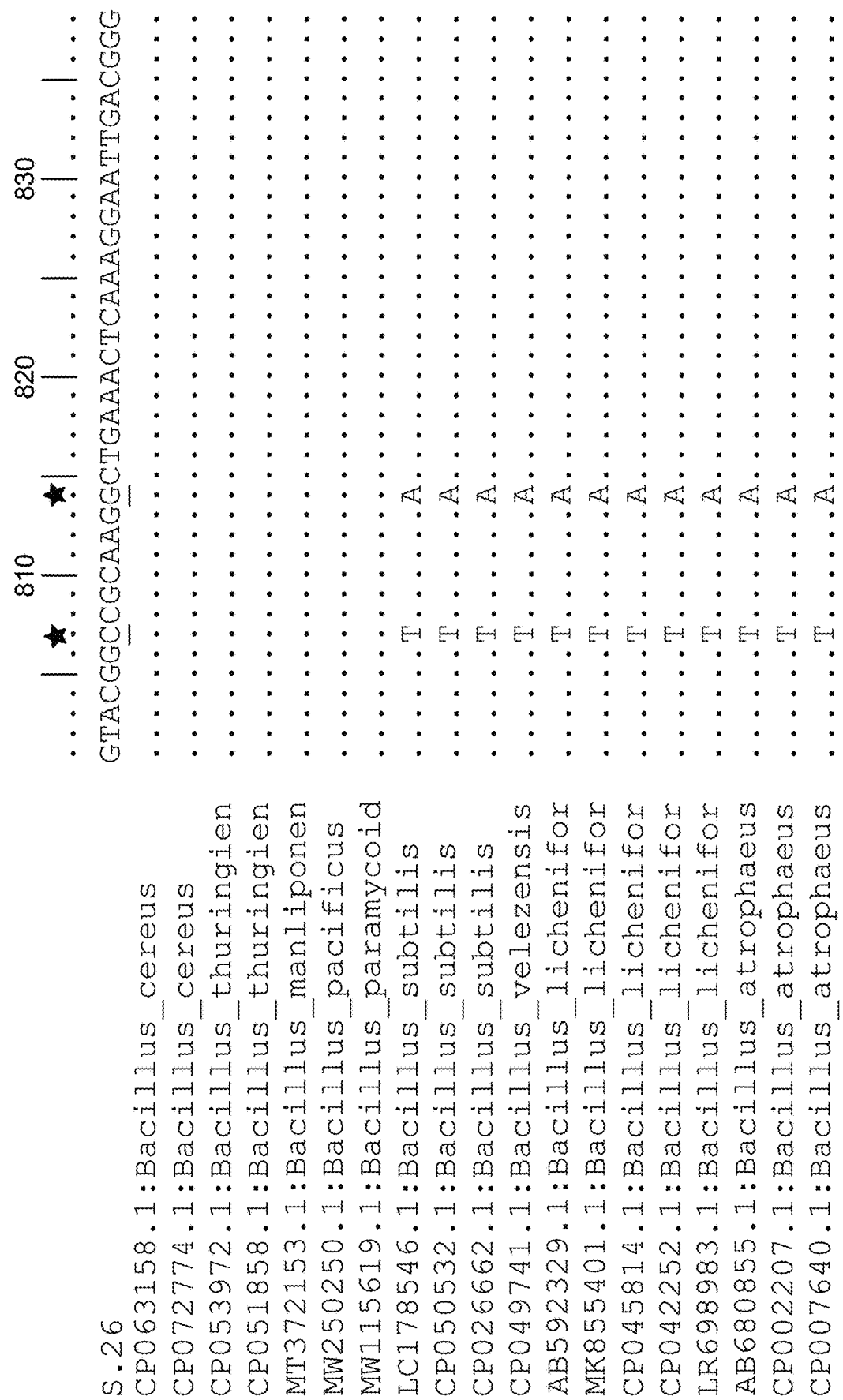

FIG. 16 (panels 16-1-16-3). Multiple sequence analysis of 16S rRNA gene, strain S26 (corresponded to SEQ ID NO: 8) against sequences retrieved from GenBank database. Stars correspond to the 58 major substitution positions differentiated between *B. subtilis* and *B. cereus* groups. Strain S26 is identical to *B. cereus* group sequences. The top nucleic acid sequence in panels 16-1 to 16-3 is described by SEQ ID NO: 8. The stars correspond to the 58 major substitution positions differentiated between *B. subtilis* and *B. cereus* groups. Strain S26 is identical to *B. cereus* group sequences. In some embodiments, 1, 2, 3, 4, 5, 6, 7, 8, 9, 10 or more mutations, or further mutations, are made to one or more substitution positions differentiated between *B. subtilis* and *B. cereus*, for example by substitution, deletion or insertion of one or more residues.

Figure 17:
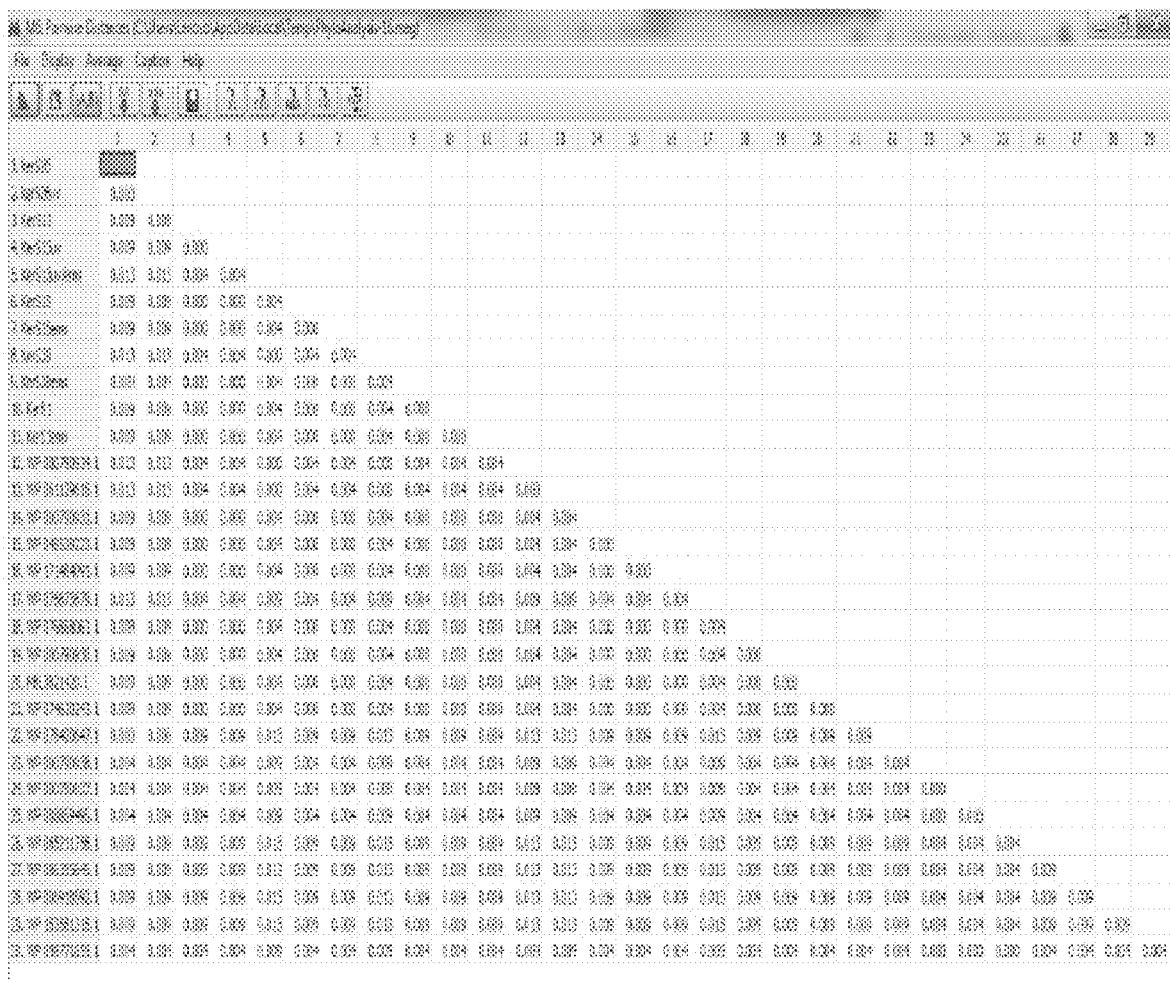

FIG. 17. Estimates of evolutionary divergence of KerS gene against S8 family peptidase, *Bacillus cereus* group sequences retrieved from GenBank database.

DETAILED DESCRIPTION OF THE INVENTION

Keratin is one of a family of structural fibrous proteins also known as scleroproteins. Alpha-keratin (α-keratin, contains alpha helices), beta-keratin (β-keratin, contains beta sheets) and gamma-keratin γ-keratin are types of keratin found in vertebrates. Keratins are key structural materials making up scales, hair, wool, nails, feathers, horns, claws, hooves, and the outer layer of skin among vertebrates. These keratin-containing materials are substrates for digestion, cleavage, or degradation by the keratinases disclosed herein. Keratin-Containing Materials.

The keratinous protein-containing material may be any protein material containing keratin, including but not limited to feathers, hair, wool, hide, bristles, horns, hooves, claws, nails, scales, or any other suitable keratinous protein-containing material or mixtures thereof. The keratinous protein-containing material may further comprise one or more hydrolysates, or partial hydrolysates of any keratinous protein-containing material. In some embodiments, the keratinous protein-containing material comprises raw feathers, hair or wool. In some embodiments, a keratin-containing material may be further hydrolyzed before or after contact with a keratinase by steam, other enzymes such as papain, chemical hydrolysis or combinations thereof.

Keratinase is proteolytic enzyme that digests keratin such as the keratins or keratin-containing materials described above. In some embodiments a keratinase is identified as a serine protease.

Keratinase Properties.

The term property or grammatical equivalents thereof in the context of a polypeptide, as used herein, refers to any characteristic or attribute of a polypeptide that can be selected or detected. These properties include, but are not limited to oxidative stability, substrate specificity, catalytic activity (e.g., on keratin), thermal stability, alkaline stability, pH activity profile, resistance to proteolytic degradation, $K_M$, $k_{cat}$, $k_{cat}/k_M$ ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and/or ability to treat disease, etc. The abovementioned keratinase's properties may be increased or decreased with respect to a reference, parent, or wild-type strain by a factor of 1.01, 1.02, 1.05, 1.1, 1.2, 1.3, 1.4, 1.5, 1.6, 1.7, 1.8, 1.9, 2.0 or >2.0.

Degrading Keratin.

As used herein the term "degrading" includes both chemical and structural (e.g., by denaturation) of keratin or a keratin-containing material. Degradation is a process by which a chemical substance like keratin, is broken down into smaller molecules. In some instances, a keratin-containing substance will be biotically degraded by action of a keratinase or a keratinase-producing microorganism. In other embodiments, a keratinase as disclosed herein may act in concert with abiotic degradation such as hydrolytic, photolytic or oxidative degradation. Half-lives may be used as measures of the stability and persistence of a chemical substance like keratin or keratin-containing material. Half-life is defined as the time it takes for an amount of a compound to be reduced by half through degradation. Biotic degradation or biodegradation is a process by which organic substances are broken down by enzymes or living organisms such as bacteria and fungi. Biodegradation can happen in surface water, sediment and soil. For example, feather wastes in soil may be biodegraded by introduction of a keratinase or a keratinase-produce microorganism. Degradation or persistence of a keratin-containing material may be determined by methods known in the art including by the testing guidelines described by, and incorporated by reference to, chemsafetypro.com/Topics/CRA/degradation.html #:~:text=Degradation % 20is %20the %20process %20by %20which %20a %20chemical,persistence %20of % 20a %20chemical %20substance %20 in %20the %20environment (last accessed Jul. 30, 2022) and oecd-ilibrary.org/environment/oecd-guidelines-for-the-testing-of-chemicals-section-3-degradation-and-accumulation_2074577x (last accessed Jul. 30, 2022). Degradation may comprise cleavage of disulfide bonds in keratin or in a keratin-containing material, as well as exoproteolysis or endoproteolysis of keratin or a keratin-containing material.

Thermostability.

The terms thermally stable and thermostable refer to proteases as disclosed herein that retain a specified amount of enzymatic activity after exposure to identified temperatures over a given period of time under conditions prevailing during the proteolytic, hydrolyzing, cleaning or other processes disclosed herein, for example, while exposed altered temperatures. Heat is often required in industrial applications to speed up reactions and spray drying processes used to produce keratinase powders can also require heating. Hence, a heat-stable keratinase can be very useful in many different applications.

Increased or decreased thermal stability may be determined by comparison to a reference keratinase, such as a keratinase produced by the unmodified parent strain or by an unmodified wild-type keratinase. A thermostable keratinase may retain keratinase activity at a reference temperature such as at 10, 15, 20, 25, 30, 35, 40, 45, 50, 60, 70 or >70° C. In some embodiments, the proteases retain at least about 50%, about 60%, about 70%, about 75%, about 80%, about 85%, about 90%, about 92%, about 95%, about 96%, about 97%, about 98%, or about 99% proteolytic activity after exposure to a reference temperature over a given time period, for example, at least about 30 minutes, 60 minutes, about 120 minutes, about 180 minutes, about 240 minutes, about 300 minutes, etc.

The term enhanced stability in the context of an oxidation, chelator, thermal and/or pH stable protease refers to a higher retained proteolytic activity over time as compared to other keratinases and/or wild-type enzymes, such as the parent protease from which an analog or mutant keratinase is derived. The term "diminished stability" in the context of an oxidation, chelator, thermal and/or pH stable protease refers to a lower retained proteolytic activity over time as compared to other keratinases and/or wild-type enzymes.

A wild-type sequence refers to a sequence that is native or naturally occurring in an unmodified cell or bacterium, such as a keratinase amino acid or polynucleotide sequence found in nature. A wild-type keratinase is often used as a reference keratinase for a modified wild-type keratinase, however, other non-wild-type keratinases may also be used as reference keratinases for particular properties of a keratinase.

A modification refers to any change or alteration in an amino acid sequence. It is intended that the term encompass substitutions, deletions, insertions, and/or replacement of amino acid side chains in an amino acid sequence of interest. It is also intended that the term encompass chemical modification of an amino acid sequence of interest or epigenetic modification of a nucleic acid sequence.

Keratinase Analogs.

The terms modified sequence, modified gene, or modified polypeptide are used interchangeably herein to refer to a sequence that includes a deletion, insertion or interruption of naturally occurring nucleic acid or amino acid sequence. In some preferred embodiments, the expression product of the modified sequence is a truncated or elongated gene, polynucleotide, polypeptide, or protein. This term may also refer to a substituted or chemically modified polynucleotide or polypeptide. Preferably, a modified polypeptide retains one or more of the biological activities of the unmodified polypeptide, such as retaining keratinase activity. Similarly, a modified gene or polynucleotide will retain the ability to express a functional polypeptide, such as one having keratinase activity.

In some instances, a modified polynucleotide will encode the same protein (e.g., keratinase), but with one or more synonymous codons encoding the same amino acid residue(s) as the unmodified polynucleotide: see hypertext transfer protocol secure://en.wikipedia.org/wiki/ Codon_usage_bias#Effect_on_transcription_or_gene_expression (last accessed Aug. 1, 2022) and by the references cited therein. For example, a polynucleotide encoding a keratinase may be modified to increase keratinase expression by enhancing translational capacity (e.g., by expressing the keratinase in a *Bacillus* strain with additional tRNAs or by modifying (RNA abundances, increasing mRNA stability, or by increasing or decreasing GC content; see the methods described by, and incorporated by reference to, Lipinszki, et al., *Enhancing translational capacity of E. coli by resolving codon bias*. ACS SYNTH. BIOL. 2018, 7, 2656-2664.

Analogs, including modified, mutant, variant, or engineered sequences, of the polynucleotides or polypeptides disclosed herein may have varying degrees of sequence identity or similarity to a wild-type or other reference polynucleotide or polypeptide. BLASTN may be used to identify a polynucleotide sequence having at least 75%, 80%, 85%, 87.5%, 90%, 92.5%, 95%, 97.5%, 98%, 99%, <100%, or 100% sequence identity to a reference polynucleotide such as a polynucleotide encoding a keratinase or serine protease. A representative BLASTN setting modified to find highly similar sequences uses an Expect Threshold of 10 and a Wordsize of 28, max matches in query range of 0, match/mismatch scores of 1/–2, and linear gap cost. Low complexity regions may be filtered or masked. Default settings of a Standard Nucleotide BLAST are described by and incorporated by reference to hypertext transfer protocol secure://blast.ncbi.nlm. nih.gov/Blast.cgi?PROGRAM=blastn&PAGE_TYPE=BlastSearch&LINK_LOC=blast-home (last accessed Jun. 7, 2022).

BLASTP can be used to identify an amino acid sequence having at least 75%, 80%, 85%, 87.5%, 90%, 92.5%, 95%, 97.5%. 98%, 99%, <100% or 100% sequence identity, or similarity to a reference amino acid sequence, such as a keratinase sequence, using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: hypertext transfer protocol secure://blast.ncbi.nlm.nih.gov/Blast.cgi?PROGRAM=blastp&PAGE_TYPE=BlastSearch&LINK_LOC=blasthome (last accessed Jun. 7, 2022).

Analogs of a polynucleotide or polypeptide may include those with 1, 2, 3, 4, 5, 6, 7, 8, 9, 10, 20, 30 or more deletions, substitutions, or insertions of nucleotides into a polynucleotide or polypeptide disclosed herein.

Surfactant refers to any compound generally recognized in the art as having surface active qualities. Surfactants generally include anionic, cationic, nonionic, and zwitterionic compounds, which are further described, herein. In some embodiments, the compositions described herein comprise a surfactant or surfactant system wherein the surfactant is selected from nonionic surfactants, anionic surfactants, cationic surfactants, ampholytic surfactants, zwitterionic surfactants, semi-polar nonionic surfactants and mixtures thereof. Surfactants can work in conjunction with the keratinases of the invention to unfold and degrade keratin and other components of a keratin-containing material, for example, a surfactant can remove oils and waxes on feathers thus better exposing keratin components to a keratinase.

Keratinases as Enzymatic Additives.

The present disclosure includes the use of the disclosed keratinases as enzymatic additives for clothing cleaning products. In some embodiments, additional enzymatic additives, such as those found in laundry detergents and other cleaning solutions may be present. The presence of keratinases is useful because animal hair is made primarily of alpha-keratin. Wool and some other fibers commonly used in clothing are therefore mostly alpha-keratin. Some beta-keratinases selectively degrade beta-keratin, while leaving alpha-keratin largely intact. Beta-keratinases can therefore be particularly useful as enzymatic cleaners for woolen products and some other clothing fabrics. While the addition of protein-degrading enzymes to cleaning products is known, clothing fibers which are made of proteins tend to be degraded by the same enzymes. In particular, many natural fibers, especially wool and silk, are difficult to clean completely since cleaning products capable of removing difficult stains such as blood and vegetable dyes also attack the fabric. This can lead to a weakening of the fabric. If an enzyme can specifically degrade the material of the stain, while leaving the stained material intact, this can produce a cleaner that is mild but still very effective. Enzymatic cleaning products including beta-keratinases are effective in removing protein stains from clothing fibers composed of alpha-keratin but are less likely than other proteases to weaken the fabric. Silk is composed of keratin (but not of alpha-keratin), and the keratinases of the invention may be useful as enzymatic cleaners for silk as well. Beta-keratinases may also be useful in hard surface cleaners and personal care products.

The keratin-biodegradation ability and keratinase activity by S1, S15 and S26 using different keratin substrates (i.e., white chicken feather, black chicken feather, white sheep wool, black sheep wool, and human hair) were studied. The inventors observed significant partial degradation of white sheep wool, black chicken feather, black sheep wool indicates the ability of the disclosed isolates to degrade both α-keratin and β-keratin.

Feather and Fowl Waste Disposal.

Enzymes disclosed herein are useful in commercial composting involving degradation of keratin and other proteins. One waste disposal problem of commercial poultry farms is that of disposing of dead birds. Many such birds are buried or burned. However, due to the natural resistance of keratin to biological degradation, feathers often remain after the soft tissues of the birds have decomposed. Collagen and elastin are also found in birds, and are also somewhat resistant to degradation. Collagen and elastin also tend to remain after the decomposition of soft tissues. Other wastes from poultry processing, such as poultry manure, often contain significant amounts of difficult-to-degrade feathers. The present technology includes a method for degrading the keratin found in dead birds and other poultry waste by composting. A bacterial strain, such as *B. cereus* strains and mutants disclosed herein is added to a composter, preferably along with poultry manure, straw, water, and dead chickens. Such a strain may also be sprayed or otherwise applied to areas such as those inside or outside of a chicken coop containing poultry wastes. In some embodiments, microorganisms that produce collagenase or elastase, or isolated forms of these enzymes, may be used in conjunction with the keratinase disclosed herein, such enzymes are described by, and incorporated by reference to hypertext transfer protocol secure://en.wikipedia.org/wiki/Elastase and to hypertext transfer protocol secure://en.wikipedia.org/wiki/Collagenase (last accessed Aug. 2, 2022).

Unless otherwise indicated, the practice of the present technology involves conventional techniques commonly used in molecular biology, protein engineering, mutagenesis, microbiology, and recombinant DNA, which are within the skill of the art. Such techniques are known to those of skill in the art and are described in numerous texts and reference works: see e.g. Sambrook et al., *Molecular Cloning: A Laboratory Manual*, Second Edition (Cold Spring Harbor), [1989]); and Ausubel et al., *Current protocols in Molecular Biology*, Volumes 1 and 2. John Wiley & Sons, Inc., Media, P A, 1988.

EXAMPLES

Conventional keratinases lack suitable characteristics for treating fibrous feather material on a large scale. Accordingly, the inventors' efforts were directed towards identifying and modifying new bacterial strains expressing more efficient or broader spectrum keratinases, assessment of their enzymatic (keratinolytic) activity, and design and engineering of keratinases sought to screen, isolate, and identify efficient keratinolytic bacterial isolates, as well as to increase keratinase production through physical and chemical mutagenesis. In part, keratinolytic bacteria and their keratinase were identified in silico and keratinase sequence and structure analysis were used to determine the effect of mutagenic treatments on keratinase genes.

In silico analysis was used to identify different prospective bacterial keratinases. Techniques of in silico analysis are described by, and incorporated by reference to, Jaouadi, N. Z. et al., Biochemical and molecular characterization of a serine keratinase from Brevibacillus brevis US575 with promising keratin-biodegradation and hide-dehairing activities. PLOS ONE 2013, 8, e76722; Tang, Y. et al., A novel thermostable keratinase from Deinococcus geothermalis with potential application in feather degradation. APPL. SCI. 2021, 11, 3136; Fellahi, S. et al., Identification of two new keratinolytic protease from a Bacillus pumilus strain using protein analysis and gene sequencing. AMB EXPRESS 2016, 6, 42.

Chemical mutations using ethyl methanesulfonate (EMS) and gamma ray mutagenesis are described by, and incorporated by reference to, De Paiva, D. P. et al., Keratinolytic activity of Bacillus subtilis LFB-FIOCRUZ 1266 enhanced by whole-cell mutagenesis. 3 BIOTECH 2019, 9, 2; Kothari, D. et al., In Current Developments in Biotechnology and Bioengineering. Production, Isolation and Purification of Industrial Products; Pandey, A., Negi, S., Soccol, C., Eds.; Elsevier: Oxford, U K, 2017; pp. 447-469; Isiaka, A. et al., Keratinases: Emerging trends in production and applications as novel multifunctional biocatalysts. KUWAIT J. SCI. 2016, 43, 118-127.

As described by the inventors below, five keratinolytic bacteria were isolated from poultry farm waste of Eastern Province. Saudi Arabia. The highest keratinase activity of these keratinases was obtained at 40-45° C., pH 8-9, feather concentration 0.5-1%, and using white chicken feather as keratin substrate for 72 h.

Enhancement of keratinase activity through physical mutagen UV radiation and/or chemical mutagen ethyl methanesulfonate (EMS) resulted in five mutants with 1.51-3.73-fold increased activity over the wild type. When compared with the wild type, scanning electron microscopy validated the mutants' effectiveness in feather degradation. Bacterial isolates are classified as members of the S8 family peptidase *Bacillus cereus* group based on sequence analysis of the 16S rRNA and keratinase genes. Interestingly, keratinase KerS gene shared 95.5-100% identity to keratinase, thermitase alkaline serine protease, and thermophilic serine protease of the *B. cereus* group.

$D_{137}N$ substitution was observed in the keratinase KerS gene of the mutant strain S13 (KerS13uv+ems), and also seven substitution variations in KerS26 and KerS26uv of strain S26 and its mutant S26uv.

Functional analysis revealed that the subtilisin-like serine protease domain containing the Asp/His/Ser catalytic triad of KerS gene was not affected by the predicted substitutions. Prediction of physicochemical properties of KerS gene showed instability index between 17.5-19.3 and aliphatic index between 74.7-75.7, which imply keratinase stability and significant thermostability.

The docking studies revealed the impact of substitutions on the superimposed structure and an increase in binding of mutant $D_{137}N$ of KerS13uv+ems (affinity: −7.17; S score: −6.54 kcal/mol) and seven mutants of KerS26uv (affinity: −7.43; S score: −7.17 kcal/mol) compared to the wild predicted structure (affinity: −6.57; S score: −6.68 kcal/mol). Together, the keratinolytic activity, similarity to thermostable keratinases, and binding affinity suggest that keratinases KerS13uv+ems and KerS26uv could be used for feather processing in the industry.

Materials and Methods.

Bacterial Isolation, Screening for the Keratinolytic Activity, and Keratinase Assay Samples of poultry farm wastes, feathers, and soil were collected from a soil depth of 5-4 cm from several poultry farms located in Dammam city, AL-Qatif city, Al-Ahsa city, and Al-Jubail city, Eastern Province, Saudi Arabia.

Bacterial isolation was carried out according to Subugade et al. *Isolation and Screening of Keratinase Producing Bacteria from Chicken Feather Dumping Site*. Int. J. ChemTech Res. 2017, 10, 900-905. Bacterial isolates from feathers were isolated by plating a portion of the feathers on a nutrient agar medium. The soil bacteria were isolated by serial dilution up to $10^{-3}$. Plates were incubated at 30° C. for 24 h. The bacterial isolates were further subcultured to obtain a pure culture. The purity of the gram-stained bacteria was observed under a high-power magnifying lens (100) in alight microscope; see Subugade S. et al. Subugade et al. *Isolation and Screening of Keratinase Producing Bacteria from Chicken Feather Dumping Site. Int.* J. ChemTech Res. 2017, 10, 900-905.]. The bacterial isolates were maintained on nutrient agar slants and stored at 4° C.

Screening for proteolytic activity was carried out according to Reyes et al. using the following medium: 5 g/L peptone, 3 g/L yeast extract, 100 mL/L sterile non-fat milk, and 20 g/L agar; Reyes, A. et al., *Isolation and characterization of keratinolytic bacteria from soil samples of poultry waste dumping sites*. Int. J. Agric. Technol. 2018, 14, 1787-1800. Bacteria were incubated at 30° C. for 72 h. Isolates that depicted the highest hydrolytic zone of clearance around colonies in this medium were selected. The processing of feathers was carried out according to Rajak et al.; Rajak, R. C. et al., *Keratinolysis by Absidia cylindrospora and Rhizomucor pusillus: Biochemical proof.* Mycopathologia 1992, 118, 109-114. White chicken feathers were washed with warm water and detergent, followed by defatting and surface sterilized with petroleum-ether aliquots for over 24 h. Finally, they were washed with distilled water and dried in an oven at 50° C. for 24 h.

The method of Aly, M. M. et al., *Isolation, identification, and characterization of a keratolytic bacterium from poultry wastes.* IOSR J. PHARM. BIOL. SCI. 2019, 14, 46-50, was used to evaluate the keratinolytic properties of the tested bacteria as follows: one hundred ml Erlenmeyer flasks containing 50 mg washed defatted white chicken feathers in 20 mL growth basal salt medium composed of (g/L) $NH_4Cl$ 0.5 g; NaCl 0.5 g; $KH_2PO_4$ 0.3 g; $K_2HPO_4$ 0.3 g; yeast extract 0.1 g; $MgCl_2.6H_2O$, 0.1 g and pH was adjusted to 7. The autoclaved medium was inoculated with 1 mL bacterial cell suspension (1 mL of 24 h old bacterial suspension grown in 5 mL of the nutrient broth medium at 30° C.). The cultures were incubated at 37° C. under shaking at 270 rpm for 72 h. Keratinase activity of culture filtrate was assayed using a modified protocol of Preczeski, K. P. et al., *Fusarium oxysporum and Aspergillus Sp. as keratinase producers using swine hair from agroindustrial residues.* FRONT. BIOENG. BIOTECHNOL. 2020, 8, 71, with keratin azure as a substrate. The reaction mixture contained 0.4 mL of crude enzymes and 1.6 mL of 0.4% keratin azure (Sigma K8500, Saint Louis, MI, USA) in 10 mM tris HCl (pH 8.5) buffer incubated at 50° C. for 1 h. Subsequently, the reaction was stopped with 0.8 mL of 10% trichloroacetic acid (TCA) then centrifuged at 5000 rpm for 20 min. A control sample was prepared in a similar manner except that the bacteria were replaced by the same volume of $dH_2O$. Unit of keratinase activity was defined as a 0.01 unit increase in absorbance at 595 nm.

Factors Affecting Keratinase Activity.

The effect of the incubation period on keratinase activity was determined according to Dhiva, S. et al., Optimization of keratinase production using Pseudomonas aeruginosa Su-1 having feather as substrate. BIOINTERFACE RES. APPL. CHEM. 2020, 10, 6540-6549. Incubation period effects on enzyme activity were determined at 24 h intervals at 45° C. during an incubation period of 24-96 h at initial pH 7.

The effect of temperature on enzyme activity was analyzed in a varied temperature range (35° C., 40° C., 45° C., 50° C., and 55° C.) at initial pH 7; Aly, M. M. et al., supra.

The effect of the initial pH of the medium on keratinase activity was determined according to Aly et al., supra, pH effects on the enzymatic activity were analyzed at 45° C. at varied initial pH values ranging from 6 to 9.

According to Kalaikumari et al., supra, the effect of supplementation of additional nitrogen source ($NH_4Cl$), carbon source (glucose), and sulfur source ($MgSO_4$ $7H_2O$) individually and in combination with white chicken feathers on the keratinase activity was determined at initial pH 7.5 and 45° C.

Moreover, the impact of white chicken feather concentrations on the enzymatic activity was assessed at 45° C. in a varied feathers concentration range (0.5%, 1%, 1.5%), and 2% at initial pH 7.5; see Kalaikumari, S., et al., supra.

Feather Biodegradation In Vitro.

The influence of keratin substrate on the enzymatic activity was investigated at 45° C. in a varied keratinaceous material (i.e. white chicken feather, black chicken feather, white sheep wool, black sheep wool, and hair) as carbon and energy source at initial pH 8; see Dagnaw, M. et al., *Solid state fermentation of keratinolytic protease production using Bacillus Spp. isolated from water of leather processing ponds in North Gondar, Ethiopia.* BIOTECHNOL. INT. 2019, 7, 127-138.

Random Mutagenesis.

UV-induced mutagenesis was performed according to Aly and Tork, Aly, M. M. et al., *High Keratinase production and keratin degradation by a mutant strain KR II, derived from Streptomyces radiopugnans KR 12.* ARTIC. J. APPL. BIOL. SCI. 2018, 12, 18-25. The wild-type bacteria (S1, S13, S15, S26, and S39) were cultured on nutrient agar plates at 30° C. for 24 h, then exposed to UV irradiation at 254 nm and 365 nm for 10 min, 20 min, and 30 min at distances of 10 cm and 20 cm from the UV lamp. Plates were incubated overnight at 30° C. The keratinolytic activity of the mutant isolates was evaluated using skim milk plates as well as the previously described basal salt medium.

Ethyl methanesulfonate (EMS)-induced mutagenesis study was carried out according to the method of de Paiva et al. supra. Wild bacterial isolates (S1, S13, S15, S26, and S39), and UV mutated isolates (S13uv and S26uv) were grown in 5 mL of nutrient broth medium at 30° C. for 24 h; after that, 1% of EMS was added and incubated at 30° C. for 2 h. Cells were then centrifuged at 5000 rpm for 7 min, washed twice with sterile distilled water and the pellet was resuspended in 5 mL of nutrient broth medium and incubated at 30° C. for 1 h. Successive serial dilutions were prepared up to $10^{-3}$ and 0.1 mL of the bacterial dilutions were spread on a nutrient agar medium. The keratinolytic activity of the mutant isolates was tested using skim milk plates as well as the previously described basal salt medium.

Evaluation of Biodegradation Efficiency of the Wild and Mutant Isolates by Scanning Electron Microscopy.

To check for keratinase activity, the structural changes of biodegraded feathers were examined by scan electron microscopy (SEM) as described by Gupta and Singh; see Gupta, S. et al., *Hydrolyzing proficiency of keratinases in feather degradation.* INDIAN J. MICROBOL. 2014, 54, 466-470. Degraded chicken feathers after 72 h of incubation with keratinolytic bacterial isolates S13, and S39, and their mutants were recovered and oven-dried at 50° C. After slicing into 1 cm, the samples were sterilized with 70% ethanol for 10 min, then fixed with 2.5% glutaraldehyde for 4 hand washed with distilled $H_2O$ for 5 min. Samples were dehydrated by a series of ethanol (30%, 50%, 70%, 90%, and 100% for 10 min) at room temperature, followed by critical point drying. Later, feathers samples were sputter-coated with gold and observed by SEM (FEI, Inspect S50, Brno, Czech Republic) at an accelerating voltage of 20 kV.

Feather Hydrolysis Assay.

The degree of feather hydrolysis by the tested bacteria was assessed according to the weight-loss method of Nnolim, N. E. et al., *Bacillus Sp. FPF-1 Produced keratinase with high potential for chicken feather degradation.* MOLECULES 2020, 25, 1505. The fermentation broth was filtered (Whatman® qualitative filter paper, Grade 1, Maidstone, UK) to recover undegraded feathers, and oven dried at 50° C. for 24 h, and the constant weight was achieved. The degree of feather hydrolysis was calculated as shown in Equation (1):

$$\% \text{ of hydrolysis} = \left(\frac{IM - FM}{IM}\right) \times 100 \quad (1)$$

where, (IM) is the initial dry mass of the intact feather before the fermentation process, and (FM) is the dry mass of the residual feather after the fermentation process.

Statistical Analysis.

All In vitro experiments were performed in duplicate. Data obtained were analyzed by ANOVA test and means were compared by Duncan's (SPSS 22.0 version). Differences were considered significant when $p<0.05$. Values are expressed as means standard error (SE). Mean with the different letters are significantly different; see Gumilar, J. et al., *Isolation, identification and dehairing activity of indonesian native keratinolytic bacteria Exiguobacterium Sp. DG*1. Pak. J. BIOTECHNOL. 2015, 12, 41-48.

PCR Amplification of 16 rRNA and Keratinase Genes.

The 16S rRNA gene of the keratinolytic isolates (S1, S13, S15, S26, and S39) was amplified using colony PCR and the following primers: Forward 5'-AGAGTTT-GATCCTGGCTCA G-3' (SEQ ID NO: 1) and reverse 5'-TACGGCTACCTTGTTACGACTT-3' (SEQ ID NO: 2), (AppliedBiosystems, Foster City, CA, USA). The PCR reaction was carried out using PCR master mix (MOLEQULE-ON, Auckland, New Zealand) in Biometra T-Professional thermocycler (Biometra, Goettingen, Germany) with an annealing temperature of 56° C. for 35 cycles; see AlJindan, R. et al., *Diagnostic Deficiencies of C. difficile Infection among Patients in a Tertiary Hospital in Saudi Arabia: A Laboratory-Based Case Series*. SAUDI J. BIOL. SCI. 2021, 28, 4472-4477.

Keratinase (KerS) gene was amplified from wild-type isolates (S1, S13, S15, S26, and S39) and their mutants (S1ems, S13uv, S13uv+ems, S15ems, S26uv, and S39ems). Bacterial colonies were used for direct amplification of the keratinase gene. Keratinase primers were designed using *Bacillus cereus* strain BHU2 chromosome (CP023726.1): BaCeKerF 5'ATYGAGAATCCATATGTAG-GAAAATTAG-3' (SEQ ID NO: 3) and BaCeKerR 5'CATCCCCTCTTTACTTWATTACTATCAT-3' (SEQ ID NO: 4) for the amplification of the entire gene (1660 bp).

PCR amplification of KerS gene was performed using PCR master mix (MOLEQULE-ON, Auckland, New Zealand) in Biometra T-Professional thermocycler (Biometra; Goettingen, Germany) with the annealing temperature at 54° C. for 35 cycles. The PCR amplicons were visualized using 2% agarose gel electrophoresis and purified using QIAquick PCR Purification Kit (Qiagen, Hilden, Germany). The purified products of 16S rRNA and keratinase genes were sequenced with the same forward reverse primers using 3500 genetic analyzers (Applied Biosystems, Foster City, CA, USA) through BigDye® Terminator v3.1 Cycle Sequencing Kit (Applied Biosystems, Foster City, CA, USA).

Sequence Similarity Search and GenBank Submission.

Sequences were checked and edited using FinchTV (hypertext transfer protocol secure://finchtv.software.informer-.com/1.4/. accessed on 20 Dec. 2021). The sequence was analyzed using the BLAST program (hypertext transfer protocol/twww.ncbi.nlm.nih.gov/blast. accessed on 20 Dec. 2021). Sequences were submitted to GenBank (hypertext transfer protocol secure://www-ncbi-nlm-nih-gov.library.iau.edu.sa/WebSub/, accessed on 20 Dec. 2021) under the accession numbers OL441832-OL441836 and OL448296-OL448306 for the 16S rRNA and keratinase gene sequences, respectively, which are incorporated by reference.

Phylogenetic Analysis of 16S rRNA and Keratinase Genes.

For sequence comparison, 16SrRNA and keratinase sequences were retrieved from the National Center for Biotechnology Information (NCBI) database (hypertext transfer protocol://www.ncbi.nlm.nih.gov, accessed on 20 Dec. 2021). Sequence alignment analysis and phylogenetic tree construction were performed by MEGA 6.0.

Functional Analysis of Keratinase Gene.

Expasy-PROSITE tools are protein databases for identifying protein domains, families, and functional sites as well as associated patterns and profiles; see Sigrist. C. J. et al., *New and continuing developments at PROSITE*. NUCLEIC ACIDS RES. 2013, 41, 344-347. ScanProsite, one of the Expasy-PROSITE tools, was used to predict the catalytic domain and the active sites of the KerS gene.

Physicochemical Characterization of Keratinase Gene.

The physical and chemical attributes, such as molecular weight, theoretical isoelectric point (pI), amino acid composition, instability index, aliphatic index, and grand average of hydropathy (GRAVY) were computed using the ProtParam assessment tool of the ExPASy server (hypertext transfer protocol://web.expasy.org/protparam/, accessed on 20 Dec. 2021, incorporated by reference).

Structure Modeling and Analysis of Wild-Ape Keratinase and Mutants.

The Swiss MODEL server was used to predict the structural modeling of keratinase KerS protein, and to create mutated keratinase, KerS13uv+ems ($D_{137}N$), and the 7 substitutions ($N_{117}K$, $V_{195}I$, $A290G$, $S_{295}L$, $R_{297}K$, $T_{364}S$, and $S_{368}T$) that differentiated between KerS26uv and the other 4 keratinase strains. Visualization of the modeled PDB was done using PYMOL and validated using PROCHECK. Ramachandran plot statistics using the PDBsum structural analysis server were used to validate the 3D models.

The suitable model for keratinase protein was selected based on the criteria of having the highest number of amino acid residues in the most favored region and the minimum number of residues in the outlier region, and the same was used for further analysis. In the validated model, 3D atomic coordinates of the receptor were used to verify potential sites for binding of substrate docking; see Abdul Azeez, S. et al., *State-of-the-art tools to identify druggable protein ligand of SARS-CoV-*2. ARCH. MED. SCI. 2020, 16, 497-507; Microorganisms 2022, 10, 93 26 of 27.

Molecular Docking Study of Keratinase KerS Gene.

Docking of the keratinase protein modeled structures of wild and mutant types was performed separately with N-succinyl-L-alanyl-L-alanyl-L-prolyl-L-phenylalanine 4-nitroanilide (S-9205) as a substrate to analyze the substrate specificity and analyze active sites. The modeled structures were 3D protonated, and then docking was performed with the selected ligand N-succinyl-L-alanyl-L-alanyl-L-prolyl-L-phenylalanine 4-nitroanilide. The settings of MOE software were rescoring 1 at London dG and rescoring 2 at GBVI/WSA dG, and the ligand interaction was performed with keratinase protein. Energy minimization was performed for both ligands and proteins; Abdul Azeez, S. et al., supra.

Isolation and Screening of Keratinolytic Bacteria.

Figure 1A:
FIGS. 1A-1D show bacterial isolates of keratinolytic bacteria. Bars in FIGS. 2A-2D show the standard error of the mean. Means with different combinations of letters a, b, c, d are significantly different according to Duncan's multiple comparison test at p<0.05.
Figure 1B:
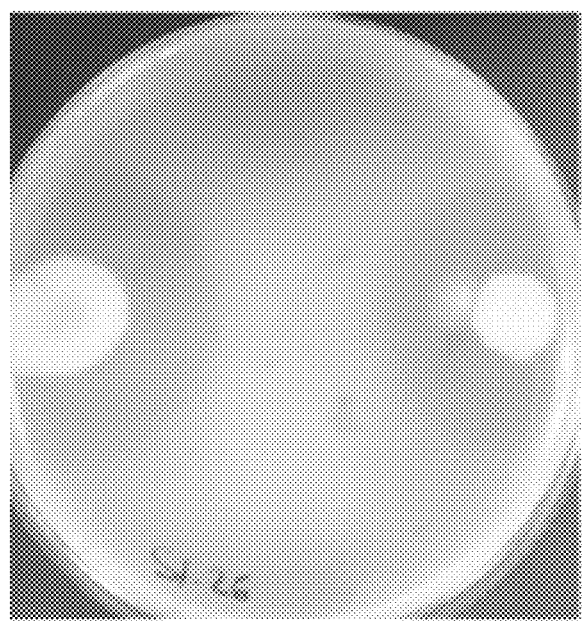
Figure 1C:
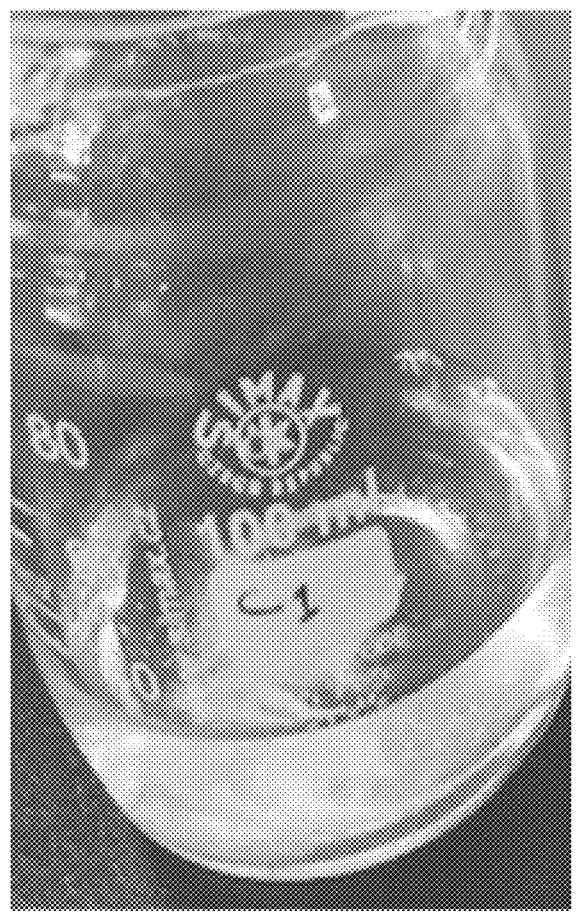
Figure 1D:

A total of 42 bacterial isolates were isolated from different samples of poultry farm waste, in Eastern Province, Saudi Arabia. Based on the bacterial shape observed under the light microscope, microscopic examination of the new isolates revealed that the cells were rod-shaped, straight, occurring singly, in pairs, or chains. and gram-positive; 18 isolates were considered pure and chosen for further study, see for example FIG. 1A. Upon preliminary screening, the eighteen isolates showed proteolytic activity, forming a remarkable hydrolytic zone of clearance (20-38.5 mm) around their colonies confirming the degradation and utilization of skim milk (FIG. 11B). Five of the high clearance zone isolates (S1, S13, S15, S26, and S39) were selected for further analysis. Keratinase production of the 5 isolates was determined as a second selection in the basal mineral media using feather as the sole carbon and nitrogen source (see for example FIGS. 1C, ID); isolates showed keratinase activity ranging from 0.9-5.9 U/mL.

Effect of Different Factors on Keratinase Production.

Bacterial isolates S1, S15, and S26 were used to investigate the effect of the incubation period, temperature, pH.

substrate concentration and different nutrient combinations of carbon, nitrogen, and sulfur (FIGS. 2A-2D and FIG. 14).

Figure 2A:
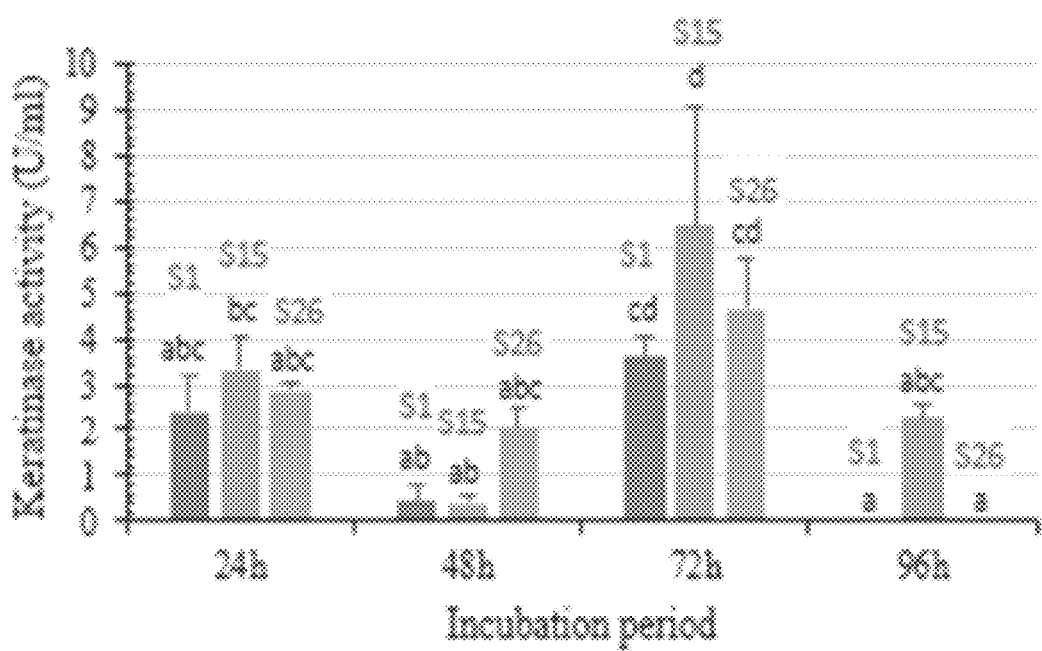
FIG. 2A shows the effect of incubation for 24, 48, 72 and 96 hrs on degradation of chicken feathers by bacterial isolates S1, S15 and S26. Maximum enzyme activity (3.6 U/mL, 6.4 U/mL, and 4.6 U/mL for isolates S1, S15, and S26, respectively) was attained at 72 h of incubation.

The maximum enzyme activity (3.6 U/mL, 6.4 U/mL, and 4.6 U/mL for isolates S1, S15, and S26, respectively) was attained at 72 h of incubation (FIG. 2A).

Figure 2B:
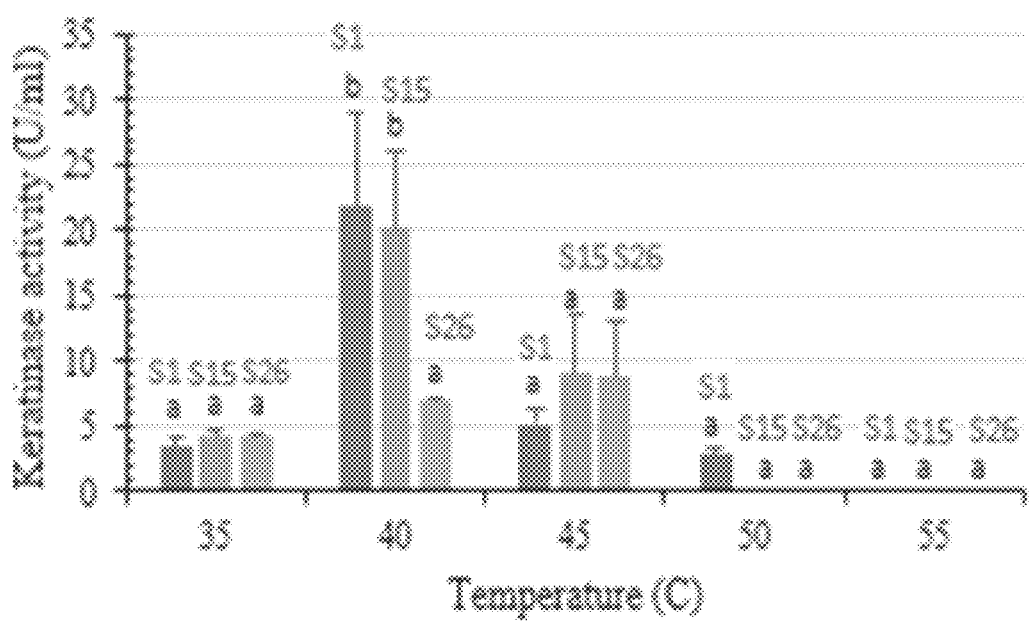
FIG. 2B shows the effect of temperature on degradation of chicken feathers by bacterial isolates S1, S15 and S26. The highest keratinase activity (21.8 U/mL and 20.1 U/mL) was observed at 40° C. for S1 and S15, respectively and 8.7 U/mL at 45° C. for S26.

The temperature effect on keratinase activity revealed that the highest keratinase activity (21.8 U/mL and 20.1 U/mL) was observed at 40° C. for S1 and S15, respectively and 8.7 U/mL at 45° C. for S26. Further, an increase in temperature at 50° C. and 55° C. significantly reduced the activity (FIG. 2B).

Assays were used to study the factors affecting keratinase activity. The effect of incubation period on keratinase activity was determined according to Dhiva, S. et al., Optimization of keratinase production using Pseudomonas aeruginosa Su-1 having feather as substrate. BIOINTERFACE RES. APPL. CHEM. 2020, 10, 6540-6549. Keratinolytic activity of isolates S1, S15, and S26 was determined on basal salt medium containing 10 g/l defatted white chicken feathers as a sole C and energy source at initial pH 7 at 24 h intervals during an incubation period of 24 h-96 h at 45° C. under shaking at 270 rpm. At the end of the incubation period the keratinase activity was determined.

The effect of temperature on enzyme activity was determined according to the method of Aly, M. M. et al., *Isolation, identification, and characterization of a keratolytic bacterium from poultry wastes*. IOSR J. PHARM. BIOL. SCI. 2019, 14, 46-50. Keratinolytic activity of isolates S1, S15, and S26 were determined on basal salt medium containing 10 g/l defatted white chicken feathers as a sole C and energy source at initial pH 7 at different temperatures (35° C., 40° C., 45° C., 50° C. and 55° C.) for 72 h under shaking at 270 rpm. At the end of incubation period the keratinase activity was determined.

The effect of initial pH of the medium on keratinase activity was determined according to Aly, M. M. et al., *Isolation, identification, and characterization of a keratolytic bacterium from poultry wastes*. IOSR J. PHARM. BIOL. SCI. 2019, 14, 46-50. Isolates S1, S15, and S26 were grown for 72 hours under shaking at 270 rpm on the previously described basal salt medium containing 10 g/l defatted white chicken feathers as a sole C and energy source at an incubation temperature of 45° C. and different initial pH values ranging from 6 to 9. At the end of the incubation period the keratinase activity was determined.

The impact of white chicken feather concentrations on the enzymatic activity was assessed according to Kalaikumari. S. et al., *J. Bioutilization of poultry feather for keratinase production and its application in leather industry*. J. CLEAN. PROD. 2019, 208, 44-53. Isolates S1, S15, and S26 were grown at 45° C. for 72 hours under shaking at 270 rpm on the same described basal salt medium with different chicken feather concentrations 0.5, 1, 1.5, and 2% at initial pH 7.5. At the end of the incubation period the keratinase activity was determined.

Figure 2C:
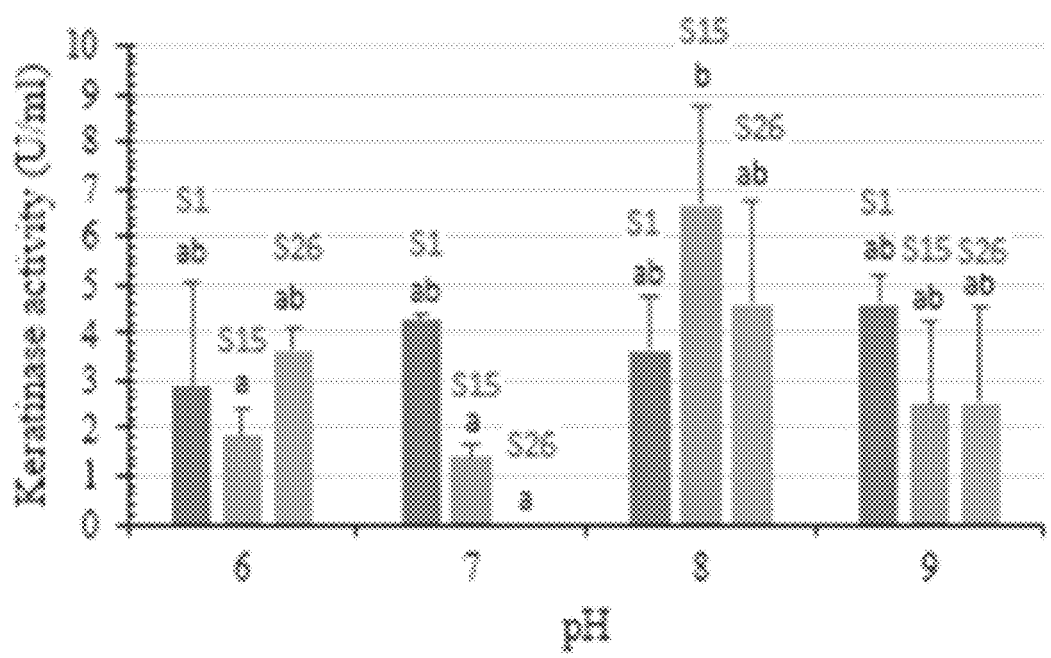
FIG. 2C shows the effect of pH 6, 7, 8 and 9 on degradation of chicken feathers by bacterial isolates S1, S15 and S26. The highest enzyme activity (6.6 U/mL and 4.6 U/mL) was observed at pH 8 for isolates S15 and S26, respectively, and (4.5 U/mL) at pH 9 for isolate S1.

Keratinase activity U/mi on Y axis is proportionate to amount of feather degraded. The keratinase active was measured at the end of each incubation period from 24 h to 96 h. The drop-in degradation after 48 h of incubation may be due to handling errors. The effect of various initial pH values on keratinase activity was studied. Results revealed enzyme activity in a pH range of 6-9. The highest enzyme activity (6.6 U/mL and 4.6 U/mL) was observed at pH 8 for isolates S15 and S26, respectively, and (4.5 UI/mL) at pH 9 for isolate S1 (FIG. 2C).

Figure 2D:
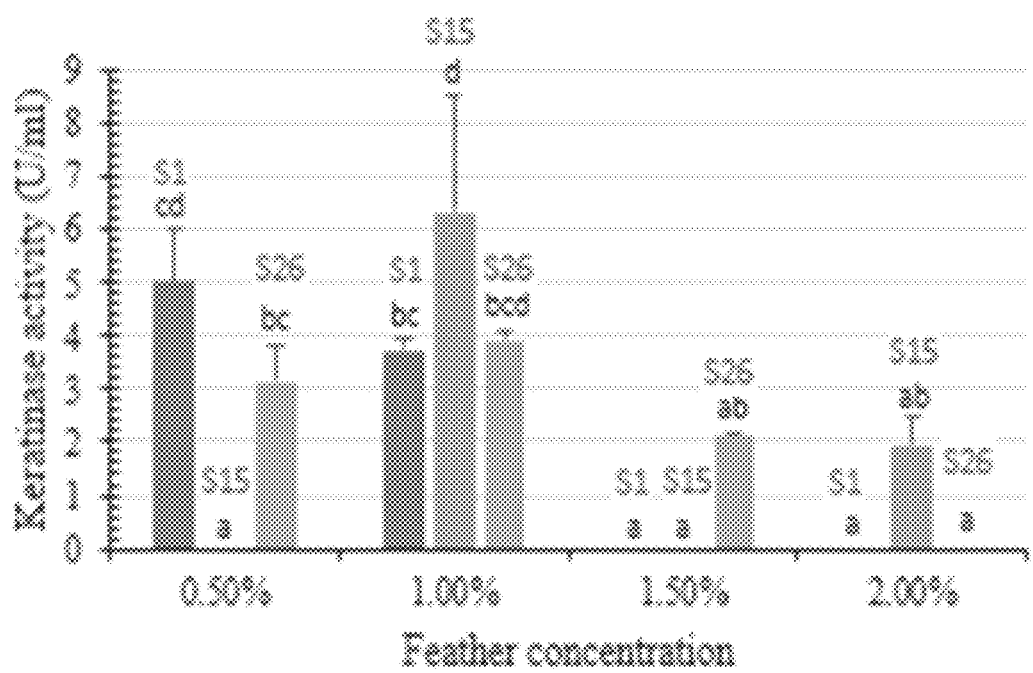
FIG. 2D shows the effect of feather concentration on degradation of chicken feathers by bacterial isolates S1, S15 and S26. Maximum keratinase activity (6.3 U/mL and 3.9 U/mL) was obtained at 1% substrate concentration for isolate S15 and S26. However, 0.5% feather concentration was the optimum (5.0 U/mL) for isolate S1.

The effect of different concentrations of white chicken feather (0.5-2%) on keratinase activity was investigated. Maximum keratinase activity (6.3 U/mL and 3.9 U/mL) was obtained at 1% substrate concentration for isolate S15 and S26. However, 0.5% feather concentration was the optimum (5.0 U/mL) for isolate S1 after 72 h of incubation (FIG. 2D).

Supplementation of an additional $MgSO_4$ $7H_2O$ as a sulfur source individually and in combination with $NH_4Cl$ as a nitrogen source increased keratinase activity of SL; the addition of $NH_4Cl$ individually increased keratinase activity of S26 and decreased keratinase activity of S15 when compared with the medium supplemented with feather only (control). However, the addition of glucose as a carbon source resulted in a decrease in keratinase activity; FIG. 14.

FIG. 14 provides guidance as to which additives promote keratinase activity of S1, S15 and S26 strains. In some embodiments, one or more of these ingredients may be added to a solution containing keratin in an amount that is ±0, 5, 10, 20, 30, 40 or 50 wt. % of the amount described in FIG. 14 to enhance keratinase activity of the strains disclosed herein. Chicken feather is made up of f-keratin protein which is rich in both carbon and nitrogen. The inventors consider that the addition of carbon, sulfur, and nitrogen sources along with feathers will improve the production of keratinase.

Feather Biodegradation In Vitro.

The keratin-biodegradation ability and keratinase activity by S1, S15, and S26 using various keratin substrates (white chicken feather, black chicken feather, white sheep wool, black sheep wool, and human hair) were studied (FIG. 3 and FIG. 15A-15J. These results provide a basis for selecting a particular type of modified keratinase for use in applications where selective degradation of a particular type of keratin is desired. For example, any of the S1, S15 or S26 keratinases may be selected to degrade white or black chicken feathers, but S26 keratinase may be selected to preferentially degrade white sheep wool keratinase, S15 to selectively degrade black sheet wool keratin, and S26 keratinase may be selected to avoid degrading keratin in human hair. Other selections of one or more keratinases may be made based on the differential degradation results in FIG. 3.

Figure 3:
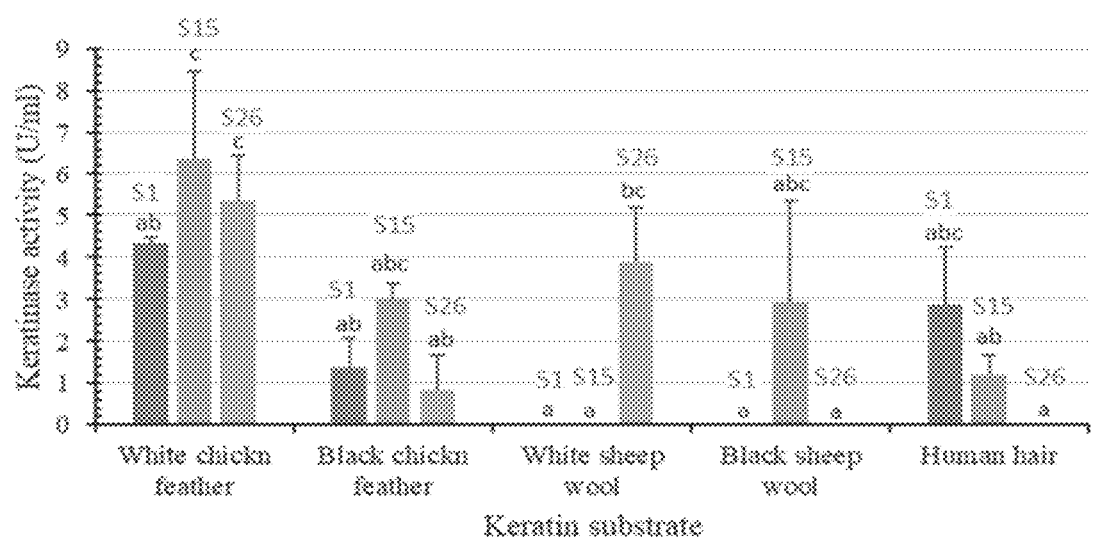
FIG. 3. Depicts in vitro biodegradation of different keratin substrates (i.e., white chicken feather, black chicken feather, white sheep wool, black sheep wool, and human hair) after incubation with the keratinolytic bacteria for 72 h at 45° C. White chicken feather as substrate yielded the highest keratinase activity: 6.3 U/mL for SS. 5.3 U/mL for S26 and 4.3 U/mL for S1. Bars are the standard error of the mean. Mean with the different letters are significantly different according to Duncan's multiple comparison test at p<0.05.

White chicken feather as substrate yielded the highest keratinase activity (6.3 U/mL for S15, 5.3 U/mL for S26 and 4.3 U/mL for S1), followed by white sheep wool (3.8 U/mL for S26), black chicken feather (3.0 U/mL for S15), black sheep wool (2.9 U/mL for S15) and human hair (2.8 U/mL for S1) (FIG. 3).

As shown by FIGS. 15A-15J, no degradation was observed with the control. Isolate S15 showed partial degradation of the white chicken feather (up to 52.50%) and produced the highest keratinase production (6.3 U/mL) at 45° C. and pH 8.85 after 72 h of incubation. Unlike other keratinolytic *Bacillus* spp. that demonstrated remarkable feather degradation after 7-10 days, significant partial degradation of white sheep wool, black chicken feather, and black sheep wool indicate the ability of the disclosed isolates to degrade both α-keratin and f-keratin. Other keratinases act on different keratin substrates and have different degrees of activity; see Park, G. T. et al., Keratinolytic activity of Bacillus megaterium F7-1, a feather-degrading mesophilic bacterium. MICROBIOL. RES. 2009, 164, 478-485; Williams, C. M. et al., Isolation, identification, and characterization of a feather-degrading bacterium. APPL. ENVIRON. MICROBIOL. 1990, 56, 1509-1515. Similarly, B. megaterium F7-1 effectively degraded feather meal, duck feather, and human nail, whereas human hair and sheep wool showed relatively low degradation rates; Park, G. T. et al., supra.

Improvement of Keratinase Production by Random Mutagenesis.

The keratinase activity of the five keratinolytic bacterial isolates was modified or developed by exposure to UV radiation and ethyl methanesulfonate (EMS), individually and in a combination of UV and EMS.

Figures 1, 4A:
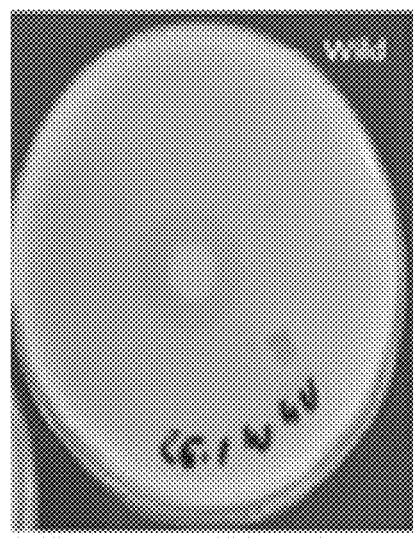
FIGS. 4A-1-4A-2 illustrate the effect of random UV mutagenesis on keratinase activity. Wild type (FIG. 4A-1) and UV-mutated isolate S26 (FIG. 4A-2) show clear zones of hydrolysis on skim milk agar.
Figures 2, 4A:
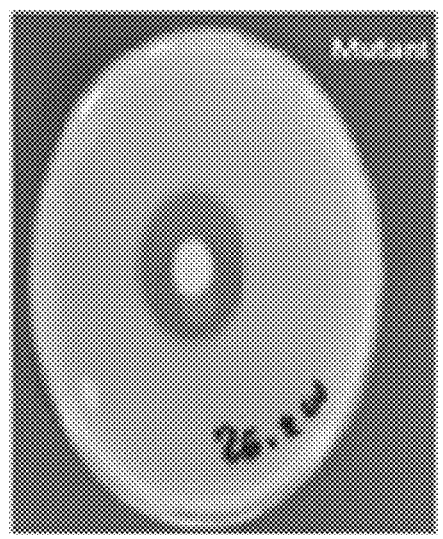

UV radiation was used to enhance keratinase production by solates S1, S13, S15, S26, and 539. Representative clear zone hydrolysis using skim milk for the wild and mutated isolates is shown in FIG. 4A-1 (wild) and FIGS. 4A-2 (mutant).

Figure 4B:
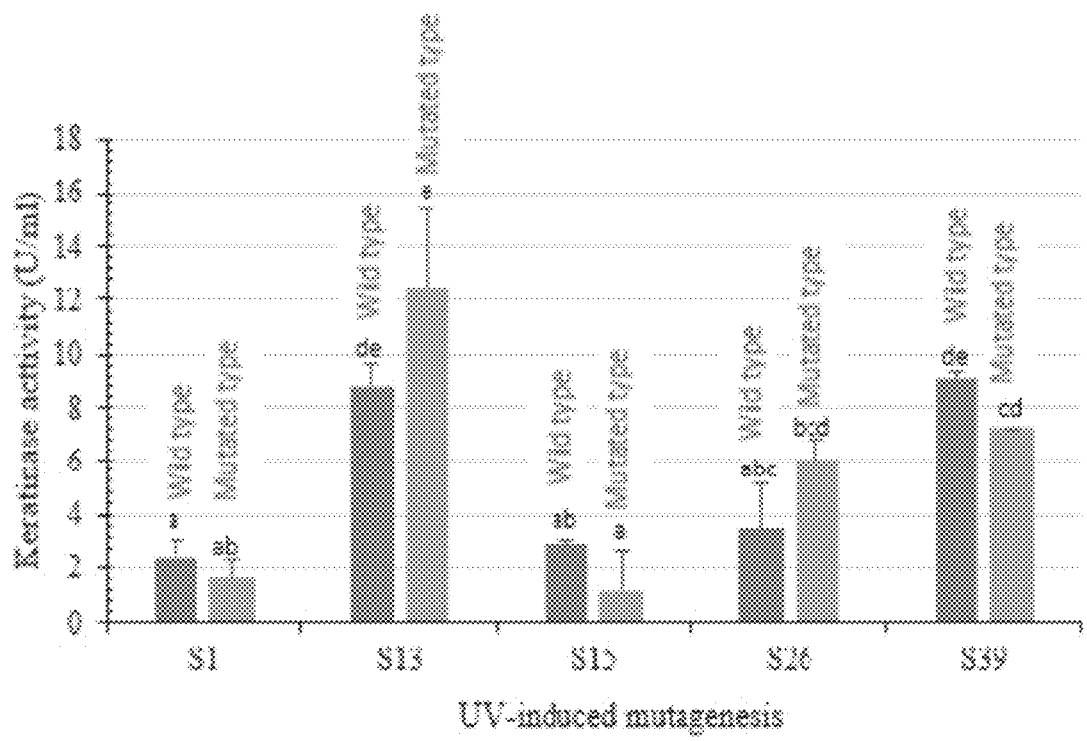
FIG. 4B. Keratinolytic activity of wild isolates and their corresponding UV-induced mutants. Mutants S13uv and S26uv showed high keratinase activity (12.4 U/mL and 6.0 U/mL, respectively) compared with their wild isolates S13 and S26 (8.7 U/mL and 3.4 U/mL, respectively) after 72 h of incubation. Bars are the standard error of the mean. Mean with the different letters are significantly different according to Duncan's at p<0.05.

Mutants S13uv and S26uv showed high keratinase activity (12.4 U/mL and 6.0 U/mL, respectively) compared with their wild isolates S13 and S26 (8.7 U/mL and 3.4 U/mL, respectively) after 72 h of incubation (FIG. 4B). Zeng, Y. H. et al., *The flexibility of UV-inducible mutation in Deinococcus ficus as evidenced by the existence of the ImuB-DnaE2 gene cassette and generation of superior feather degrading bacteria*. MICROBIOL. RES. 2011, 167, 40-47 reported that mutant CC-ZG207 of *D. ficus* showed 2-fold higher keratinolytic activity after 10 days of incubation; in contrast, the activity of mutant CC-ZG227 was lower than wild type. These results and those in FIG. 5 provide a basis for selection of a wild-type or mutant keratinase with a higher or lower activity. A higher activity keratinase may be selected depending on desired digestion conditions or length of digestion time. A lower activity keratinase may be selected to slow digestion of keratin and a keratinase with higher activity selected to speed digestion time.

Figure 5A:
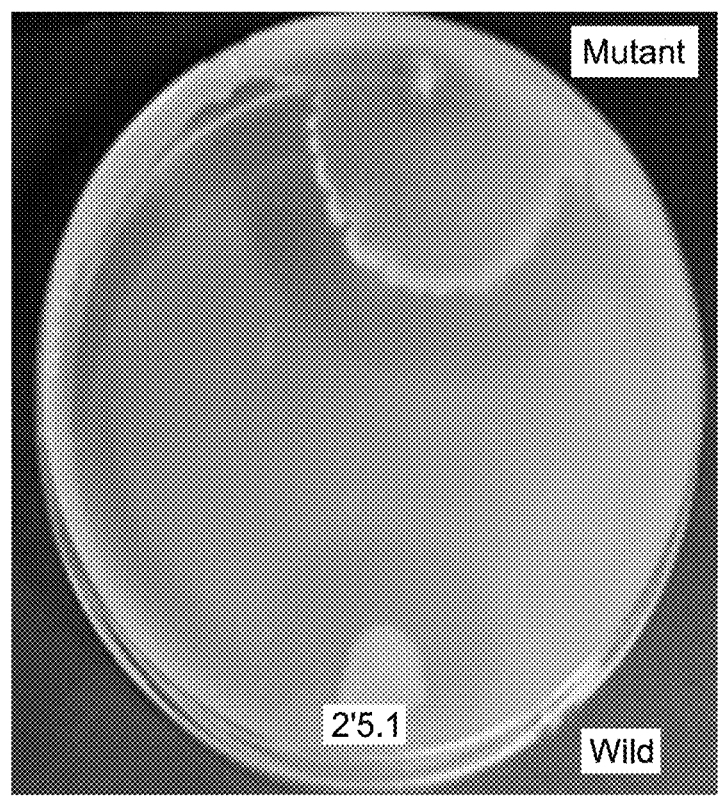
FIG. 5A and FIG. 5B illustrate the effect of random EMS mutagenesis on keratinase activity.

Moreover, isolates S1, S13, S15, S26, and S39, as well as UV mutants (S13uv and S26uv) with higher keratinase activity than the wild type were treated with EMS. Clear zone hydrolysis using skim milk for the wild and mutated isolates is shown in FIG. 5A: mutant (top) vs. wild (bottom).

Figure 5B:
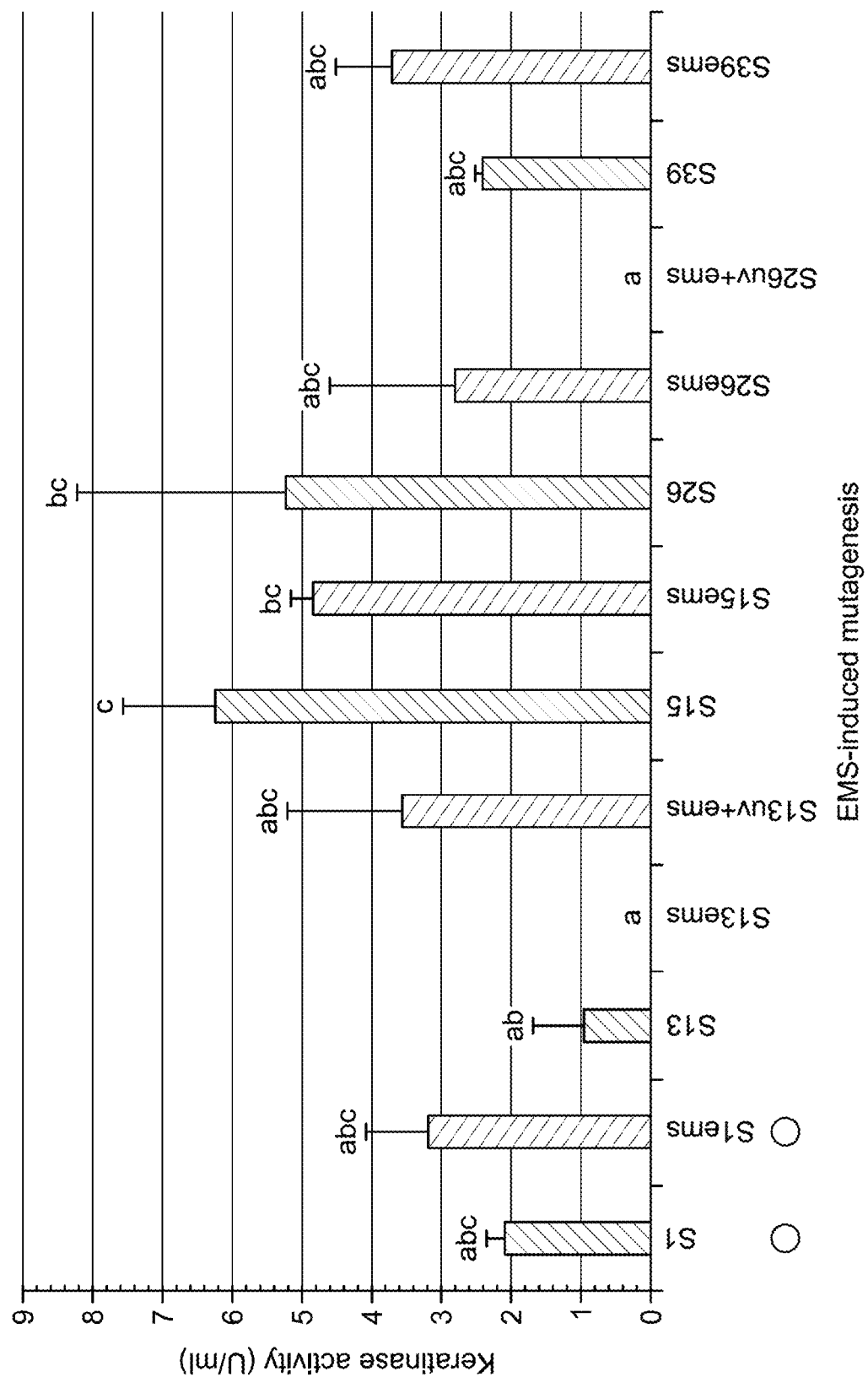

Keratinase activity was increased with the mutants S1ems (3.2 U/mL) S13uv+ems (3.5 U/mL), and S39ems (3.7 U/mL) compared with the wild isolates after 72 h of incubation (FIG. 5B). Results of this study indicated that mutations by EMS increased keratinase activity from 1.5-3.7-fold compared with the wild isolates.

Evaluation of Biodegradation Efficiency of the Wild and Mutant Isolates by Digital Camera and Scanning Electron Microscopy (SEM).

Figures 1, 6A:
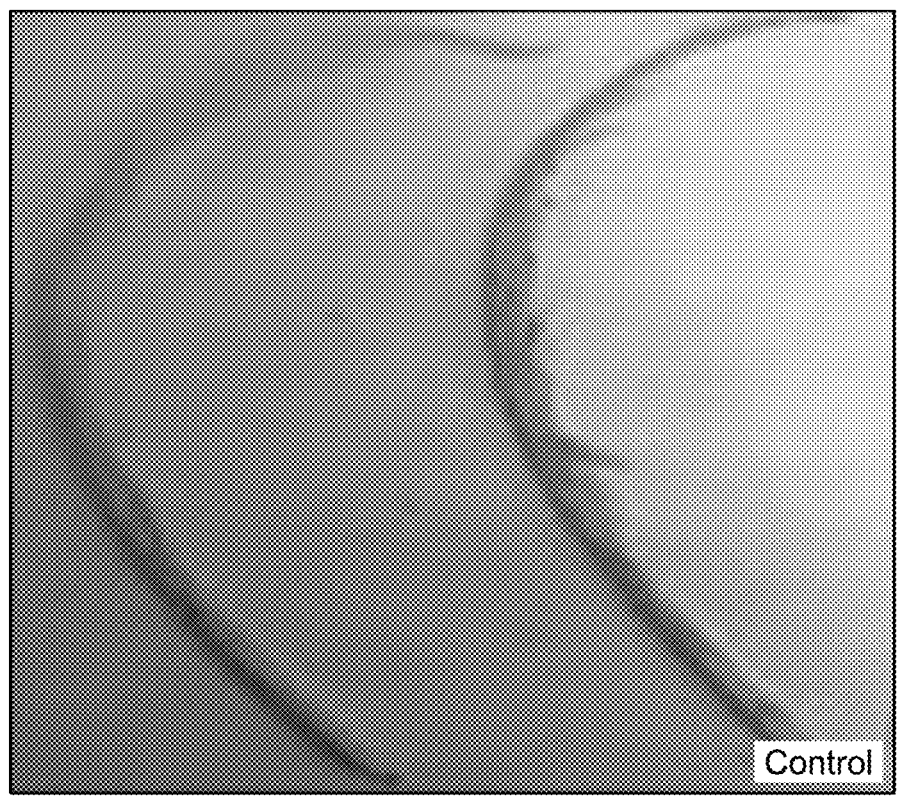
Figures 2, 6A:
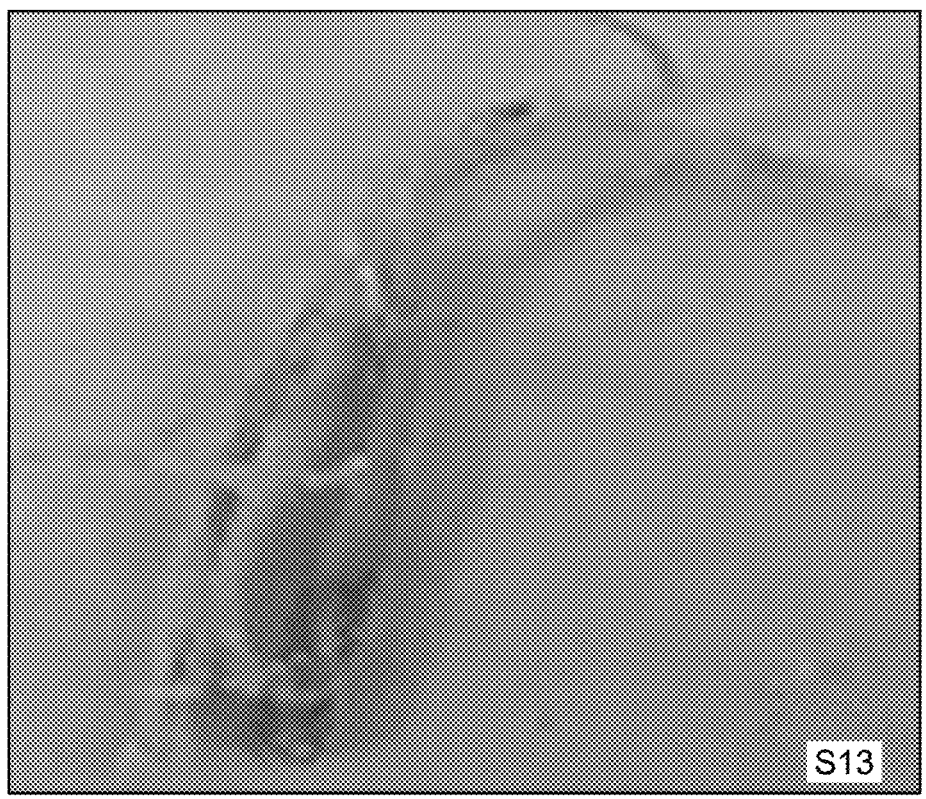
Figures 3, 6A:
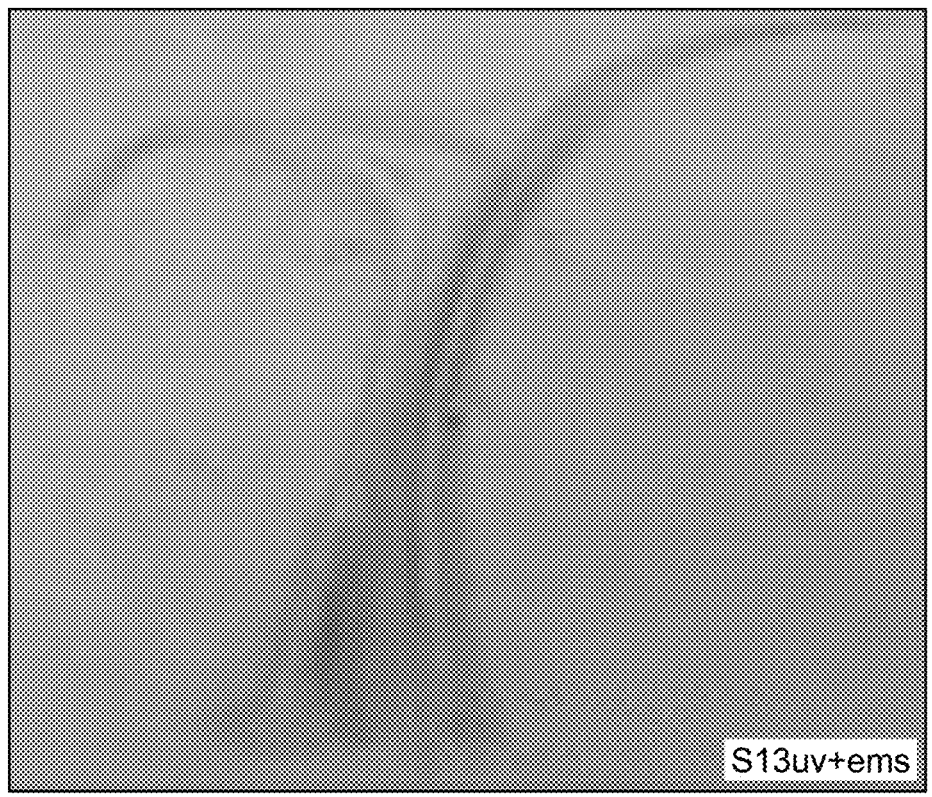
Figures 4, 6A:
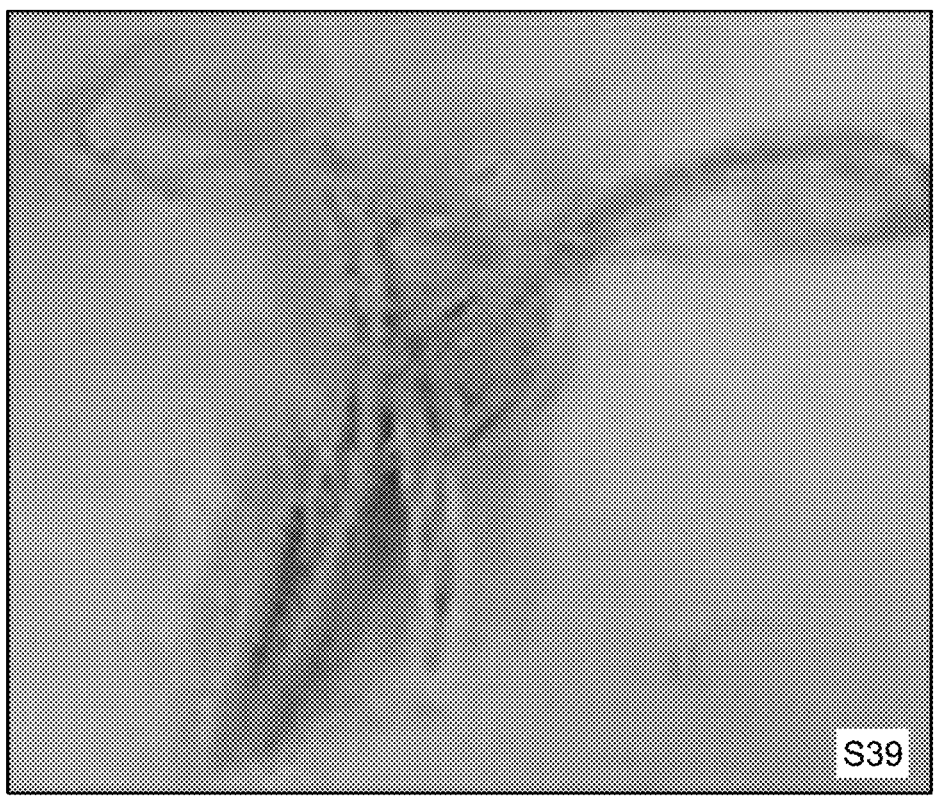
Figures 5, 6A:
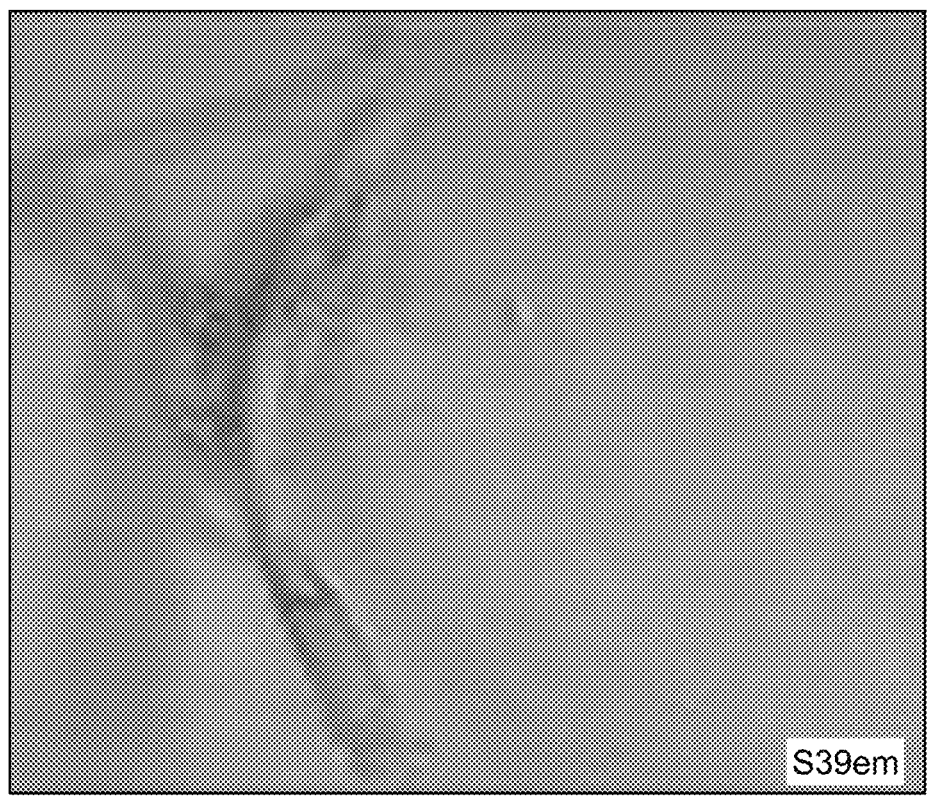
Figures 1, 6B:
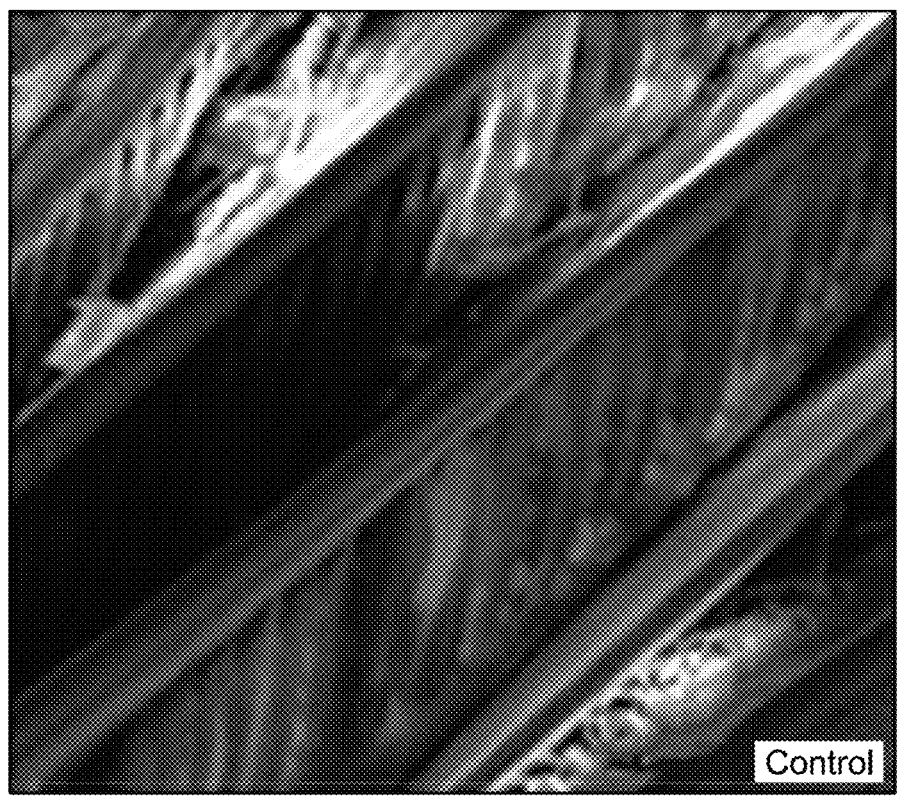
Figures 2, 6B:
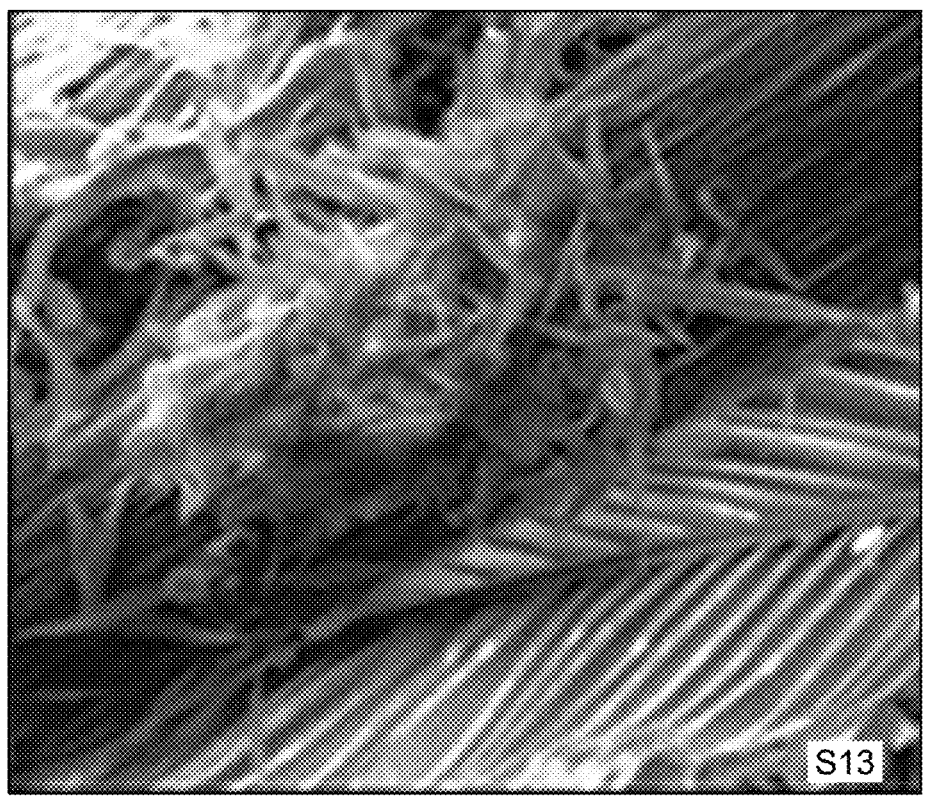
Figures 3, 6B:
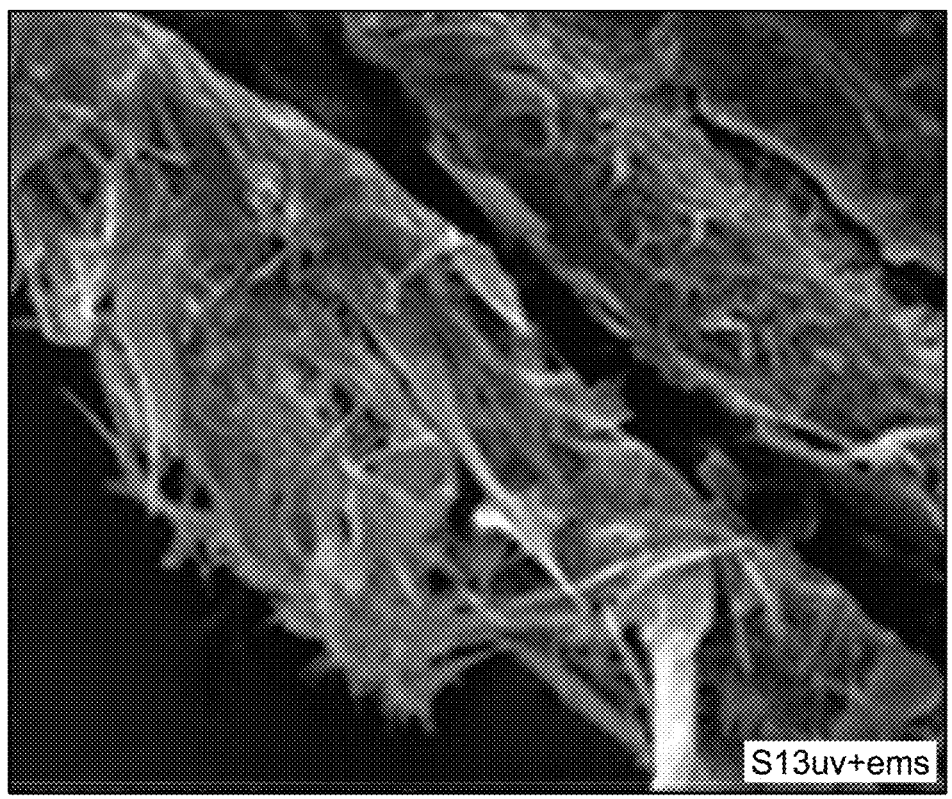
Figures 4, 6B:
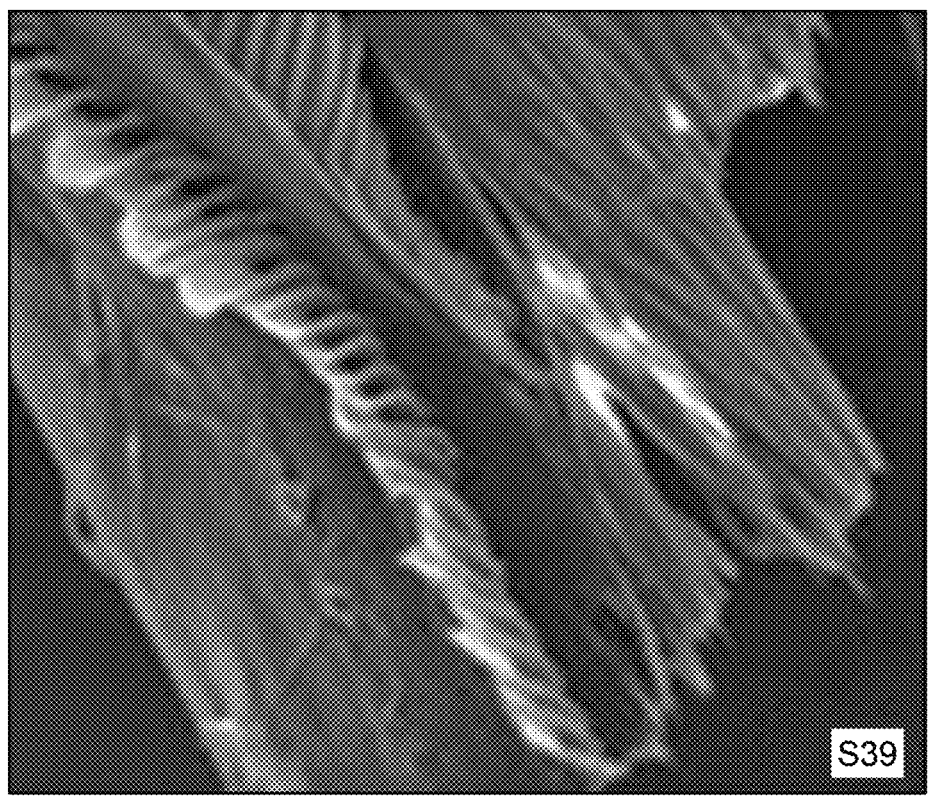
Figures 5, 6B:
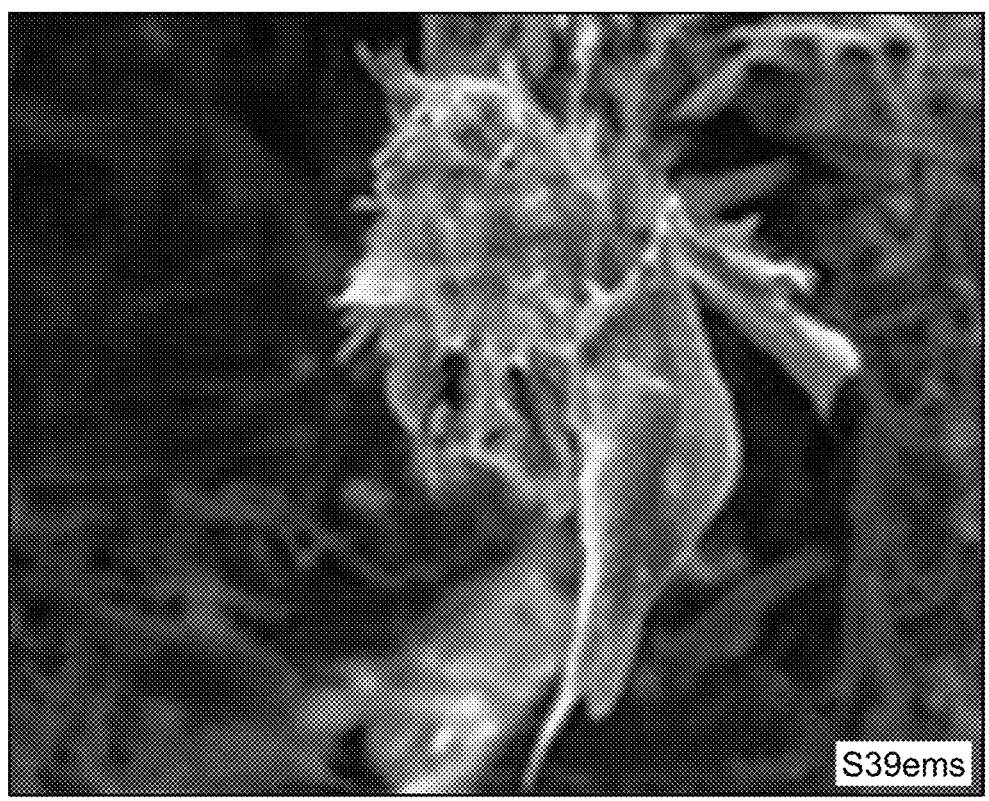

The digital photos and SEM micrographs showed a degradative action of S13, S13uv+ems, S39, and S39ems on the chicken feather as keratinous substrate (FIGS. 6A-1 to 6A-5, digital camera; FIGS. 6B1 to 6B-5, SEM) presented in Table 1 below showed improvement in keratinase activity and feather degradation with the mutants S13uv+ems (4.0 U/mL and 65%) and S39ems (3.5 U/mL and 57.5%) compared with their wild isolates S13 (2.7 U/mL and 45%), and S39 (2.7 U/mL and 22.5%) after 72 h of incubation. FIGS. 6A-1 to 6A-5 and 68-1 to 6B-5 depict the deterioration of feather structure as a result of the keratinase activity. The rachis surface was disrupted and the advanced fragmentation and detachment of feather barbs were observed. However, as fermentation progressed, the barbules were partially degraded from the vane. The significance of the SEM imaging process includes proving the ability of the disclosed keratinolytic bacteria to hydrolyze the feather keratin and to understand the degradation pattern.

TABLE 1

Evaluation of feather degrading ability of S13uv + ems and S39ems and their wild type for SEM analysis.

| Bacterial Strains | pH | Feather Hydrolysis (%) | Keratinase Activity (U/ml) |
|---|---|---|---|
| S13 | 9.55 ± 0.02 [ab] | 45.00 ± 0.00 [b] | 2.72 ± 0.20 [a] |
| S13uv + ems | 9.59 ± 0.07 [ab] | 65.00 ± 0.00 [d] | 4.07 ± 0.71 [a] |
| S39 | 9.18 ± 0.11 [a] | 22.50 ± 2.50 [a] | 2.71 ± 0.62 [a] |
| S39ems | 9.69 ± 0.18 [b] | 57.50 ± 2.50 [c] | 3.53 ± 0.18 [a] |
| p-value | 0.101 | 0.000 | 0.138 |

Values are expressed as means ± standard error. Mean with the different letters are significantly different according to Duncan's at $p < 0.05$.

16S rRNA Identification of the Keratinolytic Bacterial Isolates

The five keratinolytic bacterial isolates were identified through amplification and sequencing of the 16S rRNA gene. Sequences were compared with those of the GenBank database using BLASTn. The 5 sequences were 100% identical and shared 99.82-100% identity to the species of *Bacillus cereus* group. In Saudi Arabia, Alshehri, W. A. et al., *Bio-plastic films production from feather waste degradation by keratinolytic bacteria Bacillus cereus*. J. PURE APPL. MICROBIOL. 2021, 15, 681-688 reported that *Bacillus* sp. BAM3 have been identified based on 16S rDNA as *Bacillus cereus* BAM3 sharing 98.9-10% identity.

Figure 7:
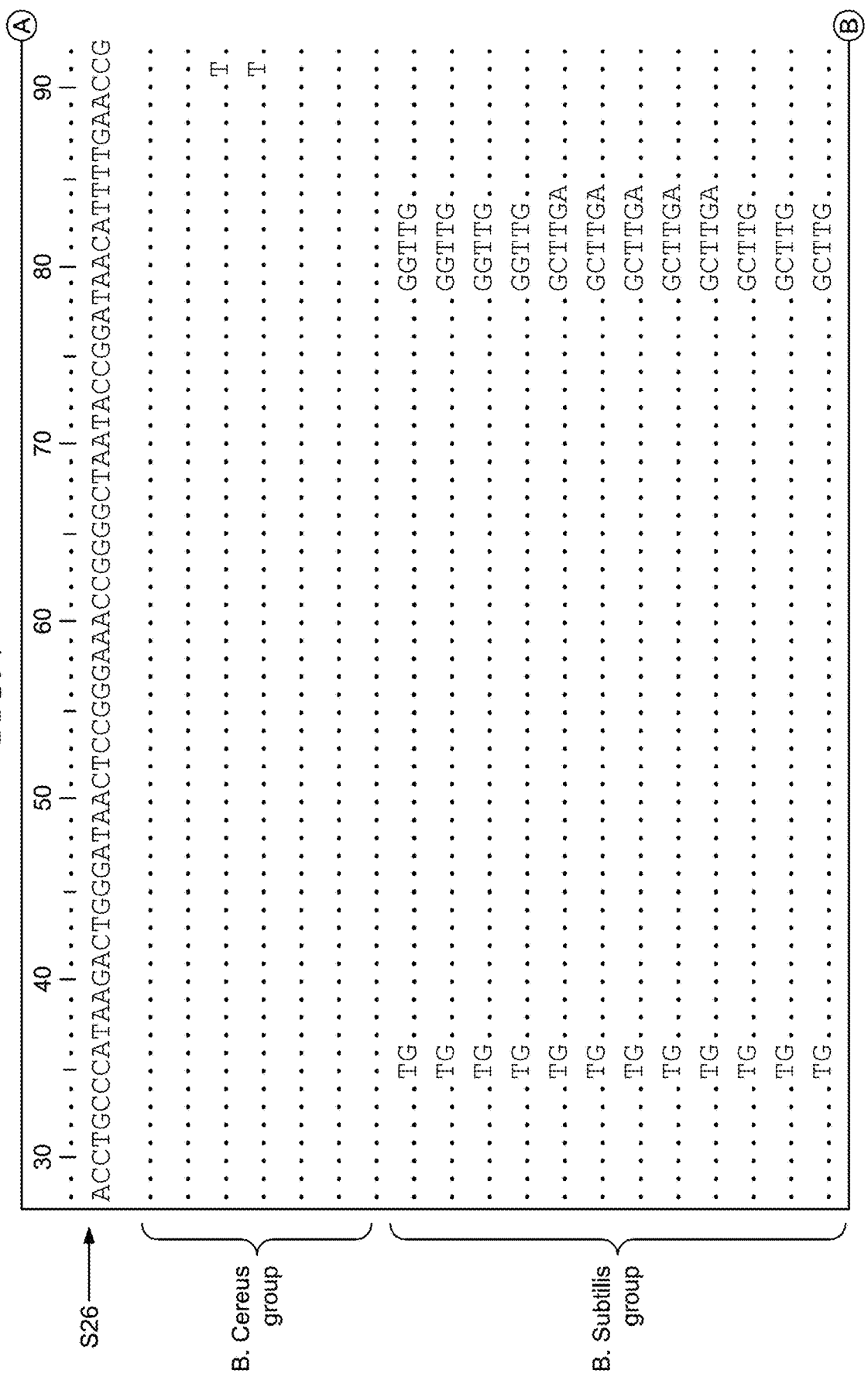
FIG. 7 illustrates the multiple sequence and neighbor-joining phylogenetic analysis of 16S rRNA gene strain S26 against sequences retrieved from GenBank database. The S26 sequence at the top of this figure corresponds to SEQ ID NO: 8, nucleotides 34-98 and this sequence is compared to those of other strains or isolates in the *B. cercus* and *B. subtilis* groups.
Figure 7:
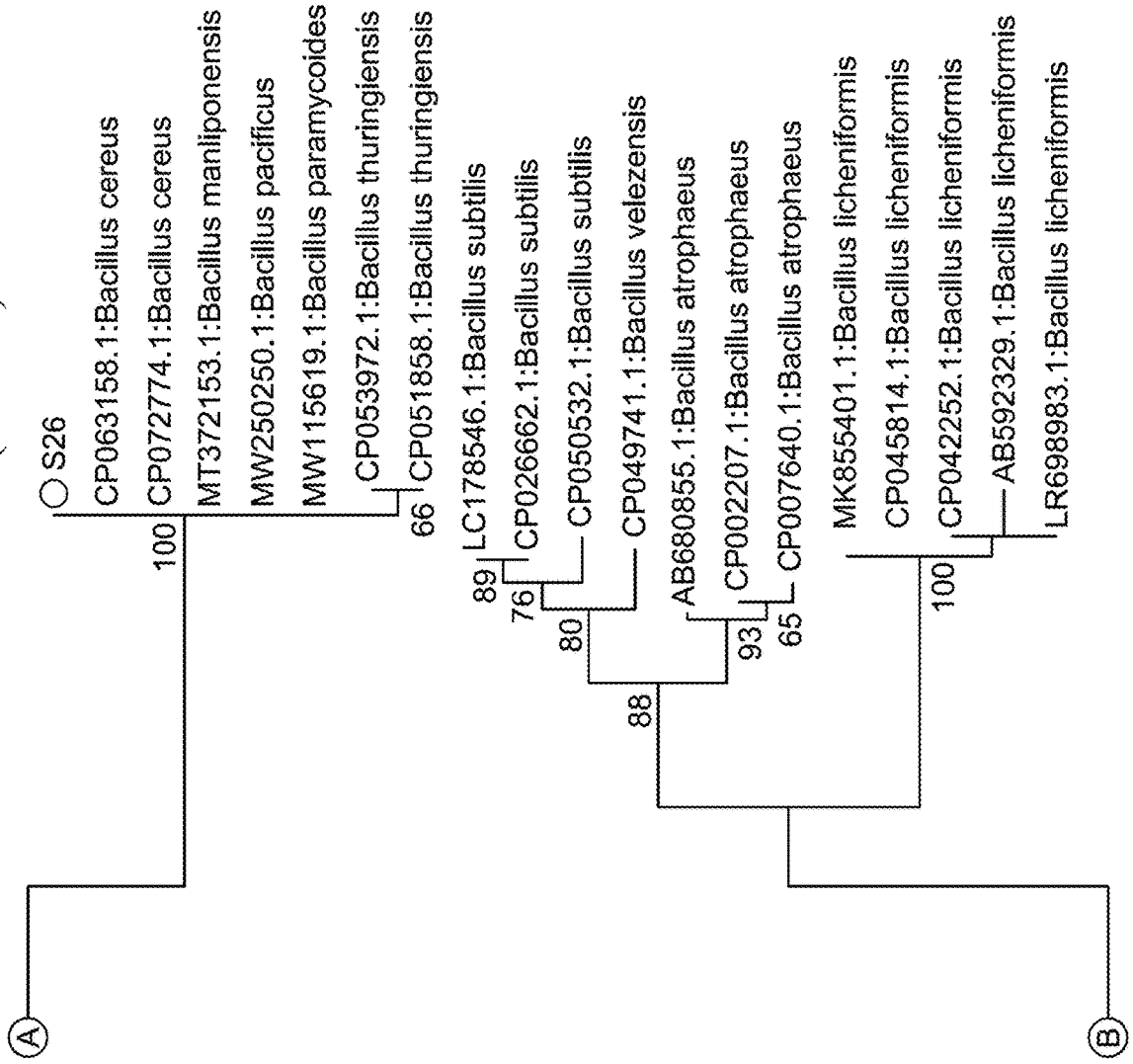
Figures 1, 8:
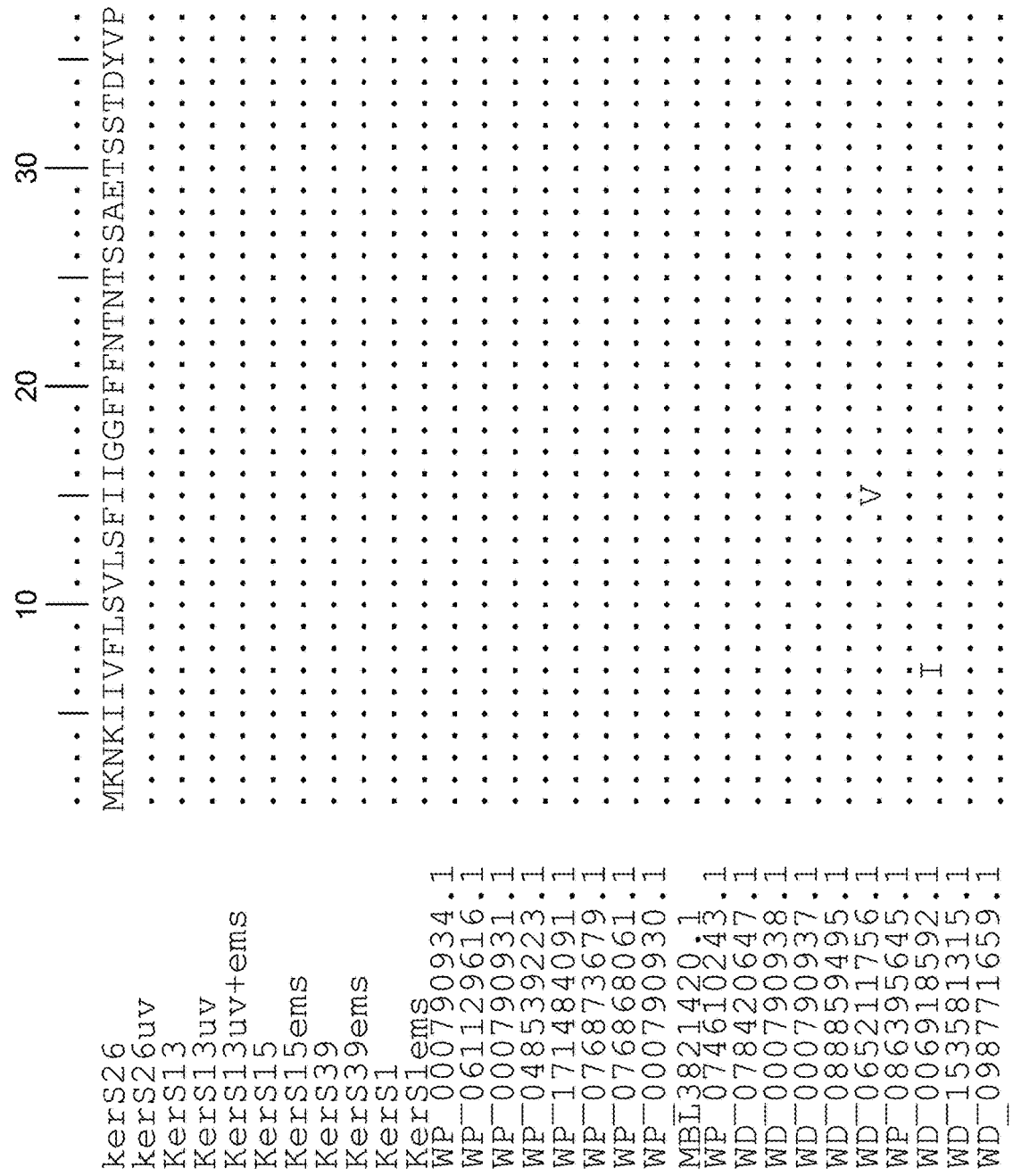
FIG. 8 (panels 8-1, 8-2, 8-3, 8-4 and 8-5) illustrate the multiple amino acid sequence analysis of KerS gene against S8 family peptidase *Bacillus cereus* group sequences retrieved from GenBank database. The KerS26 amino acid sequence starting on panel 8-1 and continuing through to last panel 8-5 is given by SEQ ID NOS: 25. Keratinase genes for strains disclosed herein correspond to the sequence identifiers shown below or from S8 family peptidase *Bacillus cereus* group sequences retrieved from GenBank database.
Figures 1, 8:
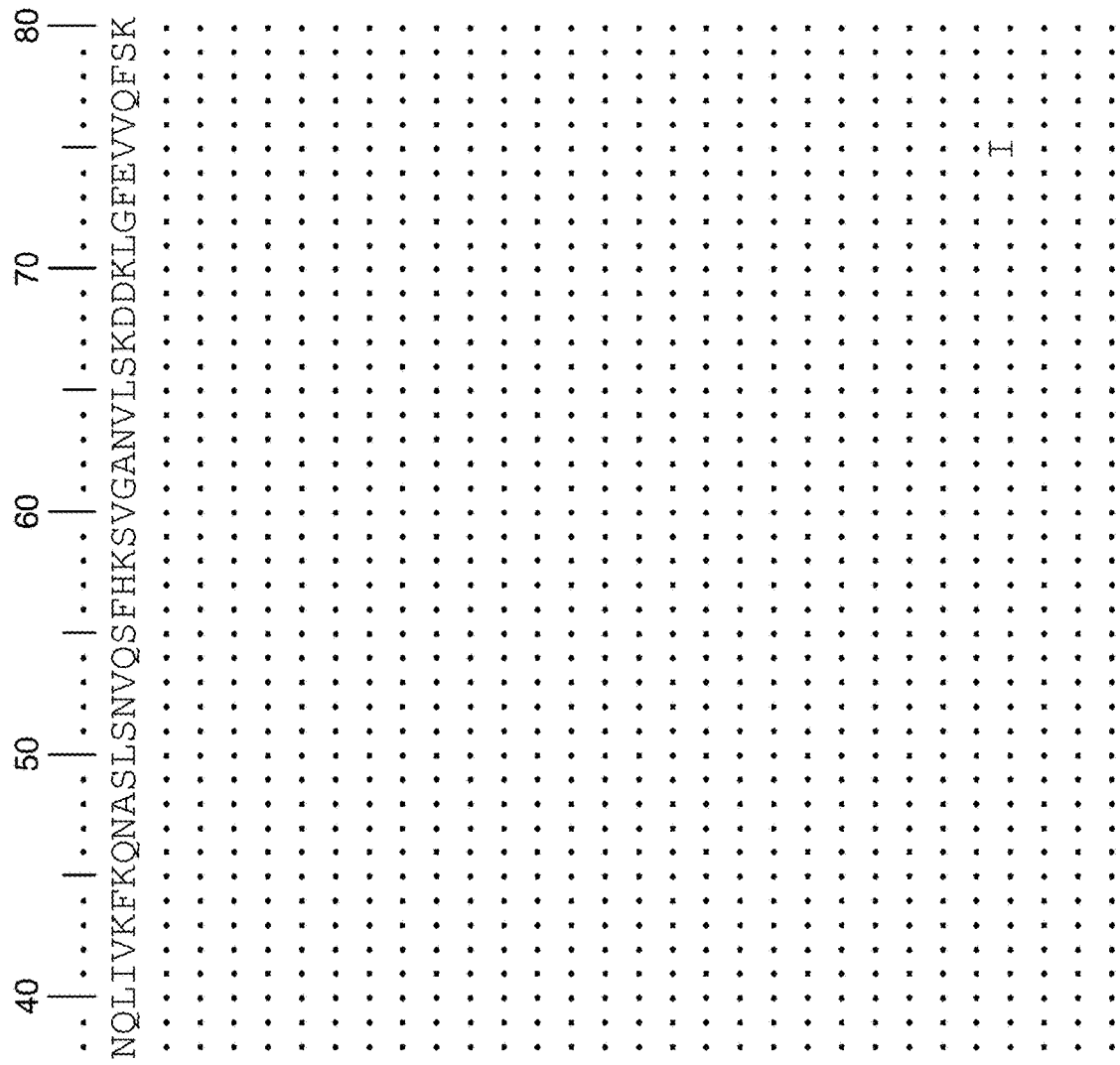
Figures 3, 8:
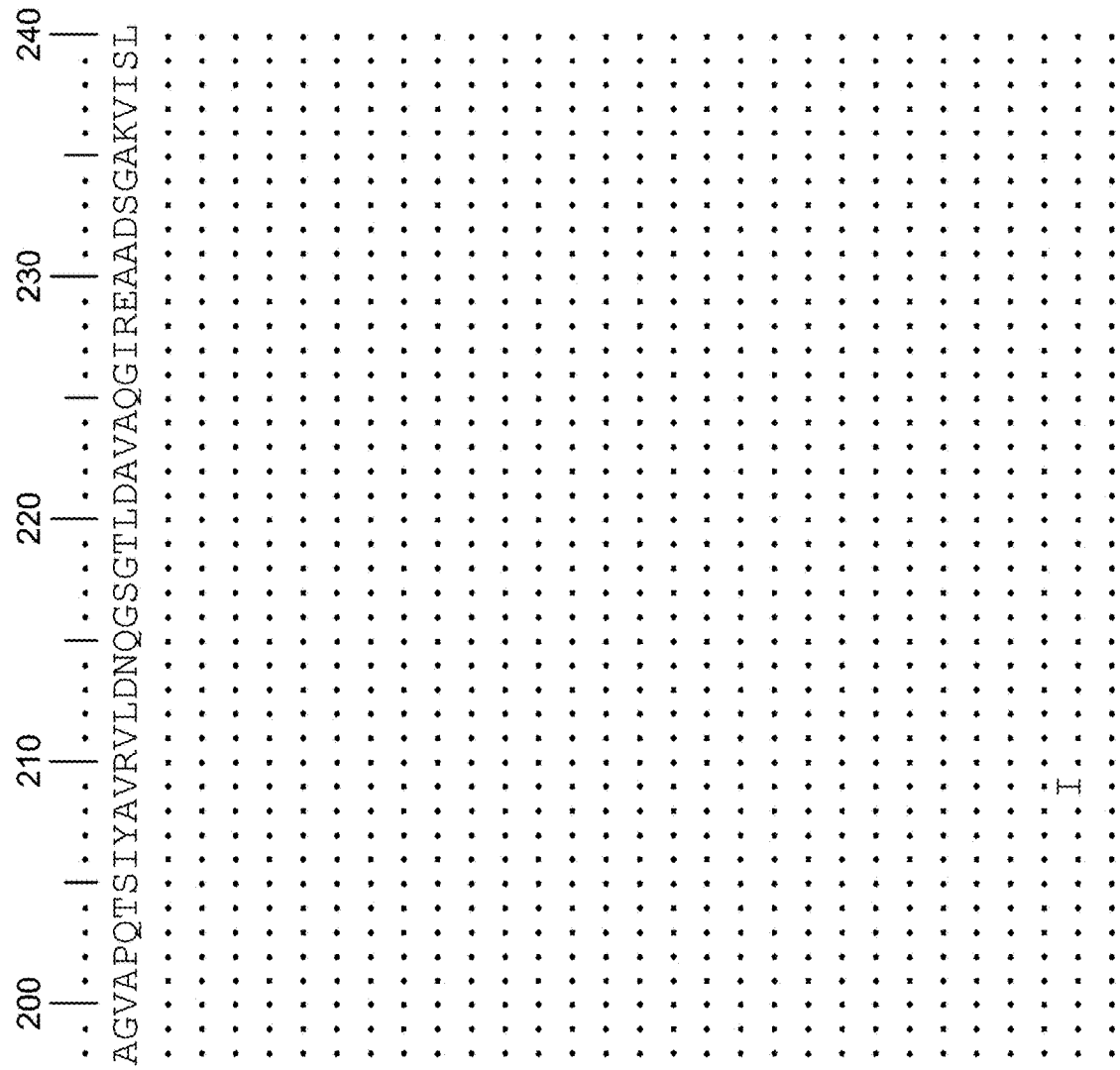
Figures 4, 8:
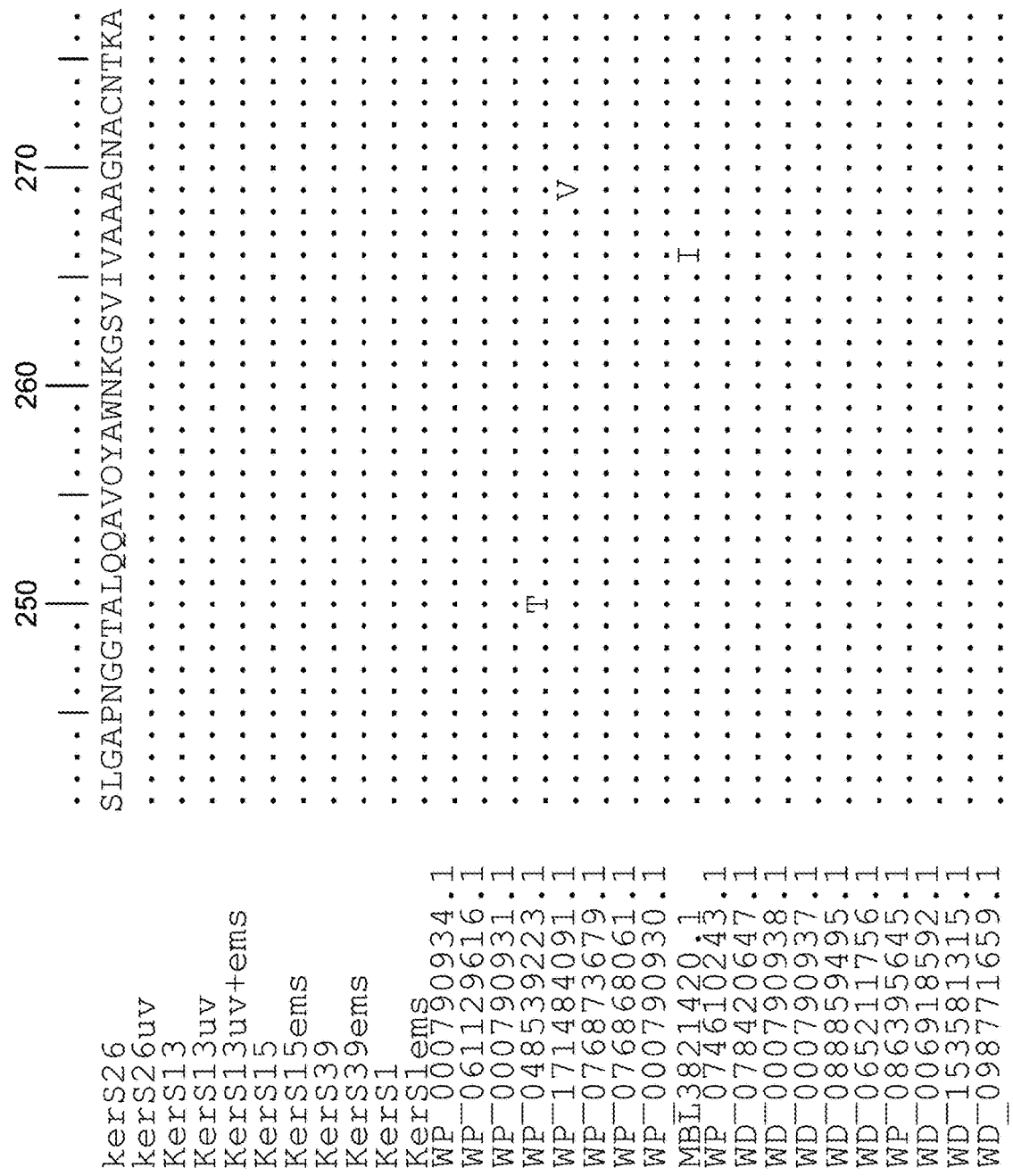
Figures 5, 8:
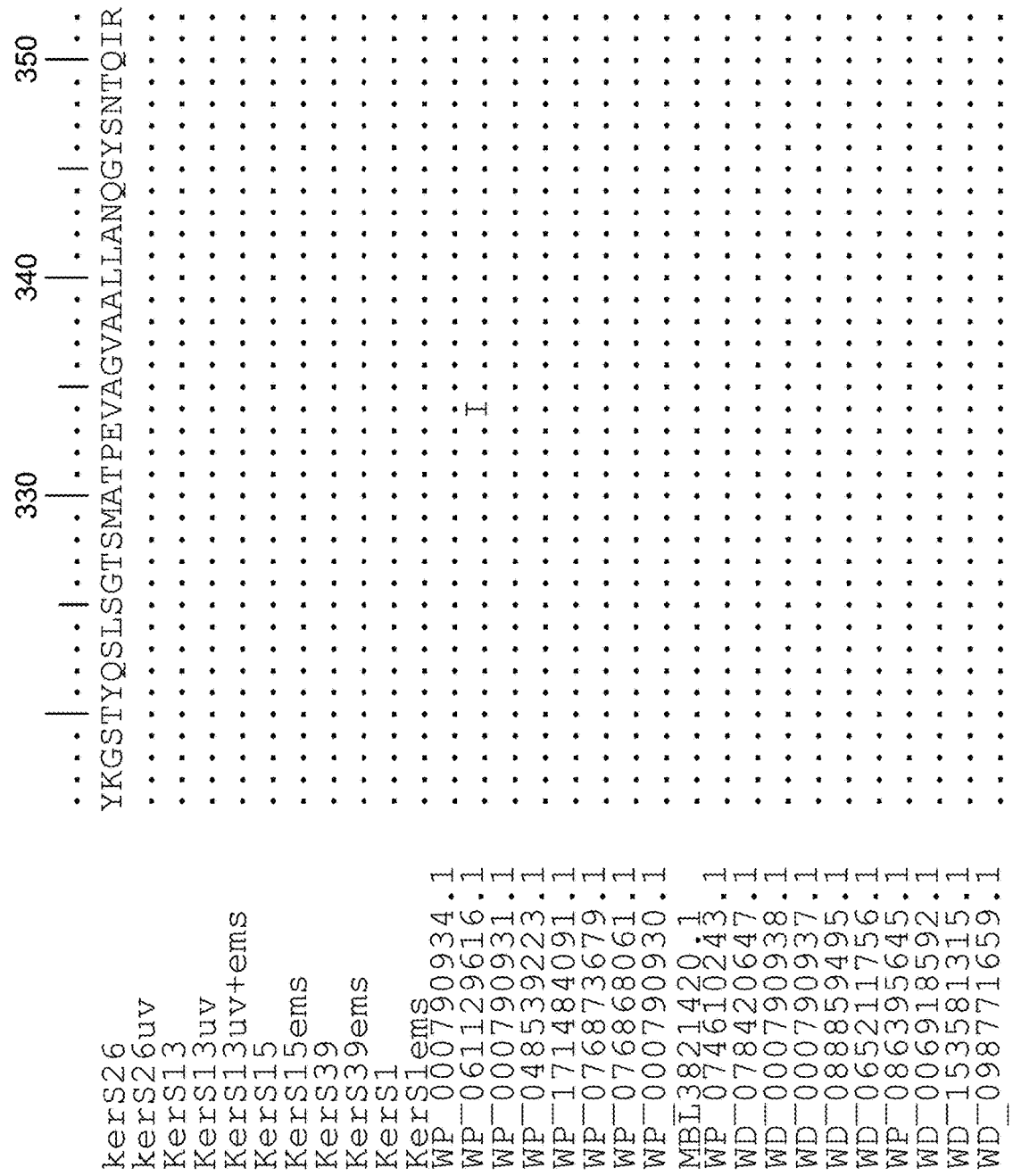

In addition, multiple sequence alignment and phylogenetic analysis against the 16S rRNA sequence of *B. subtilis* and *B. cereus* groups retrieved from the GenBank database clearly showed the close relationship between our strains and those of the *B. cereus* group (FIG. 7). Furthermore, 58 major substitution positions were detected and differentiated between *B. subtilis* and *B. cereus* groups in a region of 1209 nt (FIG. 16). These positions could be used as markers to differentiate between species belonging to the *B. subtilis* group from those of the *B. cereus* group; see the characterization methods described by and incorporated by reference to, Mahmoud, A. et al., *In Vitro and in silico characterization of alkaline serine protease from Bacillus subtilis D9 recovered from Saudi Arabia*. HELIYON 2021, 7, e08148.

In Silico Characterization of the Wild-Type Keratinase KerS and Mutants.

Keratinase (KerS) gene from strains S1, S13, S15, S26, and S39, as well as their corresponding mutants, was amplified and sequenced. Different bioinformatics tools were used to analyze various aspects of the KerS gene, which included sequence similarity, phylogenetic analysis, functional analysis, physicochemical characterization, and prediction of keratinase 3D structure and molecular docking.

Keratinase Gene Similarity Search.

Based on the similarity between our keratinase KerS gene sequences (98-100%), KerS13, KerS13uv+ems and KerS26uv were selected as representative sequences for further analysis. KerS gene is composed of 704-1194 nt and 234-397 aa. Using BLASTp, amino acid sequence analysis of KerS gene revealed a high level of identity (97.98-100%) with S8 family peptidase of *B. cereus* group, see Table S1.

TABLE S1

BLASTp analysis of keratinase kersS showing deduced amino acid, total score, query cover, E-value and percentage of identity.

| Keratinase gene | Deduced amino acid | Total score | Query cover | E-value | 95 of identity |
|---|---|---|---|---|---|
| KerS1 | 234 | (481-483) | 100% | (1e-168-4%-170) | (99.15%-100%) |
| KerS1ems | 397 | (795-805) | 100% | 0.0 | (98.24%-100%) |
| KerS13 | 397 | (795-805) | 100% | 0.0 | (98.24%-100%) |
| KerS13uv | 397 | (795-805) | 100% | 0.0 | (98.24%-100%) |
| KerS13uv + ems | 397 | (793-804) | 100% | 0.0 | (97.98%-100%) |
| KerS15 | 397 | (795-805) | 100% | 0.0 | (98.24%-100%) |
| KerS15ems | 397 | (795-805) | 100% | 0.0 | (98.24%-100%) |
| KerS26 | 397 | (795-805) | 100% | 0.0 | (98.24%-100%) |
| KerS26uv | 397 | (795-805) | 100% | 0.0 | (98.24%-100%) |
| KerS39 | 295 | (593-601) | (99%-100%) | 0.0 | (98.64%-100%) |
| KerS39ems | 269 | (547-551) | 100% | 0.0 | (99.26%-100%) |

Table S1: BLASTp analysis of keratinase kers showing deduced amino acid, total score, query cover, E-value and percentage of identity.

S8 family peptidase is a subtilisin-like serine protease with a catalytic triad of Asp/His/Ser, Li, H. J. et al., Characterization of a new S8 serine protease from marine Sedimentary photobacterium sp. A5-7 and the function of its protease-associated domain. Front. MICROBIOL. 2016, 7, 2016. Gurunathan. R. et al., Novel recombinant keratin degrading subtilisin like serine alkaline protease from Bacillus cereus isolated from marine hydrothermal vent crabs. SCI. REP. 2021, 11, 12007 in silico identified keratin degrading subtilisin like serine alkaline protease from *B. cereus*. Fellahi et al. found that the results of amino acid sequences alignment with known *B. pumilus* proteases indicated that the two keratinases Ker1 and Ker2 of *B. pumilus* strain C4 are subtilisin-like serine proteases belonging to the protease S8 family.

Pairwise alignment comparison between KerS gene (KerS13, KerS13uv+ems, and KerS26uv) and two keratinases retrieved from UniprotKB database showed identity between 97.59-99.10%. KerS26uv shared the highest identity (99.10% and 98.80% with keratinase *B. thuringiensis* (A0A1L6PVT6) and keratinase ker 6 *B. cereus* (F8SVT0), respectively). In some embodiments, the *Bacillus* bacteria disclosed herein or their mutants or variants will exhibit between 98.0, 98.5, 99.0, 99.5 and 100% identity with the keratinase sequences from *B. thuringiensis* (AOA 1L6PVT6) or *B. cereus* (F8SVT0). This range includes all intermediate values and subranges.

Multiple Sequence Alignment and Phylogenetic Analysis.

Multiple sequence alignment and phylogenetic analysis of our KerS gene and those of S8 family peptidase, *B. cereus* group, obtained from GenBank database are shown in FIGS. 8 and 9. Comparison of KerS gene sequence of the wild and mutant strains showed $D_{137}N$ substitution in the mutant KerS13uv+ems but not in the wild KerS13. After mutagenesis, the activity of keratinase KerS13uv+ems was found to be a 3.73-fold activity of the wild type. Surprisingly, $D_{137}N$ substitution was detected in KerS39, serine protease WP_000790934.1, and WP_061129616.1 (FIG. 8, panels 8-1 to 8-5).

Abdel-Naby et al. demonstrated that combination of chemical/physical mutagenesis on *B. cereus* resulted in 19 amino acid substitutions that led to an improvement of the protease by about 31.17% compared with the wild type; nine of the amino acid substitutions include $I_{242}Y$, $K_{244}R$, $D_{245}A$, $K_{246}R$, $G_{248}N$, $R_{253}V$, $T_{260}H$, $W_{279}R$, and $E_{281}L$ and improved the catalytic efficiency of the enzyme; see Abdel-Naby, M. A. et al., G. E. *Molecular characterization, catalytic, kinetic and thermodynamic properties of protease produced by a mutant of Bacillus cereus*-S6-3. Int. J. Biol. Macromol. 2020, 160, 695-702. A keratinase as disclosed herein may comprise one, two, three or more of these substitutions: $I_{242}Y$, $K_{244}R$, $D_{245}A$, $K_{246}R$, $G_{248}N$, $R_{253}V$, $T_{260}H$, $W_{279}R$, and $E_{281}L$.

Seven substitutions ($N_{117}K$, $V_{195}I$, $A_{290}G$, $S_{295}L$, $R_{297}K$, $T_{364}S$, and $S_{368}T$) observed in the study distinguished KerS26 and its mutant KerS26uv from other keratinase sequences and serine proteases, S8 family peptidase (FIG. 8, panels 8-1 to 8-5). The seven substitutions were also detected in the serine proteases WP_000790937.1, WP_088859495.1, WP_065211756.1, WP_086395645.1, WP_006918592.1, WP_153581315.1, and WP_098771659.1, each incorporated by reference (FIG. 8, panels 8-1 to 8-5).

Keratinase KerS gene sequences were subsequently separated into two groups (FIG. 9). The diversity between the disclosed keratinase sequences was 0.025, however, it was 0.003-0.022 between the disclosed keratinases and those of the serine protease, SS family peptidase *B. cereus* group (FIG. 17). Although the mutant S26uv had 1.73-fold more keratinase activity than the wild S26 strain, no substitutions were detected in keratinase KerS26uv compared to KerS26.

Functional Analysis of Keratinase KerS Gene.

In order to identify protein domains, families, and functional sites, the ScanProsite search tool was used to scan KerS gene for matches against PROSITE profiles and patterns. Functional prediction of keratinase gene resulted in the detection of serine protease subtilase domain (peptidase S8) at amino acid position 119-385 of KerS gene, including the catalytic triad subtilase ASP146, subtilase HIS179, and subtilase SER333 (FIG. 10).

Most of the keratinases are found in the subfamily S8A including 14 keratinases; their active site contains the catalytic triad of Asp, His, and Ser: Martinez, J. P. et al. The catalytic triad plays an essential role in the catalytic mechanism. The triad is positioned in the active site of the enzyme where catalysis takes place and is conserved in all superfamilies of serine protease enzymes; Iván, G. et al., *Four spatial points that define enzyme families.* Biochem. Biophys. Res. Commun. 2009, 383, 417-420. Interestingly, the detected substitutions in KerS gene (FIG. 8, panels 8-1 to 8-5) did not affect the prediction of the subtilase domain and the catalytic triad, and accordingly, the inventors consider that these substitutions did not affect the KerS function. According to the close relationship between KerS and peptidase S8 *B. cereus* group and the prediction of serine protease subtilase family domain and catalytic tried, the inventors consider that the KerS gene belongs to serine protease S8 family peptidase. Keratinases belong to the serine- and metalloprotease families. The major keratinase family is the S8 family, and the subtilisin subfamily members, in particular, have keratinolytic activity; Qiu, J. et al., supra, 2020.

Using InterProScan and NCBI conserved domains search, the inventors KerS showed similarity to peptidases S8 thermitase-like (thermitase-like domain) at position 110-368 (FIG. 11). Thermitase is a serine protease belonging to family SS (subtilases), which includes subtilisin isolated from *Bacillus* species; Barrett, A. J. et al., *"Species" of peptidases*. BIOL. CHEM. 2007, 388, 1151-1157. Thermitase is a thermostable serine proteinase that is more stable against thermal denaturation and proteolytic degradation than most members of the family; Betzel, C. *Thermitase*. In HANDBOOK OF PROTEOLYTIC ENZYMES, 3rd ed.; Rawlings, N., Salvesen, G., Eds.; Academic Press: London, U K, 2013; Volume 2, pp. 3167-3169.

ems shared the highest identity with thermitase alkaline serine protease (100%). However, thermophilic serine proteinase B3ZJ21 showed the highest identity with KerS13 (95.78%). KerS26uv shared 95.48% and 97.59% identity with thermophilic and thermitase protease, respectively. According to Li et al., the keratinase gene (kerT1) shared over 70% identity with the peptidase S8 thermitase family domain and possibly belongs to the serine endoprotease. Li, H. J. et al., Characterization of a new S8 serine protease from marine Sedimentary photobacterium sp. A5-7 and the function of its protease-associated domain. FRONT. MICROBIOL. 2016, 7, 2016.

Physicochemical Characterization of Keratinase KerS Gene.

S8 family peptidase protein sequences representing different *B. cereus* group species were retrieved from NCBI-BLASTp and compared with the keratinase KerS gene to better investigate KerS gene encoding KerS13, KerS13uv+ems, and KerS26uv (Table S2).

TABLE S2

BLASTp analysis of KerS gene (KerS13, KerS13uv + ems, and KerS26uv) and the corresponding similar peptidase S8 *B. cereus* group species.

| Isolate name | No. | Accession No. | Species | % Identity |
|---|---|---|---|---|
| KerS13 | 1 | WP_076873679.1 | S8 family peptidase (*Bacillus cereus* group] | 99.75% |
| | 2 | WP_171484091.1 | S8 family serine peptidase [*Bacillus paranthracis*] | 99.75% |
| | 3 | WP_088068318.1 | S8 family peptidase (Bscallys *thuringiensis*) | 99.24% |
| | 4 | PFJ29283.1 | alkaline serine protease (*Bacillus anthracis*) | 98.99% |
| | 5 | WP_144655882.1 | S8 family peptidase [*Bacillus tropicas*] | 98.99% |
| | 6 | WP_074563627.1 | S8 family peptidase [*Bacillus cereus*] | 98.74% |
| KerS13uv + ems | 1 | WP_061129616.1 | S8 famuly peptidase [*Bacillus cereus*] | 99.75% |
| | 2 | WP_098852855.1 | S8 family peptidase (*Bacillus thuringiensis*] | 98.74% |
| | 3 | WP_197225397.1 | S8 family peptidase (*Bacillus paranthracis*) | 98.49% |
| | 4 | WP_098616758.1 | S8 family peptidase (*Bacillus cereus* group] | 98.24% |
| | 5 | MBL3821420.1 | peptidase S8 [*Bacillus cereus*] | 99.24% |
| | 6 | PES75482.1 | alkaline serine protease [*Bacillus anthracis*] | 98.24% |
| KerS26uv | 1 | WP_078420647.1 | S8 family peptidase [*Bacillus cereus*) | 100% |
| | 2 | WP_044584435.1 | S8 family peptidase [*Bacillus bombysepticus*) | 99.24% |
| | 3 | WP_098356006.1 | S8 family peptidase [*Bacillus thuringiensis*) | 98.99% |
| | 4 | TBL05390.1 | peptidase S8 (*Bacillus paranthracis*] | 98.99% |
| | 5 | WP_213745030.1 | S8 family serine peptidase [*Bacillus toyonensis*) | 98.74% |
| | 6 | WP_099686350.1 | S8 family peptidase (*Bacillus fungorum*] | 98.74% |
| | 7 | WP_226638973.1 | S8 family peptidase (*Bacillus tropicus*) | 98.74% |
| | 8 | WP_098158349.1 | S8 family peptidase [*Bacillus* toyonessie] | 98.49% |

Table S2: BLASTp analysis of KerS gene (KerS13, KerS13uv + ems, and KerS26uv) and the corresponding similar peptidase S8 *B. cereus* group species.

Furthermore, pairwise alignment comparison revealed a high identity between KerS gene and two thermostable serine proteases; thermophilic serine proteinase *B. cereus* (B3ZJ21) and thermitase alkaline serine protease *B. cereus* retrieved from the UniprotKB database (95.58% and 99.09%, respectively). Interestingly, the mutant KerS13uv+

The physicochemical parameters were generated using ProtParam tools of the Expasy server to determine the number of amino acids, molecular weight, the total number of negatively and positively charged amino acids, theoretical pI, grand average of hydropathicity (Gravy), instability, and finally, the aliphatic index (Table 2).

TABLE 2

Physiochemical properties of keratinase KerS primary structure compared with the similar serine proteases of *B. cereus* group retrieved from GenBank database.

| | Serine Protease | N Amino Acids | Molecular Weight | Asp + Glu/ Arg + Lys | Theoretical pI | Gravy Index | Instability Index | Aliphatic Index |
|---|---|---|---|---|---|---|---|---|
| | KerS13 *B. cereus* group | 397 | 42,345.95 | 30/32 | 8.28 | −0.32 | 17.56 | 75.69 |
| 1 | *B. cereus* group | 397 | 42,344.96 | 29/32 | 6.57 | −0.32 | 17.94 | 75.69 |
| 2 | *B. paranthracis* | 397 | 42,374.00 | 30/32 | 8.28 | −0.32 | 17.34 | 76.17 |
| 3 | *B. thuringiensis* | 397 | 42,275.77 | 30/31 | 7.72 | −0.33 | 17.94 | 74.96 |
| 4 | *B. anthracis* | 397 | 42,345.95 | 30/32 | 8.28 | −0.32 | 17.98 | 75.94 |
| 5 | *B. tropicus* | 397 | 42,331.92 | 30/32 | 8.28 | −0.32 | 20.60 | 75.94 |
| 6 | *B. cereus* | 387 | 42,333.89 | 30/32 | 8.28 | −0.34 | 19.09 | 74.96 |

TABLE 2-continued

Physiochemical properties of keratinase KerS primary structure compared with the
similar serine proteases of *B. cereus* group retrieved from GenBank database.

| Serine Protease | N Amino Acids | Molecular Weight | Asp + Glu/ Arg + Lys | Theoretical pI | Gravy Index | Instability Index | Aliphatic Index |
|---|---|---|---|---|---|---|---|
| KerS13uv + ems *B. cereus* group | 397 | 42,344.96 | 29/32 | 8.57 | −0.32 | 17.48 | 75.69 |
| 1  *B. cereus* | 397 | 43,358.99 | 29/32 | 8.57 | −0.32 | 18.59 | 75.94 |
| 2  *B. thuringiensis* | 397 | 42,333.81 | 30/31 | 7.72 | −0.34 | 18.90 | 74.71 |
| 3  *B. paranthracis* | 397 | 42,348.86 | 31/32 | 7.72 | −0.34 | 20.39 | 74.71 |
| 4  *B. cereus* group | 387 | 42,319.78 | 30/31 | 7.72 | −0.34 | 19.28 | 74.46 |
| 5  *B. cereus* | 397 | 42,333.89 | 30/32 | 8.28 | −0.34 | 18.88 | 74.96 |
| 6  *B. anthracis* | 397 | 42,390.94 | 30/32 | 8.28 | −0.35 | 17.80 | 74.71 |
| KerS26uv *B. cereus* group | 397 | 42,333.81 | 30/31 | 7.72 | −0.34 | 19.28 | 74.71 |
| 1  *B. cereus* | 397 | 42,333.81 | 30/31 | 7.72 | −0.34 | 19.28 | 74.71 |
| 2  *B. bombysepticus* | 397 | 42,305.75 | 30/30 | 2.05 | −0.33 | 19.76 | 74.71 |
| 3  *B. thuringiensis* | 397 | 42,365.81 | 30/31 | 7.72 | −0.35 | 18.85 | 73.95 |
| 4  *B. paranthracis* | 347 | 42,319.87 | 30/32 | 8.28 | −0.34 | 18.88 | 74.71 |
| 5  *B. toyonensis* | 397 | 42,261.74 | 30/31 | 7.72 | −0.33 | 19.26 | 74.96 |
| 6  *B. frargerum* | 397 | 42,289.84 | 30/32 | 8.28 | −0.33 | 19.36 | 74.96 |
| 7  *B. tropicus* | 397 | 42,390.94 | 30/32 | 8.28 | −0.35 | 18.18 | 74.71 |
| 8  *B. toyonensis* | 397 | 42,422.95 | 30/32 | 8.29 | −0.35 | 19.60 | 73.98 |

KerS gene and the other peptidase S8 serine proteases composed of 397aa with molecular weight ranged from 42.2-42.4 kDa. The molecular weight of the keratinase gene ranges from 18-200 kDa; Gupta, R. et al., *Microbial keratinases and their prospective applications: An overview*. APPL. MICROBIOL. BIOTECHNOL. 2006, 70, 21-33. Bacillus species are of medium sizes, such as 33 kDa (*B. licheniformis*) and 39 kDa (*B. thuringiensis*); Gegeckas. A. et al., *Keratinolytic proteinase from Bacillus thuringiensis AD-12*. INT. J. BIOL. MACROMOL. 2014, 69, 46-51; Lin, X., et al., *Purification and characterization of a keratinase from a feather-degrading Bacillus licheniformis strain*. APPL. ENVIRON. MICROBIOL. 1992, 58, 3271-3275; Microorganisms 2022, 10, 93 27 of 27. According to Banerjee, A. et al., *Structural characterization and active site prediction of bacterial keratinase through molecular docking*. J. BIOINFORM. 2014, 1, 67-82, negatively and positively charged amino acids determine the structural diversity.

The number of positively charged amino acids (Arg+Lys) was higher than the negatively charged amino acids (Asp+Glu). Banerjee et al. found that positively charged amino acids of *B. licheniformis*, *B. pumilus*, and *B. mojavensis* were higher than negatively charged residues.

The range of theoretical pI was identified between 7.05 and 8.57; KerS13uv+ems showed the highest pI (8.57) compared with KerS13 (8.28) and KerS26uv (7.72); thus, the calculated pI indicates that keratinase KerS possesses an alkaline character with a correlation to the pH stability at 8-9.

GRAVY index showed a low-value range from −0.32 to −0.35. A low GRAVY index indicates low hydrophobicity and high hydrophilicity of the protein, suggesting a better interaction with water.

The predicted instability index <40 indicates that the protein is stable, whereas values >40 suggest that the protein is unstable; Guruprasad. K. et al., *Correlation between stability of a protein and its dipeptide composition: A novel approach for predicting in vivo stability of a protein from its primary sequence*. PROTEIN ENG. DES. SEL. 1990, 4, 155-161. All the protein sequences showed an instability index value of less than 40 (17.34-20.60) suggesting protein stability. KerS13uv+ems showed the lowest instability index (17.48) compared with KerS13 (17.56) and KerS26uv (19.28). The aliphatic index is measured by the relative volume occupied by the aliphatic side chains, which indicates the degree of thermal stability of a protein, and this is wholly dependent on the relative volume of a protein occupied by the aliphatic residues. Dutta, B., et al., *In silico studies on bacterial xylanase enzyme: Structural and functional insight*. J. GENET. ENG. BIOTECHNOL. 2018, 16, 749-756; Ikai, A. *Thermostability and aliphatic index of globular proteins*. J. BIOCHEM. 1980, 88, 1895-1898.

The predicted aliphatic index was 73.95-76.17 which indicates keratinase thermostability. Keratinase of *B. licheniformis* and *Bacillus* sp. showed an instability index of 12.61 and 22.69 and aliphatic index of $3.69 and 60.53, respectively, which implied enzyme stability and significant thermostability; Banerjee, A. et al.; Nnolim. N. E. et al., *Biochemical and molecular characterization of a thermostable alkaline metallo-keratinase from Bacillus sp. Nnolim-K1*. MICROORGANISMS 2020, 8, 1304.

In some embodiments, a keratinase as disclosed herein has an Asp+Glu/Lys ratio ranging from 29, 30, 31 to 32; a pI ranging from 7.7, 7.6, 7.7, 7.8, 7.9, 8.0, 8.1, 8.2, 8.3, 8.4, 8.5, 8.6, to 8.7; a Gravy index ranging from −0.31, −0.32, −0.33, −0.34, −0.35 to 0.36; an instability index ranging from 17, 17.5, 18, 18.5, 19, 19.5, 20.0, 20.5, to 21.0; and/or an aliphatic index ranging from 73.0, 73.5, 74.0, 74.5, 75.0, 75.5, 76.0, to 76.5. These ranges include all intermediate values and subranges.

The physiochemical characteristics such as the instability, gravy, and aliphatic index, as well as the similarity to thermitase domain. thermitase, and thermophilic serine proteases, revealed the stability and significant thermostability of the KerS enzymes disclosed herein. Interestingly, KerSuv+ems shared the highest identity (100%) to the thermitase gene, the lowest instability, and the highest aliphatic index reflecting the high thermostability of this mutant which may be enhanced by the uv+ems mutagenesis. It was reported that the introduction of amino acid substitutions by site-directed mutagenesis on the keratinase gene exhibited high improvement in thermostability, enzyme production, and catalytic activity; Fang, Z. et al.; Liu, B. et al.; Zhang. R. X. et al.

Structure Modeling and Analysis of Wild-Type Keratinase and Mutants.

Ramachandran plot was conducted to validate the stereochemical stability of keratinase structure and to explain the structure of the keratinase of the wild and mutant strains. FIG. 12A showed 91.98% of the amino acid residue in the most favored region, and 1.43% of the remaining residues in the outlier region, which indicates the model is of good quality and stability for in silico studies. The quality factor of the predicted model was observed as 83.09 using ERRAT2. Gupta, S. et al., *Molecular modeling of cloned Bacillus subtilis keratinase and its insinuation in psoriasis treatment using docking studies*. INDIAN J. MICROBIOL. 2017, 57, 485-491 validated the modeled structure of the *B. subtilis* RSE163 keratinase gene using Ramachandran's plot and results showed that 305 of the amino acid residues (84.3%) were in the favored region. Compared with the previous study by Gupta et al., the current model is relatively better as 91.98% of the amino acid residue is in the most favored region.

Molecular Docking Sim of Keratinase KerS Gene.

Molecular docking results indicated that no mutations occurred in the active sites (GLN39 LEU65 SER66 LYS67 SER79 ASN102 TYR104 ASP165 TYR166 VAL167 ASP168 ASN169 ASP170 VAL211 ASP213 ASN214 SER217 GLY218 THR219 ASP221 ALA222 GLN225) of the predicted wild keratinase compared with the mutants (FIG. 12 B).

In some embodiments a keratinase as disclosed herein will contain no mutations to the following residues or to residues corresponding or aligning with these: GLN39 LEU65 SER66 LYS67. SER79. ASN102. TYR104. ASP165. TYR166. VAL167. ASP168. ASN169. ASP170 VAL211. ASP213. ASN214. SER217. GLY218. THR219. ASP221. ALA222. GLN225. In other embodiments a keratinase may contain a mutation, such as an amino acid substitution in at least one, two, three or more of these residues.

The RMSD values and the superimposed structures (FIGS. 12 C,D) indicate that the mutant proteins $D_{137}N$ (0.003 Å) and the seven mutants (0.006 Å) are structurally slightly different from the wild keratinase. However, the mutant of KerS13uv+ems ($D_{137}N$) is not structurally much different from the seven mutants of KerS26uv as the substitutions did not affect the functional domains of the keratinase active site (FIG. 12 C,D).

Data presented in Table 3 showed a slight increase in the binding affinity of the mutant proteins $D_{137}N$ of KerS13uv+ems and the seven mutants of the KerS26uv as they exhibited an affinity score of (−7.17, −7.43), respectively, compared with the wild protein (−6.57). Moreover, the E score2 values of the mutant proteins indicate that they are a minor increase in the binding compared with the wild proteins.

volvementoftheotherimportantresiduessuchasHis85, Asp97, Glu131, Asp160, Glu132, Tyr246, and His247 in hydrogen bonding with the substrates; Kandasamy, S. et al., *Molecular modeling and docking of protease from Bacillus Sp. for the keratin degradation*. BIOCATAL. AGRIC. BIOTECHNOL. 2018, 13, 95-104. A keratinase as disclosed herein may comprise one or more of the residues described above involved in interaction with or hydrogen bonding with the substrate.

As shown herein, novel feather degrading keratinases that were isolated from different keratinolytic bacteria were characterized in vitro and in silico. Physical and chemical mutagenesis resulted in efficient mutants with high keratinase activity and remarkable feather hydrolysis compared with the wild type. Sequence analysis demonstrated that the keratinase KerS gene is a serine protease S8 family of *B. cereus* group with subtilase domain and a typical catalytic triad (Asp, His, and Ser). $D_{137}N$ substitution was observed in the kerS gene KerS13uv+ems, as well as seven different substitutions in KerS26 and its mutant KerS26uv compared with the other KerS gene sequences; the predicted substitutions did not affect the subtilase domain and the active site of the keratinase gene. The predicted low instability index. high aliphatic index, and low GRAVY value of the KerS gene, as well as similarity to thermostable proteases imply that this enzyme is highly thermostable and has excellent solubility in water. Docking analysis confirmed the binding affinity of keratinase KerS13uv+ems and KerS26uv and substrate. Therefore, the new keratinases KerS13uv+ems and KerS26uv presented high keratinolytic activity, efficiency in feather degradation, thermostability and binding affinity providing biotechnological potential as an effective and environmentally friendly alternative to the conventional chemicals used in keratin hydrolysis.

Terminology.

Terminology used herein is for the purpose of describing particular embodiments only and is not intended to be limiting of the invention.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

It should be noted that, as used in the specification and the appended claims, the singular forms "a," "an," and "the"

TABLE 3

The molecular docking of N-succinyl-L-alanyl-L-alanyl-L-prolyl-L phenylalanine 4-nitroanilide S-9205 against keratinase.

|  | Logp | Logs | Affinity | S (kcal/mol) | RMSD_Refine | E_Conf | E_Place | E_Score1 | E_Refine | E_Score2 |
|---|---|---|---|---|---|---|---|---|---|---|
| Wild | 1.13 | −5.76 | −6.57 | −6.6864 | 1.7138 | −16.7596 | −27.6505 | −7.5627 | −39.8656 | −6.6864 |
| D137N | 1.13 | −5.76 | −7.17 | −6.5408 | 1.5868 | −22.9948 | −58.3634 | −8.0156 | −36.007 | −6.5408 |
| 7 Mutant | 1.13 | −5.76 | −7.43 | −7.17 | 7.0603 | −17.7788 | −56.0579 | −5.0721 | −41.3177 | −7.17 |

Logp—the log octanol/water partition coefficient; Logs—Log of the aqueous solubility (mol/L); S—the final score of GBVI/WSA binding free energy; RMSD_Refine—the mean square deviation after refinement; E_Conf—energy conformer; E_Place—score of the placement phase; E_Score1—score of the first step of notation; E_Refine—score of refinement; and E_score2—score of the second step of notation.

Furthermore, FIG. 13 showed the interaction between the keratinase protein and the ligand, the position of the residues (Ser 300, Asn 271) of wild keratinase, (Asp 132, Ser 194) of $D_{137}N$, and (Ala 190) of seven mutants that showed the hydrogen bond with the substrate. The docking results of *Bacillus* sp. showed involvement of Asp160 and Try246 amino acid residues inthebindingwithallcompoundsandininclude plural referents unless the context clearly dictates otherwise. As used herein, the term "and/or" includes any and all combinations of one or more of the associated listed items and may be abbreviated as "/". A and/or B includes A. B, and (A+B).

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−0.2% of the stated value (or range of values), +/−0.5% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/'20% of the stated value (or range of values), etc. Any numerical range recited herein is intended to include all sub-ranges and values subsumed therein.

Any numerical range recited herein is intended to include all sub-ranges and values subsumed therein. Where a range of values is provided, it is to be understood that each intervening value between an upper and lower limit of the range and any other stated or intervening value in that stated range is encompassed within the disclosure. Where the stated range includes upper and lower limits, ranges excluding either of those limits are also included.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-2, 1-3, 1-4, 1-5, 1-6, 1-7, 1-8, 1-9, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, 9-10 as some examples. A range encompasses its endpoints as well as values inside of an endpoint, for example, the range 0-5 includes 0, >0, 1, 2, 3, 4, <5 and 5.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references and does not constitute an admission as to the accuracy of the content of such references.

```

The invention claimed is:

1. A composition comprising a keratinase comprising the amino acid sequence of SEQ ID NO: 11 (KerS1), 13 (KerS1ems), 15 (KerS13), 17 (KerS13uv), 19 (KerS13Uv+ems), 21 (KerS15), 23 (KerS15ems), 25 (KerS26), 27 (KerS26uv), 29 (KerS39), 31 (KerS39ems) or an amino acid sequence that is at least 95% identical to SEQ ID NO: 11, 13, 15, 17, 19, 21, 23, 25, 27, 29 or 31.

2. The composition of claim 1, wherein the keratinase is isolated from cellular components.

3. The composition of claim 1 that comprises a microorganism expressing the keratinase.

4. The composition of claim 1, further comprising a keratin-containing material.

5. The composition of claim 1, further comprising feathers.

6. The composition of claim 1, wherein the keratinase comprises the amino acid sequence of Ker S13 of SEQ ID NO: 15.

7. The composition of claim 1, wherein the keratinase comprises the amino acid sequence of KerS13uv+ems of SEQ ID NO: 19.

8. The composition of claim 1, wherein the keratinase comprises the amino acid sequence of KerS26uv of SEQ ID NO: 27.

9. The composition of claim 3, wherein the microorganism expressing the keratinase is *Bacillus*.

10. The composition of claim 3, wherein the microorganism expressing the keratinase is *Bacillus cereus*.

11. The composition of claim 3, comprising at least one of the amino acid sequences comprising SEQ ID NO: 11, 13, 15, 17, 19, 21, 23, 25, 27, 29 or 31.

12. The composition of claim 4, wherein the keratin-containing material is hair or wool.

13. The composition of claim 4, wherein the keratin-containing material is an animal feed.

* * * * *

                           SEQUENCE LISTING

Sequence total quantity: 31
SEQ ID NO: 1            moltype = DNA  length = 20
FEATURE                 Location/Qualifiers
misc_feature            1..20
                        note = Forward primer 16s rRNA gene
source                  1..20
                        mol_type = other DNA
                        organism = synthetic construct
SEQUENCE: 1
agagtttgat cctggctcag                                                     20

SEQ ID NO: 2            moltype = DNA  length = 22
FEATURE                 Location/Qualifiers
misc_feature            1..22
                        note = reverse primer 16s rRNA gene
source                  1..22
                        mol_type = other DNA
                        organism = synthetic construct
SEQUENCE: 2
tacggctacc ttgttacgac tt                                                  22

SEQ ID NO: 3            moltype = DNA  length = 28
FEATURE                 Location/Qualifiers
misc_feature            1..28
                        note = Keratinase primer
source                  1..28
                        mol_type = other DNA
                        organism = synthetic construct
SEQUENCE: 3
atygagaatc catatgtagg aaaattag                                            28
```

```
SEQ ID NO: 4               moltype = DNA   length = 29
FEATURE                    Location/Qualifiers
misc_feature               1..29
                           note = Keratinase primer
source                     1..29
                           mol_type = other DNA
                           organism = synthetic construct
SEQUENCE: 4
catccctct tttacttwat tactatcat                                              29

SEQ ID NO: 5               moltype = DNA   length = 703
FEATURE                    Location/Qualifiers
misc_feature               1..703
                           note = Bacillus cereus group sp. strain S1 16S ribosomal
                            RNA gene,partial sequence.ACCESSIONOL441832.1
source                     1..703
                           mol_type = other DNA
                           organism = Bacillus cereus
SEQUENCE: 5
ggattaagag cttgctctta tgaagttagc ggcggacggg tgagtaacac gtgggtaacc    60
tgcccataag actgggataa ctccgggaaa ccggggctaa taccggataa cattttgaac    120
cgcatggttc gaaattgaaa ggcggcttcg gctgtcactt atggatggac ccgcgtcgca    180
ttagctagtt ggtgaggtaa cggctcacca aggcaacgat gcgtagccga cctgagaggg    240
tgatcggcca cactgggact gagacacggc ccagactcct acgggaggca gcagtaggga    300
atcttccgca atggacgaaa gtctgacgga gcaacgccgc gtgagtgatg aaggctttcg    360
ggtcgtaaaa ctctgttgtt agggaagaac aagtgctagt tgaataagct ggcaccttga    420
cggtacctaa ccagaaagcc acggctaact acgtgccagc agccgcggta atacgtaggt    480
ggcaagcgtt atccggaatt attgggcgta aagcgcgcgc aggtggtttc ttaagtctga    540
tgtgaaagcc cacggctcaa ccgtggaggg tcattggaaa ctgggagact tgagtgcaga    600
agaggaaagt ggaattccat gtgtagcggt gaaatgcgta gagatatgga ggaacaccag    660
tggcgaaggc gactttctgg tctgtaactg acactgaggc gcg                      703

SEQ ID NO: 6               moltype = DNA   length = 673
FEATURE                    Location/Qualifiers
misc_feature               1..673
                           note = Bacillus cereus group sp. strain S13 16S ribosomal
                            RNA gene,partial sequence.ACCESSIONOL441833.1
source                     1..673
                           mol_type = other DNA
                           organism = Bacillus cereus
SEQUENCE: 6
ggcggacggg tgagtaacac gtgggtaacc tgcccataag actgggataa ctccgggaaa    60
ccggggctaa taccggataa cattttgaac cgcatggttc gaaattgaaa ggcggcttcg    120
gctgtcactt atggatggac ccgcgtcgca ttagctagtt ggtgaggtaa cggctcacca    180
aggcaacgat gcgtagccga cctgagaggg tgatcggcca cactgggact gagacacggc    240
ccagactcct acgggaggca gcagtaggga atcttccgca atggacgaaa gtctgacgga    300
gcaacgccgc gtgagtgatg aaggctttcg ggtcgtaaaa ctctgttgtt agggaagaac    360
aagtgctagt tgaataagct ggcaccttga cggtacctaa ccagaaagcc acggctaact    420
acgtgccagc agccgcggta atacgtaggt ggcaagcgtt atccggaatt attgggcgta    480
aagcgcgcgc aggtggtttc ttaagtctga tgtgaaagcc cacggctcaa ccgtggaggg    540
tcattggaaa ctgggagact tgagtgcaga agaggaaagt ggaattccat gtgtagcggt    600
gaaatgcgta gagatatgga ggaacaccag tggcgaaggc gactttctgg tctgtaactg    660
acactgaggc gcg                                                        673

SEQ ID NO: 7               moltype = DNA   length = 660
FEATURE                    Location/Qualifiers
misc_feature               1..660
                           note = Bacillus cereus group sp. strain S15 16S ribosomal
                            RNA gene,partial sequence.ACCESSIONOL441834.1
source                     1..660
                           mol_type = other DNA
                           organism = Bacillus cereus
SEQUENCE: 7
gagcttgctc ttatgaagtt agcggcggac gggtgagtaa cacgtgggta acctgcccat    60
aagactggga taactccggg aaaccggggc taataccgga taacattttg aaccgcatgg    120
ttcgaaattg aaaggcggct tcggctgtca cttatggatg gacccgcgtc gcattagcta    180
gttggtgagg taacggctca ccaaggcaac gatgcgtagc cgacctgaga gggtgatcgg    240
ccacactggg actgagacac ggcccagact cctacgggag gcagcagtag ggaatcttcc    300
gcaatggacg aaagtctgac ggagcaacgc cgcgtgagtg atgaaggctt tcgggtcgta    360
aaactctgtt gttagggaag aacaagtgct agttgaataa gctggcacct tgacggtacc    420
taaccagaaa gccacggcta actacgtgcc agcagccgcg taatacgta ggtggcaagc     480
gttatccgga attattgggc gtaaagcgcg cgcaggtggt tcttaagtc tgatgtgaaa    540
gcccacggct caaccgtgga gggtcattgg aaactgggag acttgagtgc agaagaggaa    600
agtggaattc catgtgtagc ggtgaaatgc gtagagatat ggaggaacac cagtggcgaa    660

SEQ ID NO: 8               moltype = DNA   length = 1338
FEATURE                    Location/Qualifiers
misc_feature               1..1338
```

|  |  |  |
|---|---|---|
|  | note | = Bacillus cereus group sp. strain S26 16S ribosomal RNA gene,partial sequence.ACCESSIONOL441835.1 |
| source | 1..1338 |  |
|  | mol_type = other DNA |  |
|  | organism = Bacillus cereus |  |

SEQUENCE: 8

```
gttagcggcg gacgggtgag taacacgtgg gtaacctgcc cataagactg ggataactcc   60
gggaaaccgg ggctaatacc ggataacatt ttgaaccgca tggttcgaaa ttgaaaggcg  120
gcttcggctg tcacttatgg atggacccgc gtcgcattag ctagttggtg aggtaacggc  180
tcaccaaggc aacgatgcgt agccgacctg agagggtgat cggccacact gggactgaga  240
cacgccccag actcctacgg gaggcagcag tagggaatct tccgcaatgg acgaaagtct  300
gacggagcaa cgccgcgtga gtgatgaagg ctttcgggtc gtaaaactct gttgttaggg  360
aagaacaagt gctagttgaa taagctggca ccttgacggt acctaaccag aaagccacgg  420
ctaactacgt gccagcagcc gcggtaatac gtaggtggca agcgttatcc ggaattattg  480
ggcgtaaagc gcgcgcaggt ggtttcttaa gtctgatgtg aaagcccacg gctcaaccgt  540
ggagggtcat tggaaactgg gagacttgag tgcagaagag gaaagtgaa ttccatgtgt  600
agcggtgaaa tgcgtagaga tatggaggaa caccagtggc gaaggcgact ttctggtctg  660
taactgacac tgaggcgcga aagcgtgggg agcaaacagg attagatacc ctggtagtcc  720
acgccgtaaa cgatgagtgc taagtgttag agggtttccg ccctttagtg ctgaagttaa  780
cgcattaagc actccgcctg gggagtacgg ccgcaaggct gaaactcaaa ggaattgacg  840
ggggcccgca caagcggtgg agcatgtggt ttaattcgaa gcaacgcgaa gaaccttacc  900
aggtcttgac atcctctgaa aaccctagag atagggcttc tccttcggga gcagagtgac  960
aggtggtgca tggttgtcgt cagctcgtgt cgtgagatgt tgggttaagt cccgcaacga 1020
gcgcaaccct tgatcttagt tgccatcatt aagttgggca ctctaaggtg actgccggtg 1080
acaaaccgga ggaaggtggg gatgacgtca atcatcatg cccttatga cctgggctac 1140
acacgtgcta caatggacag tacaaagagc tgcaagaccg cgaggtgag ctaatctcat 1200
aaaaccgttc tcagttcgga ttgtaggctg caactcgcct acatgaagct ggaatcgcta 1260
gtaatcgcgg atcagcatgc cgcggtgaat acgttcccgg gccttgtaca caccgcccgt 1320
cacaccacga gagtttgt                                              1338
```

| SEQ ID NO: 9 | moltype = DNA length = 701 |
|---|---|
| FEATURE | Location/Qualifiers |
| misc_feature | 1..701 |
|  | note = Bacillus cereus group sp. strain S39 16S ribosomal RNA gene,partial sequence.ACCESSIONOL441836.1 |
| source | 1..701 |
|  | mol_type = other DNA |
|  | organism = Bacillus cereus |

SEQUENCE: 9

```
gcttgctctt atgaagttag cggcggacgg gtgagtaaca cgtgggtaac ctgcccataa   60
gactgggata actccgggaa accggggcta ataccggata acatttttgaa ccgcatggtt  120
cgaaattgaa aggcggcttc ggctgtcact tatggatgga cccgcgtcgc attagctagt  180
tggtgaggta acggctcacc aaggcaacga tgcgtagccg acctgagagg gtgatcggcc  240
acactgggac tgagacacgg cccagactcc tacgggaggc agcagtaggg aatcttccgc  300
aatgacgaa agtctgacgg agcaacgccg cgtgagtgat gaaggctttc gggtcgtaaa  360
actctgttgt tagggaagaa caagtgctag ttgaataagc tggcaccttg acggtaccta  420
accagaaagc cacggctaac tacgtgccag cagccgcgga ataacgtagg tggcaagcgt  480
tatccggaat tattgggcgt aaagcgcgcg caggtggttt cttaagtctg atgtgaaagc  540
ccacggctca accgtggagg gtcattggaa actgggagac ttgagtgcag aagaggaaag  600
tggaattcca tgtgtagcgg tgaaatgcgt agagatatgg aggaacacca gtggcgaagg  660
cgactttctg gtctgtaact gacactgagg cgcgaaagcg t                     701
```

| SEQ ID NO: 10 | moltype = DNA length = 704 |
|---|---|
| FEATURE | Location/Qualifiers |
| misc_feature | 1..704 |
|  | note = Bacillus cereus group sp. strain KerS1 keratinase gene, partialcds.ACCESSIONOL448296.1 |
| source | 1..704 |
|  | mol_type = other DNA |
|  | organism = Bacillus cereus |

SEQUENCE: 10

```
ttgaaaaaca aaatcattgt tttcctatct gttttgtctt ttattattgg tggtttcttc   60
tttaacacga atacttcaag cgctgaaaca tcatctactg attacgttcc taaccaatta  120
atcgttaagt tcaagcaaaa tgcatcttta agtaatgtga aatcttttca taaatctgtc  180
ggagctaatg tcttatctaa agatgataag ttaggttttg aagtcgttca atttttcaaaa  240
ggtactgtaa aagaaaaaat aaagagttat aaaaataatc cagatgtgga atatgcagaa  300
ccgaattatt acgttcacgc cttttggact ccaaacgacc catattttaa aaatcaatat  360
ggattacaaa aaattcaagc tccacaagct tgggatagcc aacgaagtga tcctggtgta  420
aaagtagcca ttattgatac aggagttcaa ggctcacacc ctgatttggc ttcgaaagta  480
atttacgggc atgattatgt tgataacgac aatacatctg atgtgggaa tggtcatggt  540
acacattgcg ctggaattac tggagcactt acgaataaca cgtcggaat tgctggtgtt  600
gccccacaaa cttccatttt atgctgttcgc gtattagata tcaaggaag tggtactctc  660
gatgctgtag cgcaaggtat tcgagaagct gctgattcgg gtgc                  704
```

| SEQ ID NO: 11 | moltype = AA length = 235 |
|---|---|
| FEATURE | Location/Qualifiers |
| REGION | 1..235 |
|  | note = MISC_FEATURE - Keratinase, partial [Bacillus cereus group sp.]GenBank: UIB21025.1 |

```
source                1..235
                      mol_type = protein
                      organism = Bacillus cereus
SEQUENCE: 11
MKNKIIVFLS VLSFIIGGFF FNTNTSSAET SSTDYVPNQL IVKFKQNASL SNVQSFHKSV  60
GANVLSKDDK LGFEVVQFSK GTVKEKIKSY KNNPDVEYAE PNYYVHAFWT PNDPYFKNQY  120
GLQKIQAPQA WDSQRSDPGV KVAIIDTGVQ GSHPDLASKV IYGHDYVDND NTSDDGNGHG  180
THCAGITGAL TNNSVGIAGV APQTSIYAVR VLDNQGSGTL DAVAQGIREA ADSGA       235

SEQ ID NO: 12         moltype = DNA  length = 1194
FEATURE               Location/Qualifiers
misc_feature          1..1194
                      note = Bacillus cereus group sp. strain KerS1ems keratinase
                       gene,complete cds.ACCESSIONOL448297.1
source                1..1194
                      mol_type = other DNA
                      organism = Bacillus cereus
SEQUENCE: 12
ttgaaaaaca aaatcattgt tttcctatct gttttgtctt ttattattgg tggtttcttc  60
tttaacacga atacttcaag cgctgaaaca tcatctactg attacgttcc taaccaatta  120
atcgttaagt tcaagcaaaa tgcatcttta agtaatgtgc aatcttttca taaatctgtc  180
ggagctaatg tcttatctaa agatgataag ttaggttttg aagtcgttca attttcaaaa  240
ggtactgtaa aagaaaaaat aaagagttat aaaaataatc cagatgtgga atatgcagaa  300
ccgaattatt acgttcacgc cttttggact ccaaacgacc catattttaa aaatcaatat  360
ggattacaaa aaattcaagc tccacaagct tgggatagcc aacgaagtga tcctggtgta  420
aaagtagcca ttattgatac aggagttcaa ggctcacacc ctgatttggc ttcgaaagta  480
atttacgggc atgattatgt tgataacgac aatacatctg atgatgggaa tggtcatggt  540
acacattgcg ctggaattac tggagcactt acgaataaca gcgtcggaat tgctggtgtt  600
gccccacaaa cttccattta tgctgttcgc gtattagata atcaaggaag tggtactctc  660
gatgctgtag cgcaaggtat tcgagaagct gctgattcgg gtgcaaaagt aattagttta  720
agtttaggag ctccaaatgg tggtactgca ttacaacagg ccgttcaata tgcatggaat  780
aaaggctctg ttatagttgc agctgctgga aatgctggaa atacaaaagc taattaccct  840
gcttattaca gcgaagtaat tgcagttgct tctacagacc aattagataa gaaatcttca  900
ttttctactt atggtagctg ggttgatgtt gcagcaccag gttcaaatat atattctact  960
tataaaggaa gcacgtatca atcattaagt ggtacatcta tggcaacacc tcatgtcgca  1020
ggagttgctg ctcttttagc aaatcaagga tatagcaata cacaaattcg ccaaattatt  1080
gagtcaactt ctgataaaat tactggtaca ggtacgtact ggaaaaacgg tagagtcaat  1140
gcatataaag ctgtacaata tgcgaagcaa ttacaagaaa ataaagcttc ttaa       1194

SEQ ID NO: 13         moltype = AA  length = 397
FEATURE               Location/Qualifiers
REGION                1..397
                      note = MISC_FEATURE - Keratinase [Bacillus cereus group
                       sp.]GenBank: UIB21026.1
source                1..397
                      mol_type = protein
                      organism = Bacillus cereus
SEQUENCE: 13
MKNKIIVFLS VLSFIIGGFF FNTNTSSAET SSTDYVPNQL IVKFKQNASL SNVQSFHKSV  60
GANVLSKDDK LGFEVVQFSK GTVKEKIKSY KNNPDVEYAE PNYYVHAFWT PNDPYFKNQY  120
GLQKIQAPQA WDSQRSDPGV KVAIIDTGVQ GSHPDLASKV IYGHDYVDND NTSDDGNGHG  180
THCAGITGAL TNNSVGIAGV APQTSIYAVR VLDNQGSGTL DAVAQGIREA ADSGAKVISL  240
SLGAPNGGTA LQQAVQYAWN KGSVIVAAAG NAGNTKANYP AYYSEVIAVA STDQLDKKSS  300
FSTYGSWVDV AAPGSNIYST YKGSTYQSLS GTSMATPHVA GVAALLANQG YSNTQIRQII  360
ESTSDKITGT GTYWKNGRVN AYKAVQYAKQ LQENKAS                           397

SEQ ID NO: 14         moltype = DNA  length = 1194
FEATURE               Location/Qualifiers
misc_feature          1..1194
                      note = Bacillus cereus group sp. strain KerS13 keratinase
                       gene, completecds.ACCESSIONOL448298.1
source                1..1194
                      mol_type = other DNA
                      organism = Bacillus cereus
SEQUENCE: 14
ttgaaaaaca aaatcattgt tttcctatct gttttgtctt ttattattgg tggtttcttc  60
tttaacacga atacttcaag cgctgaaaca tcatctactg attacgttcc taaccaatta  120
atcgttaagt tcaagcaaaa tgcatcttta agtaatgtgc aatcttttca taaatctgtc  180
ggagctaatg tcttatctaa agatgataag ttaggttttg aagtcgttca attttcaaaa  240
ggtactgtaa aagaaaaaat aaagagttat aaaaataatc cagatgtgga atatgcagaa  300
ccgaattatt acgttcacgc cttttggact ccaaacgacc catattttaa aaatcaatat  360
ggattacaaa aaattcaagc tccacaagct tgggatagcc aacgaagtga tcctggtgta  420
aaagtagcca ttattgatac aggagttcaa ggctcacacc ctgatttggc ttcgaaagta  480
atttacgggc atgattatgt tgataacgac aatacatctg atgatgggaa tggtcatggt  540
acacattgcg ctggaattac tggagcactt acgaataaca gcgtcggaat tgctggtgtt  600
gccccacaaa cttccattta tgctgttcgc gtattagata atcaaggaag tggtactctc  660
gatgctgtag cgcaaggtat tcgagaagct gctgattcgg gtgcaaaagt aattagttta  720
agtttaggag ctccaaatgg tggtactgca ttacaacagg ccgttcaata tgcatggaat  780
aaaggctctg ttatagttgc agctgctgga aatgctggaa atacaaaagc taattaccct  840

-continued

```
gcttattaca gcgaagtaat tgcagttgct tctacagacc aattagataa gaaatcttca    900
ttttctactt atggtagctg ggttgatgtt gcagcaccag gttcaaatat atattctact    960
tataaaggaa gcacgtatca atcattaagt ggtacatcta tggcaacacc tcatgtcgca   1020
ggagttgctg ctctttttagc aaatcaagga tatagcaata cacaaattcg ccaaattatt   1080
gagtcaactt ctgataaaat tactggtaca ggtacgtact ggaaaaacgg tagagtcaat   1140
gcatataaag ctgtacaata tgcgaagcaa ttacaagaaa ataaagcttc ttaa         1194

SEQ ID NO: 15           moltype = AA  length = 397
FEATURE                 Location/Qualifiers
REGION                  1..397
                        note = MISC_FEATURE - Keratinase [Bacillus cereus group
                        sp.]GenBank: UIB21027.1
source                  1..397
                        mol_type = protein
                        organism = Bacillus cereus
SEQUENCE: 15
MKNKIIVFLS VLSFIIGGFF FNTNTSSAET SSTDYVPNQL IVKFKQNASL SNVQSFHKSV    60
GANVLSKDDK LGFEVVQFSK GTVKEKIKSY KNNPDVEYAE PNYYVHAFWT PNDPYFKNQY   120
GLQKIQAPQA WDSQRSDPGV KVAIIDTGVQ GSHPDLASKV IYGHDYVDND NTSDDGNGHG   180
THCAGITGAL TNNSVGIAGV APQTSIYAVR VLDNQGSGTL DAVAQGIREA ADSGAKVISL   240
SLGAPNGGTA LQQAVQYAWN KGSVIVAAAG NAGNTKANYP AYYSEVIAVA STDQLDKKSS   300
FSTYGSWVDV AAPGSNIYST YKGSTYQSLS GTSMATPHVA GVAALLANQG YSNTQIRQII   360
ESTSDKITGT GTYWKNGRVN AYKAVQYAKQ LQENKAS                             397

SEQ ID NO: 16           moltype = DNA  length = 1194
FEATURE                 Location/Qualifiers
misc_feature            1..1194
                        note = Bacillus cereus group sp. strain KerS13uv keratinase
                        gene,complete cds.ACCESSIONOL448299.1
source                  1..1194
                        mol_type = other DNA
                        organism = Bacillus cereus
SEQUENCE: 16
ttgaaaaaca aaatcattgt tttcctatct gttttgtctt ttattattgg tggtttcttc    60
tttaacacga atacttcaag cgctgaaaca tcatctactg attacgttcc taaccaatta   120
atcgttaagt tcaagcaaaa tgcatcttta agtaatgtgc aatcttttca taaatctgtc   180
ggagctaatg tcttatctaa agatgataag ttaggttttg aagtcgttca attttcaaaa   240
ggtactgtaa aagaaaaaat aaagagttat aaaaataatc cagatgtgga aatatgcagaa   300
ccgaattatt acgttcacgc cttttggact ccaaacgaac catattttaa aaatcaatat   360
ggattacaaa aaattcaagc tccacaagct tgggatagcc aacgaagtga tcctggtgta   420
aaagtagcca ttattgatac aggagttcaa ggctcacacc ctgatttggc ttcgaaagta   480
atttacgggc atgattatgt tgataacgac aatacactg atgatgggaa tggtcatggt   540
acacatgtcg ctggaattac tggagcactt acgaataaca gcgtcggaat tgctggtgtt   600
gccccacaaa cttccattta tgctgttcgc gtattagata tcaaggaag tggtactctc    660
gatgctgtag cgcaaggtat tcgagaagct gctgattcgg gtgcaaaagt aattagttta   720
agtttaggag ctccaaatgg tggtactgca ttacaacagg ccgttcaata tgcatggaat   780
aaaggctctg ttatagttgc agctgctgga aatgctgaaa atacaaaagc taattaccct   840
gcttattaca gcgaagtaat tgcagttgct tctacagacc aattagataa gaaatcttca    900
ttttctactt atggtagctg ggttgatgtt gcagcaccag gttcaaatat atattctact   960
tataaaggaa gcacgtatca atcattaagt ggtacatcta tggcaacacc tcatgtcgca   1020
ggagttgctg ctctttttagc aaatcaagga tatagcaata cacaaattcg ccaaattatt   1080
gagtcaactt ctgataaaat tactggtaca ggtacgtact ggaaaaacgg tagagtcaat   1140
gcatataaag ctgtacaata tgcgaagcaa ttacaagaaa ataaagcttc ttaa         1194

SEQ ID NO: 17           moltype = AA  length = 397
FEATURE                 Location/Qualifiers
REGION                  1..397
                        note = MISC_FEATURE - Keratinase [Bacillus cereus group
                        sp.]GenBank: UIB21028.1
source                  1..397
                        mol_type = protein
                        organism = Bacillus cereus
SEQUENCE: 17
MKNKIIVFLS VLSFIIGGFF FNTNTSSAET SSTDYVPNQL IVKFKQNASL SNVQSFHKSV    60
GANVLSKDDK LGFEVVQFSK GTVKEKIKSY KNNPDVEYAE PNYYVHAFWT PNDPYFKNQY   120
GLQKIQAPQA WDSQRSDPGV KVAIIDTGVQ GSHPDLASKV IYGHDYVDND NTSDDGNGHG   180
THCAGITGAL TNNSVGIAGV APQTSIYAVR VLDNQGSGTL DAVAQGIREA ADSGAKVISL   240
SLGAPNGGTA LQQAVQYAWN KGSVIVAAAG NAGNTKANYP AYYSEVIAVA STDQLDKKSS   300
FSTYGSWVDV AAPGSNIYST YKGSTYQSLS GTSMATPHVA GVAALLANQG YSNTQIRQII   360
ESTSDKITGT GTYWKNGRVN AYKAVQYAKQ LQENKAS                             397

SEQ ID NO: 18           moltype = DNA  length = 1194
FEATURE                 Location/Qualifiers
misc_feature            1..1194
                        note = Bacillus cereus group sp. strain KerS13uv+ems
                        keratinase gene,complete cds.ACCESSIONOL448300.1
source                  1..1194
                        mol_type = other DNA
                        organism = Bacillus cereus
```

-continued

```
SEQUENCE: 18
ttgaaaaaca aaatcattgt tttcctatct gttttatctt ttattattgg tggtttcttc    60
tttaacacga atacttcaag cgctgaaaca tcatctactg attacgttcc caaccaatta   120
atcgttaagt tcaagcaaaa tgcatcttta agtaatgtgc aatcttttca taaatctgtc   180
ggagctaatg tcttatctaa agatgataag ttaggttttg aagtcgttca attttcaaaa   240
ggtactgtaa agaaaaaaat aaagagttat aaaaataatc cagatgtgga atatgcagaa   300
ccgaattatt acgttcacgc ttttggact  ccaaacgacc catattttaa aaatcaatat   360
ggattacaaa aaattcaagc tccacaagct tgggatagcc aacgaagtaa tcctggtgta   420
aaagtagcca ttattgatac aggagttcaa ggctcacacc ctgatttggc ttcgaaagta   480
atttacgggc atgattatgt tgataacgac aatacatctg atgatgggaa tggtcatggt   540
acacattgcg ctggaattac tggagcactt acgaataaca gcgtcggaat tgctggtgtt   600
gccccacaaa cttccattta tgctgttcgc gtattagata tcaaggaag  tggtactctc   660
gatgctgtag cgcaaggtat tcgagaagct gctgattcgg gtgcaaaagt aattagttta   720
agtttaggag ctccaaatgg tggtactgca ttacaacagg ccgttcaata tgcatggaat   780
aaaggctctg ttatagttgc agctgctgga aatgctggaa atacaaaagc taattaccct   840
gcttattaca gcgaagtaat tgcagttgct tctacagacc aattagataa gaaatcttca   900
ttttctactt atggtagctg ggttgatgtt gcagcaccag gttcaaatat atattctact   960
tataaaggaa gcacgtatca atcattaagt ggtacatcta tggcaacacc tcatgtcgca  1020
ggagttgctg ctcttttagc aaatcaagga tatagcaata cacaaattcg ccaaattatt  1080
gagtcaactt ctgataaaat tactggtaca ggtacgtact ggaaaaacgg tagagtcaat  1140
gcatataaag ctgtacaata tgcgaagcaa ttacaagaaa ataaagcttc ttaa         1194

SEQ ID NO: 19        moltype = AA   length = 397
FEATURE              Location/Qualifiers
REGION               1..397
                     note = MISC_FEATURE - Keratinase [Bacillus cereus group
                     sp.] GenBank: UIB21029.1
source               1..397
                     mol_type = protein
                     organism = Bacillus cereus
SEQUENCE: 19
MKNKIIVFLS VLSFIIGGFF FNTNTSSAET SSTDYVPNQL IVKFKQNASL SNVQSFHKSV    60
GANVLSKDDK LGFEVVQFSK GTVKEKIKSY KNNPDVEYAE PNYYVHAFWT PNDPYFKNQY   120
GLQKIQAPQA WDSQRSNPGV KVAIIDTGVQ GSHPDLASKV IYGHDYVDND NTSDDGNGHG   180
THCAGITGAL TNNSVGIAGV APQTSIYAVR VLDNQGSGTL DAVAQGIREA ADSGAKVISL   240
SLGAPNGGTA LQQAVQYAWN KGSVIVAAAG NAGNTKANYP AYYSEVIAVA STDQLDKKSS   300
FSTYGSWVDV AAPGSNIYST YKGSTYQSLS GTSMATPHVA GVAALLANQG YSNTQIRQII   360
ESTSDKITGT GTYWKNGRVN AYKAVQYAKQ LQENKAS                            397

SEQ ID NO: 20        moltype = DNA  length = 1194
FEATURE              Location/Qualifiers
misc_feature         1..1194
                     note = Bacillus cereus group sp. strain KerS15 keratinase
                     gene, completecds.ACCESSIONOL448301.1
source               1..1194
                     mol_type = other DNA
                     organism = Bacillus cereus
SEQUENCE: 20
ttgaaaaaca aaatcattgt tttcctatct gttttgtctt ttattattgg tggtttcttc    60
tttaacacga atacttcaag cgctgaaaca tcatctactg attacgttcc taaccaatta   120
atcgttaagt tcaagcaaaa tgcatcttta agtaatgtgc aatcttttca taaatctgtc   180
ggagctaatg tcttatctaa agatgataag ttaggttttg aagtcgttca attttcaaaa   240
ggtactgtaa agaaaaaaat aaagagttat aaaaataatc cagatgtgga atatgcagaa   300
ccgaattatt acgttcacgc ttttggact  ccaaacgacc catattttaa aaatcaatat   360
ggattacaaa aaattcaagc tccacaagct tgggatagcc aacgaagtga tcctggtgta   420
aaagtagcca ttattgatac aggagttcaa ggctcacacc ctgatttggc ttcgaaagta   480
atttacgggc atgattatgt tgataacgac aatacatctg atgatgggaa tggtcatggt   540
acacattgcg ctggaattac tggagcactt acgaataaca gcgtcggaat tgctggtgtt   600
gccccacaaa cttccattta tgctgttcgc gtattagata tcaaggaag  tggtactctc   660
gatgctgtag cgcaaggtat tcgagaagct gctgattcgg gtgcaaaagt aattagttta   720
agtttaggag ctccaaatgg tggtactgca ttacaacagg ccgttcaata tgcatggaat   780
aaaggctctg ttatagttgc agctgctgga aatgctggaa atacaaaagc taattaccct   840
gcttattaca gcgaagtaat tgcagttgct tctacagacc aattagataa gaaatcttca   900
ttttctactt atggtagctg ggttgatgtt gcagcaccag gttcaaatat atattctact   960
tataaaggaa gcacgtatca atcattaagt ggtacatcta tggcaacacc tcatgtcgca  1020
ggagttgctg ctcttttagc aaatcaagga tatagcaata cacaaattcg ccaaattatt  1080
gagtcaactt ctgataaaat tactggtaca ggtacgtact ggaaaaacgg tagagtcaat  1140
gcatataaag ctgtacaata tgcgaagcaa ttacaagaaa ataaagcttc ttaa         1194

SEQ ID NO: 21        moltype = AA   length = 397
FEATURE              Location/Qualifiers
REGION               1..397
                     note = MISC_FEATURE - Keratinase [Bacillus cereus group
                     sp.] GenBank: UIB21030.1
source               1..397
                     mol_type = protein
                     organism = Bacillus cereus
```

-continued

```
SEQUENCE: 21
MKNKIIVFLS VLSFIIGGFF FNTNTSSAET SSTDYVPNQL IVKFKQNASL SNVQSFHKSV      60
GANVLSKDDK LGFEVVQFSK GTVKEKIKSY KNNPDVEYAE PNYYVHAFWT PNDPYFKNQY     120
GLQKIQAPQA WDSQRSDPGV KVAIIDTGVQ GSHPDLASKV IYGHDYVDND NTSDDGNGHG     180
THCAGITGAL TNNSVGIAGV APQTSIYAVR VLDNQGSGTL DAVAQGIREA ADSGAKVISL     240
SLGAPNGGTA LQQAVQYAWN KGSVIVAAAG NAGNTKANYP AYYSEVIAVA STDQLDKKSS     300
FSTYGSWVDV AAPGSNIYST YKGSTYQSLS GTSMATPHVA GVAALLANQG YSNTQIRQII     360
ESTSDKITGT GTYWKNGRVN AYKAVQYAKQ LQENKAS                              397

SEQ ID NO: 22              moltype = DNA  length = 1194
FEATURE                    Location/Qualifiers
misc_feature               1..1194
                           note = Bacillus cereus group sp. strain KerS15ems
                            keratinase gene,complete cds.ACCESSIONOL448302.1
source                     1..1194
                           mol_type = other DNA
                           organism = Bacillus cereus
SEQUENCE: 22
ttgaaaaaca aaatcattgt tttcctatct gttttgtctt ttattattgg tggtttcttc      60
tttaacacga atacttcaag cgctgaaaca tcatctactg attacgttcc taaccaatta     120
atcgttaagt tcaagcaaaa tgcatcttta agtaatgtgc aatcttttca taaatctgtc     180
ggagctaatg tcttatctaa agatgataag ttaggttttg aagtcgttca attttcaaaa     240
ggtactgtaa agaaaaaaat aaagagttat aaaaataatc cagatgtgga atatgcagaa     300
ccgaattatt acgttcacgc cttttggact ccaaacgacc catatttaa aaatcaatat     360
ggattacaaa aaattcaagc tccacaagct tgggatagcc aacgaagtga tcctggtgta     420
aaagtagcca ttattgatac aggagttcaa ggctcacacc ctgatttggc ttcgaaagta     480
atttacgggc atgattatgt tgataacgac aatacatctg atgatgggaa tggtcatggt     540
acacattgcg ctggaattac tggagcactt acgaataaca gcgtcggaat tgctggtgtt     600
gccccacaaa cttccattta tgctgttcgc gtattagata tcaaggaag tggtactctc      660
gatgctgtag cgcaaggtat tcgagaagct gctgattcgg gtgcaaaagt aattagttta     720
agtttaggag ctccaaatgg tggtactgca ttcaacagg ccgttcaata tgcatggaat      780
aaaggctctg ttatagttgc agctgctgga aatgctggaa atacaaaagc taattaccct     840
gcttattaca gcgaagtaat tgcagttgct tctacagacc aattagataa gaaatcttca     900
ttttctactt atggtagctg ggttgatgtt gcagcaccag gttcaaatat atattctact     960
tataaaggaa gcacgtatca atcattaagt ggtactccta tggcaacacc tcatgtcgca    1020
ggagttgctg ctctttttagc aaatcaagga tatagcaata cacaaattcg ccaaattatt    1080
gagtcaactt ctgataaaat tactggtaca ggtacgtact ggaaaaacgg tagagtcaat    1140
gcatataaag ctgtacaata tgcgaagcaa ttacaagaaa ataagcttc ttaa           1194

SEQ ID NO: 23              moltype = AA  length = 397
FEATURE                    Location/Qualifiers
REGION                     1..397
                           note = MISC_FEATURE - Keratinase [Bacillus cereus group
                            sp.]GenBank: UIB21031.1
source                     1..397
                           mol_type = protein
                           organism = Bacillus cereus
SEQUENCE: 23
MKNKIIVFLS VLSFIIGGFF FNTNTSSAET SSTDYVPNQL IVKFKQNASL SNVQSFHKSV      60
GANVLSKDDK LGFEVVQFSK GTVKEKIKSY KNNPDVEYAE PNYYVHAFWT PNDPYFKNQY     120
GLQKIQAPQA WDSQRSDPGV KVAIIDTGVQ GSHPDLASKV IYGHDYVDND NTSDDGNGHG     180
THCAGITGAL TNNSVGIAGV APQTSIYAVR VLDNQGSGTL DAVAQGIREA ADSGAKVISL     240
SLGAPNGGTA LQQAVQYAWN KGSVIVAAAG NAGNTKANYP AYYSEVIAVA STDQLDKKSS     300
FSTYGSWVDV AAPGSNIYST YKGSTYQSLS GTSMATPHVA GVAALLANQG YSNTQIRQII     360
ESTSDKITGT GTYWKNGRVN AYKAVQYAKQ LQENKAS                              397

SEQ ID NO: 24              moltype = DNA  length = 1194
FEATURE                    Location/Qualifiers
misc_feature               1..1194
                           note = Bacillus cereus group sp. strain kerS26 keratinase
                            gene, completecds.ACCESSIONOL448303.1
source                     1..1194
                           mol_type = other DNA
                           organism = Bacillus cereus
SEQUENCE: 24
ttgaaaaaca aaatcatcgt tttcctatct gttttatcat ttattattgg tggtttcttc      60
tttaacacga atacttcaag tgctgaaaca tcatctactg attacgttcc taaccaatta     120
atcgttaagt tcaaacaaaa tgcatcttta agtaatgtgc aatcttttca taaatctgtc     180
ggagctaatg tcttatctaa agatgataag ttaggttttg aagtcgtaca attttcaaaa     240
ggtactgtaa agaaaaaaat aaagagttat aaaaataatc cagatgtgga atatgcagaa     300
ccaaattatt acgttcacgc cttttggact ccaaacgacc catatttaa taatcaatat     360
ggattacaaa agattcaagc tccacaagct tgggatagcc aacgaagtga tcctggtgta     420
aaagtagcta ttattgatac aggagttcaa ggctcacacc ctgatctggc ttcgaaagta     480
atttacgggc atgattatgt tgataacgac aatacatctg atgatggtaa tggtcatggt     540
acacattgcg ctggaattac tggagcactt acgaataaca gcatcggaat tgctggtgtt     600
gccccacaaa cttccattta tgctgtccgc gtattagata tcaaggaag tggtactctt      660
gatgctgtag cgcaaggtat tcgagaagct gctgattcgg gtgcaaaagt aattagttta     720
agtttaggag ctccaaatgg tggtactgca ttcaacaag ccgttcaata tgcatggaat      780
aaaggctctg ttatagttgc agctgctgga aatgctggaa atacaaaagc taattaccct     840
```

```
gcttattaca gcgaagtaat tgcagttggt tctacagatc aatcagatag aaaatcttca  900
ttctctactt atggtagctg ggtagatgtt gcagcaccag gttcaaatat atattcaaca  960
tataaaggaa gcacgtatca atcattaagt ggtacatcta tggcaacacc tcatgttgca 1020
ggagtcgctg ctctttttagc aaatcaagga tatagcaata cacaaatccg ccaaattatt 1080
gagtctacta ctgataaaat tagtggtaca ggtacgtact ggaaaaacgg tagagtcaat 1140
gcatataagg ctgtacaata cgctaagcaa ttgcaagaaa ataaagcttc ttaa       1194
```

| | | |
|---|---|---|
| SEQ ID NO: 25 | moltype = AA   length = 397 | |
| FEATURE | Location/Qualifiers | |
| REGION | 1..397 | |
| | note = MISC_FEATURE - Keratinase [Bacillus cereus group sp.] GenBank: UIB21032.1 | |
| source | 1..397 | |
| | mol_type = protein | |
| | organism = Bacillus cereus | |

```
SEQUENCE: 25
MKNKIIVFLS VLSFIIGGFF FNTNTSSAET SSTDYVPNQL IVKFKQNASL SNVQSFHKSV  60
GANVLSKDDK LGFEVVQFSK GTVKEKIKSY KNNPDVEYAE PNYYVHAFWT PNDPYFNNQY 120
GLQKIQAPQA WDSQRSDPGV KVAIIDTGVQ GSHPDLASKV IYGHDYVDND NTSDDGNGHG 180
THCAGITGAL TNNSIGIAGV APQTSIYAVR VLDNQGSGTL DAVAQGIREA ADSGAKVISL 240
SLGAPNGGTA LQQAVQYAWN KGSVIVAAAG NAGNTKANYP AYYSEVIAVG STDQSDRKSS 300
FSTYGSWVDV AAPGSNIYST YKGSTYQSLS GTSMATPHVA GVAALLANQG YSNTQIRQII 360
ESTTDKISGT GTYWKNGRVN AYKAVQYAKQ LQENKAS                         397
```

| | | |
|---|---|---|
| SEQ ID NO: 26 | moltype = DNA   length = 1194 | |
| FEATURE | Location/Qualifiers | |
| misc_feature | 1..1194 | |
| | note = Bacillus cereus group sp. strain kerS26uv keratinase gene,complete cds.ACCESSIONOL448304.1 | |
| source | 1..1194 | |
| | mol_type = other DNA | |
| | organism = Bacillus cereus | |

```
SEQUENCE: 26
ttgaaaaaca aaatcatcgt tttcctatct gttttatcat ttattattgg tggtttcttc   60
tttaacacga atacttcaag tgctgaaaca tcatctactg attacgttcc taaccaatta  120
atcgttaagt tcaaacaaaa tgcatcttta agtaatgtgc aatcttttca taaatctgtc  180
ggagctaatg tcttatctaa agatgataag ttaggttttg aagtcgtaca attttcaaaa  240
ggtactgtaa aagaaaaaat aaaagagttat aaaaataatc cagatgtgga aatatgcgaa  300
ccaaattatt acgttcacgc ctttttggact ccaaacgaac atattttaa taatcaatat  360
ggattacaaa agattcaagc tccacaagct tgggatagcc aacgaagtga tcctggtgta  420
aaagtagcta ttattgatac aggagttcaa ggctcacacc ctgatctggc ttcgaaagta  480
atttacgggc atgattatgt tgataacgac aatacactg atgatggtaa tggtcatggt  540
acacattgcg ctggaattac tggagcactt acgaataaca gcatcggaat tgctggtgtt  600
gccccacaaa cttcaattta tgctgtccgc gtattagata tcaaggaag tggtactctt  660
gatgctgtag cgcaaggtat tcgagaagct gctgattcgg gtgcaaaagt aattagttta  720
agtttaggag ctccaaatgg tggtactgca ttacaacaag ccgttcaata tgcatggaat  780
aaaggctctg ttatagttgc agctgctgga aatgctgaaa atacaaaagc taattacccet  840
gcttattaca gcgaagtaat tgcagttggt tctacagatc aatcagatag aaaatcttca  900
ttctctactt atggtagctg ggtagatgtt gcagcaccag gttcaaatat atattcaaca  960
tataaaggaa gcacgtatca atcattaagt ggtacatcta tggcaacacc tcatgttgca 1020
ggagtcgctg ctctttttagc aaatcaagga tatagcaata cacaaatccg ccaaattatt 1080
gagtctacta ctgataaaat tagtggtaca ggtacgtact ggaaaaacgg tagagtcaat 1140
gcatataagg ctgtacaata cgctaagcaa ttgcaagaaa ataaagcttc ttaa       1194
```

| | | |
|---|---|---|
| SEQ ID NO: 27 | moltype = AA   length = 397 | |
| FEATURE | Location/Qualifiers | |
| REGION | 1..397 | |
| | note = MISC_FEATURE - Keratinase [Bacillus cereus group sp.] GenBank: UIB21033.1 | |
| source | 1..397 | |
| | mol_type = protein | |
| | organism = Bacillus cereus | |

```
SEQUENCE: 27
MKNKIIVFLS VLSFIIGGFF FNTNTSSAET SSTDYVPNQL IVKFKQNASL SNVQSFHKSV  60
GANVLSKDDK LGFEVVQFSK GTVKEKIKSY KNNPDVEYAE PNYYVHAFWT PNDPYFNNQY 120
GLQKIQAPQA WDSQRSDPGV KVAIIDTGVQ GSHPDLASKV IYGHDYVDND NTSDDGNGHG 180
THCAGITGAL TNNSIGIAGV APQTSIYAVR VLDNQGSGTL DAVAQGIREA ADSGAKVISL 240
SLGAPNGGTA LQQAVQYAWN KGSVIVAAAG NAGNTKANYP AYYSEVIAVG STDQSDRKSS 300
FSTYGSWVDV AAPGSNIYST YKGSTYQSLS GTSMATPHVA GVAALLANQG YSNTQIRQII 360
ESTTDKISGT GTYWKNGRVN AYKAVQYAKQ LQENKAS                         397
```

| | | |
|---|---|---|
| SEQ ID NO: 28 | moltype = DNA   length = 886 | |
| FEATURE | Location/Qualifiers | |
| misc_feature | 1..886 | |
| | note = Bacillus cereus group sp. strain KerS39 keratinase gene, partialcds.ACCESSIONOL448305.1 | |
| source | 1..886 | |
| | mol_type = other DNA | |
| | organism = Bacillus cereus | |

```
SEQUENCE: 28
ttgaaaaaca aaatcattgt tttcctatct gttttatctt ttattattgg tggtttcttc    60
tttaacacga atacttcaag cgctgaaaca tcatctactg attacgttcc caaccaatta   120
atcgttaagt tcaagcaaaa tgcatcttta agtaatgtgc aatcttttca taaatctgtc   180
ggagctaatg tcttatctaa agatgataag ttaggttttg aagtcgttca attttcaaaa   240
ggtactgtaa aagaaaaaat aaagagttat aaaaataatc cagatgtgga atatgcagaa   300
ccgaattatt acgttcacgc cttttggact ccaaacgacc catattttaa aaatcaatat   360
ggattacaaa aaattcaagc tccacaagct tgggatagcc aacgaagtaa tcctggtgta   420
aaagtagcca ttattgatac aggagttcaa ggctcacacc ctgatttggc ttcgaaagta   480
atttacgggc atgattatgt tgataacgac aatacatctg atgatgggaa tggtcatggt   540
acacattgcg ctggaattac tggagcactt acgaataaca gcgtcggaat tgctggtgtt   600
gccccacaaa cttccattta tgctgttcgc gtattagata tcaaggaag tggtactctc    660
gatgctgtag cgcaaggtat tcgagaagct gctgattcgg gtgcaaaagt aattagttta   720
agtttaggag ctccaaatgg tggtactgca ttacaacagg ccgttcaata tgcatggaat   780
aaaggctctg ttatagttgc agctgctgga aatgctggaa atacaaaagc taattcccct   840
gcttattaca gcgaagtaat tgcagttgct tctacagacc aattag                  886

SEQ ID NO: 29         moltype = AA  length = 295
FEATURE               Location/Qualifiers
REGION                1..295
                      note = MISC_FEATURE - Keratinase, partial [Bacillus cereus
                        group sp.] GenBank:UIB21034.1
source                1..295
                      mol_type = protein
                      organism = Bacillus cereus
SEQUENCE: 29
MKNKIIVFLS VLSFIIGGFF FNTNTSSAET SSTDYVPNQL IVKFKQNASL SNVQSFHKSV    60
GANVLSKDDK LGFEVVQFSK GTVKEKIKSY KNNPDVEYAE PNYYVHAFWT PNDPYFKNQY   120
GLQKIQAPQA WDSQRSNPGV KVAIIDTGVQ GSHPDLASKV IYGHDYVDND NTSDDGNGHG   180
THCAGITGAL TNNSVGIAGV APQTSIYAVR VLDNQGSGTL DAVAQGIREA ADSGAKVISL   240
SLGAPNGGTA LQQAVQYAWN KGSVIVAAAG NAGNTKANYP AYYSEVIAVA STDQL        295

SEQ ID NO: 30         moltype = DNA  length = 809
FEATURE               Location/Qualifiers
misc_feature          1..809
                      note = Bacillus cereus group sp. strain KerS39ems
                        keratinase gene,partial cds.ACCESSIONOL448306.1
source                1..809
                      mol_type = other DNA
                      organism = Bacillus cereus
SEQUENCE: 30
ttgaaaaaca aaatcattgt tttcctatct gttttgtctt ttattattgg tggtttcttc    60
tttaacacga atacttcaag cgctgaaaca tcatctactg attacgttcc taaccaatta   120
atcgttaagt tcaagcaaaa tgcatcttta agtaatgtgc aatcttttca taaatctgtc   180
ggagctaatg tcttatctaa agatgataag ttaggttttg aagtcgttca attttcaaaa   240
ggtactgtaa aagaaaaaat aaagagttat aaaaataatc cagatgtgga atatgcagaa   300
ccgaattatt acgttcacgc cttttggact ccaaacgacc catattttaa aaatcaatat   360
ggattacaaa aaattcaagc tccacaagct tgggatagcc aacgaagtga tcctggtgta   420
aaagtagcca ttattgatac aggagttcaa ggctcacacc ctgatttggc ttcgaaagta   480
atttacgggc atgattatgt tgataacgac aatacatctg atgatgggaa tggtcatggt   540
acacattgcg ctggaattac tggagcactt acgaataaca gcgtcggaat tgctggtgtt   600
gccccacaaa cttccattta tgctgttcgc gtattagata tcaaggaag tggtactctc    660
gatgctgtag cgcaaggtat tcgagaagct gctgattcgg gtgcaaaagt aattagttta   720
agtttaggag ctccaaatgg tggtactgca ttacaacagg ccgttcaata tgcatggaat   780
aaaggctctg ttatagttgc agctgctgg                                     809

SEQ ID NO: 31         moltype = AA  length = 270
FEATURE               Location/Qualifiers
REGION                1..270
                      note = MISC_FEATURE - Keratinase, partial [Bacillus cereus
                        group sp.] GenBank:UIB21035.1
source                1..270
                      mol_type = protein
                      organism = Bacillus cereus
SEQUENCE: 31
MKNKIIVFLS VLSFIIGGFF FNTNTSSAET SSTDYVPNQL IVKFKQNASL SNVQSFHKSV    60
GANVLSKDDK LGFEVVQFSK GTVKEKIKSY KNNPDVEYAE PNYYVHAFWT PNDPYFKNQY   120
GLQKIQAPQA WDSQRSDPGV KVAIIDTGVQ GSHPDLASKV IYGHDYVDND NTSDDGNGHG   180
THCAGITGAL TNNSVGIAGV APQTSIYAVR VLDNQGSGTL DAVAQGIREA ADSGAKVISL   240
SLGAPNGGTA LQQAVQYAWN KGSVIVAAAG                                    270
```